(12) United States Patent
Yeung et al.

(10) Patent No.: US 7,918,879 B2
(45) Date of Patent: Apr. 5, 2011

(54) EXPANDABLE FASTENER WITH COMPRESSIVE GRIPS

(76) Inventors: Jeffrey Eric Yeung, San Jose, CA (US); Teresa T. Yeung, San Jose, CA (US)

( * ) Notice: Subject to any disclaimer, the term of this patent is extended or adjusted under 35 U.S.C. 154(b) by 1360 days.

(21) Appl. No.: 10/913,041

(22) Filed: Aug. 5, 2004

(65) Prior Publication Data

US 2005/0055027 A1    Mar. 10, 2005

Related U.S. Application Data

(63) Continuation of application No. PCT/US03/02856, filed on Jan. 31, 2003.

(60) Provisional application No. 60/359,394, filed on Feb. 25, 2002.

(51) Int. Cl.
- A61B 17/04 (2006.01)
- A61B 17/84 (2006.01)
- A61F 2/08 (2006.01)
- A61B 17/10 (2006.01)

(52) U.S. Cl. ............................ 606/300; 606/75; 606/139

(58) Field of Classification Search .................. 606/329, 606/219–221, 75, 300, 232, 301, 304, 151; 411/439, 448, 457, 459, 501, 502, 514, 515, 411/48, 82, 42, 513, 179, 359, 446, 447, 411/450; 623/16.11, 17.11, 17.15
See application file for complete search history.

(56) References Cited

U.S. PATENT DOCUMENTS

| | | | |
|---|---|---|---|
| 4,884,572 A | 12/1989 | Bays et al. | |
| 4,895,148 A | 1/1990 | Bays et al. | |
| 5,486,197 A * | 1/1996 | Le et al. | 606/232 |
| 5,791,845 A * | 8/1998 | Fulop | 411/42 |
| 5,957,953 A * | 9/1999 | DiPoto et al. | 606/232 |
| 6,129,763 A * | 10/2000 | Chauvin et al. | 623/17.11 |
| 6,251,143 B1 * | 6/2001 | Schwartz et al. | 623/23.72 |

* cited by examiner

Primary Examiner — (Jackie) Tan-Uyen T Ho
Assistant Examiner — Dianne Dornbusch
(74) Attorney, Agent, or Firm — GSS Law Group

(57) ABSTRACT

Anchoring elements of a fastener are made elastically curved. The curvatures of the elements are resiliently straightened by a trocar for tissue insertion. As the trocar is withdrawn, the anchoring elements resume the curved configuration, laterally pressing the elements against tissue to anchor the fastener.

57 Claims, 36 Drawing Sheets

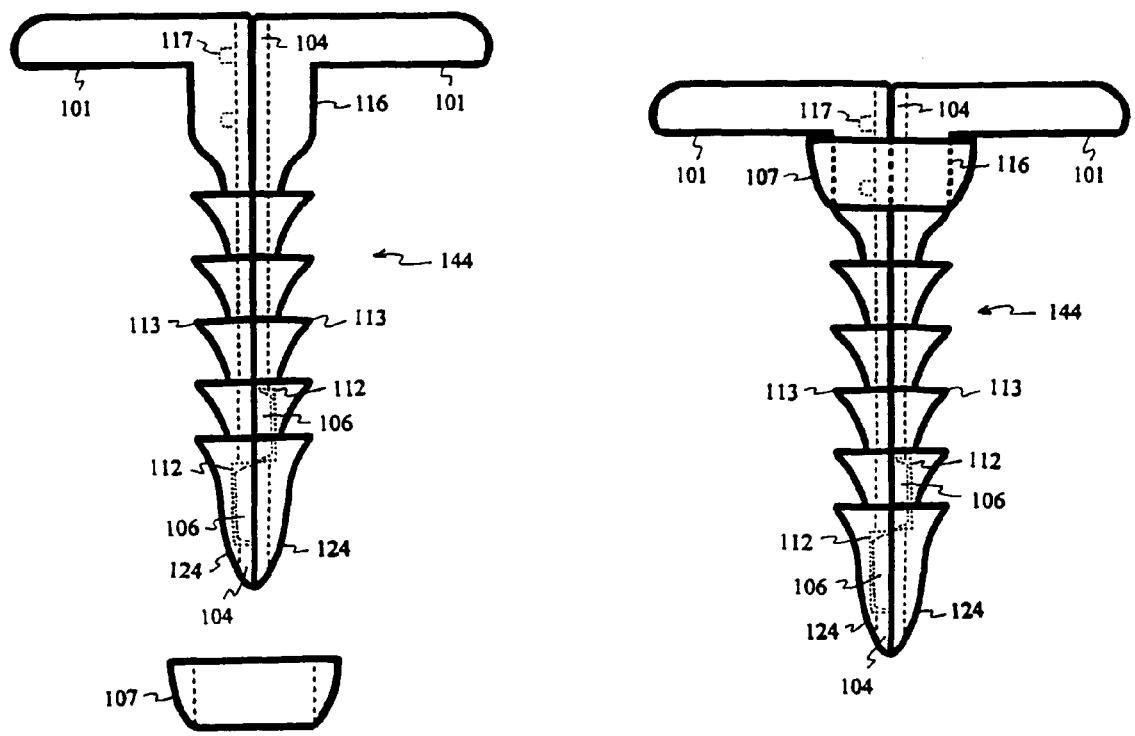
Figure 3
Figure 4
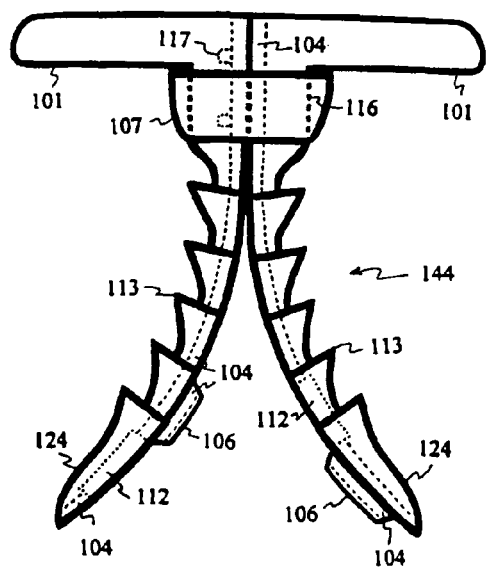
Figure 5

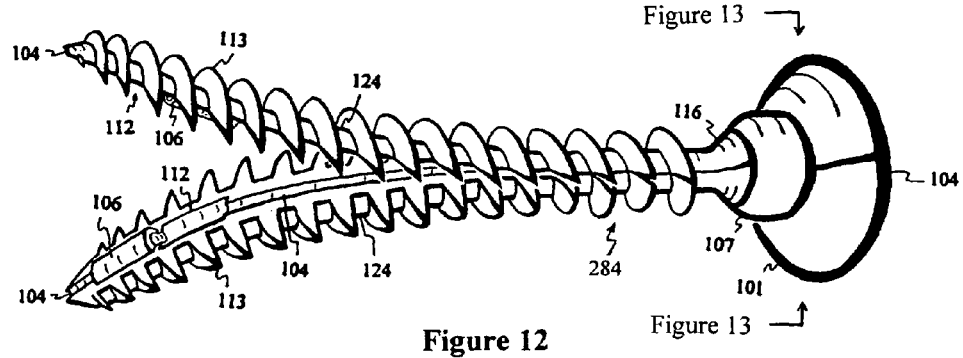
Figure 12
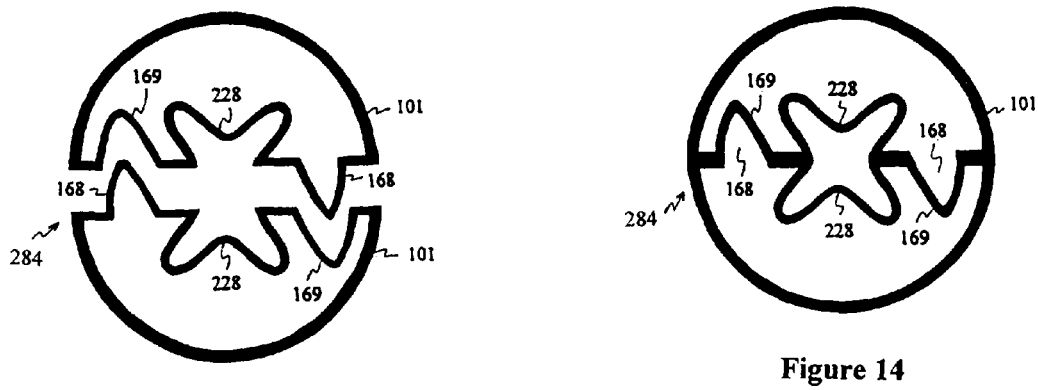
Figure 13
Figure 14
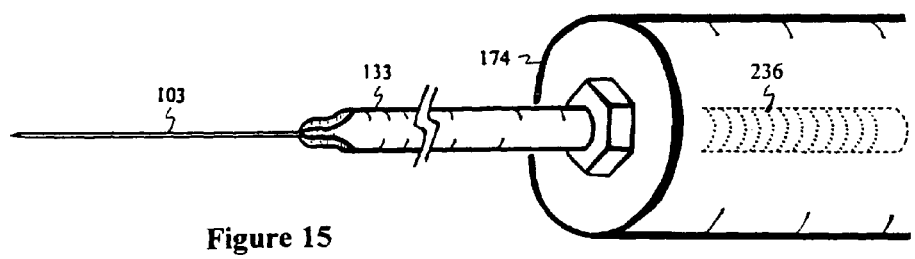
Figure 15
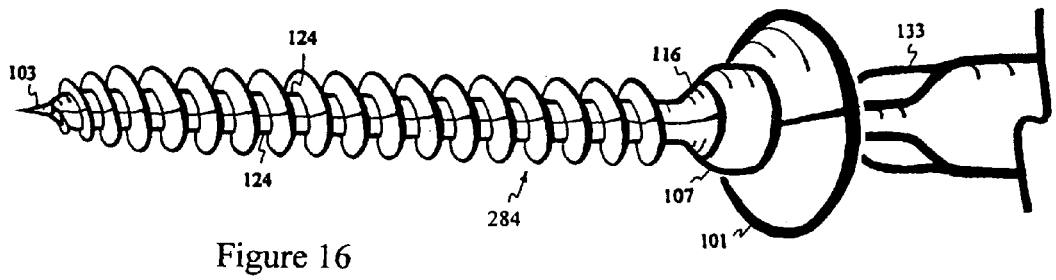
Figure 16

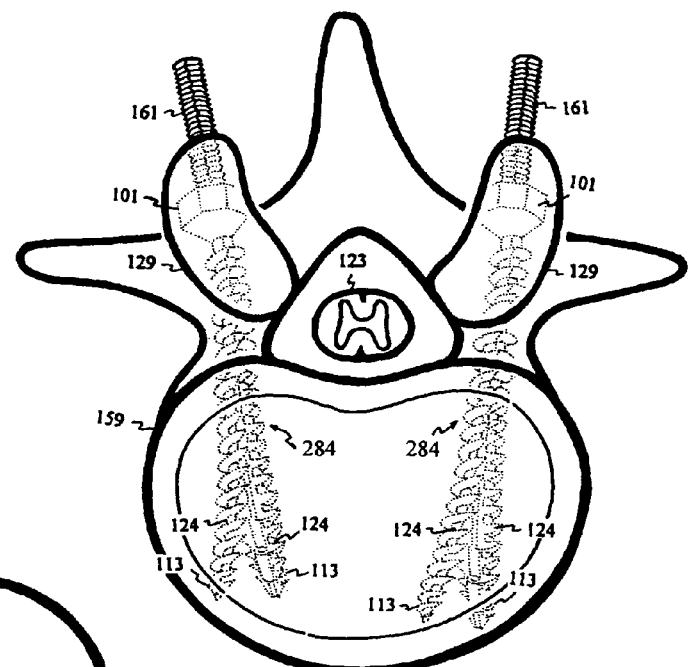
Figure 27
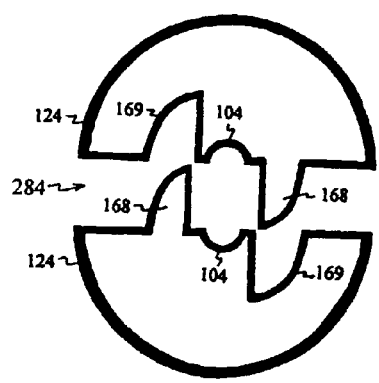
Figure 28
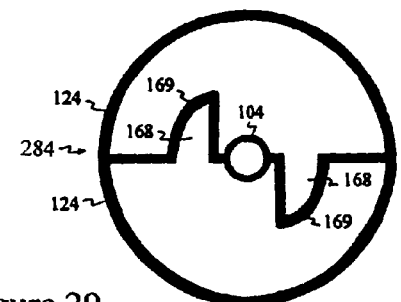
Figure 29
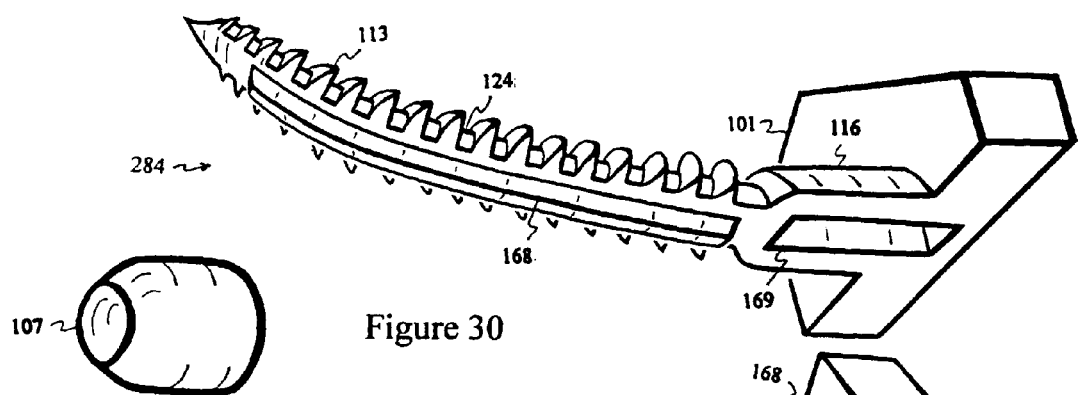
Figure 30
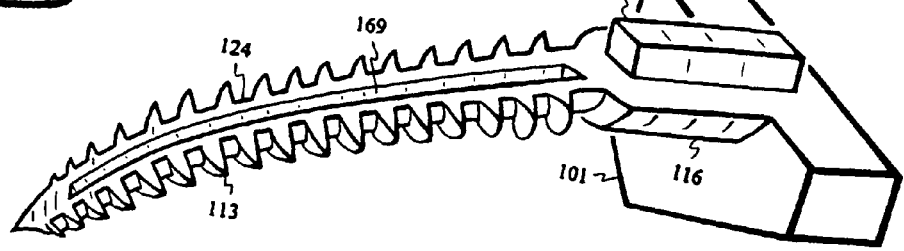

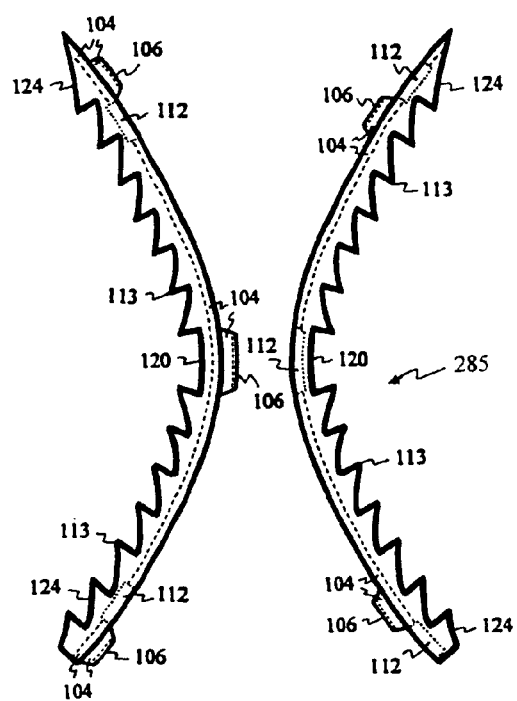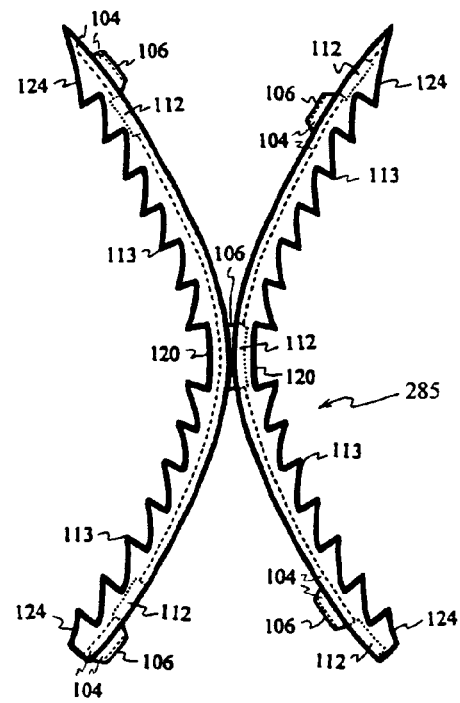
Figure 35
Figure 36
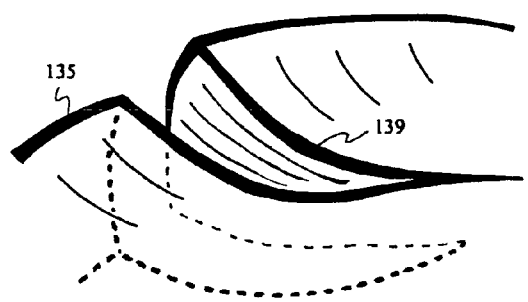
Figure 37
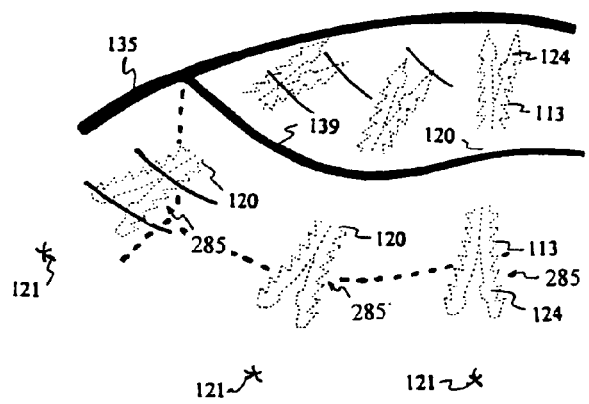
Figure 38

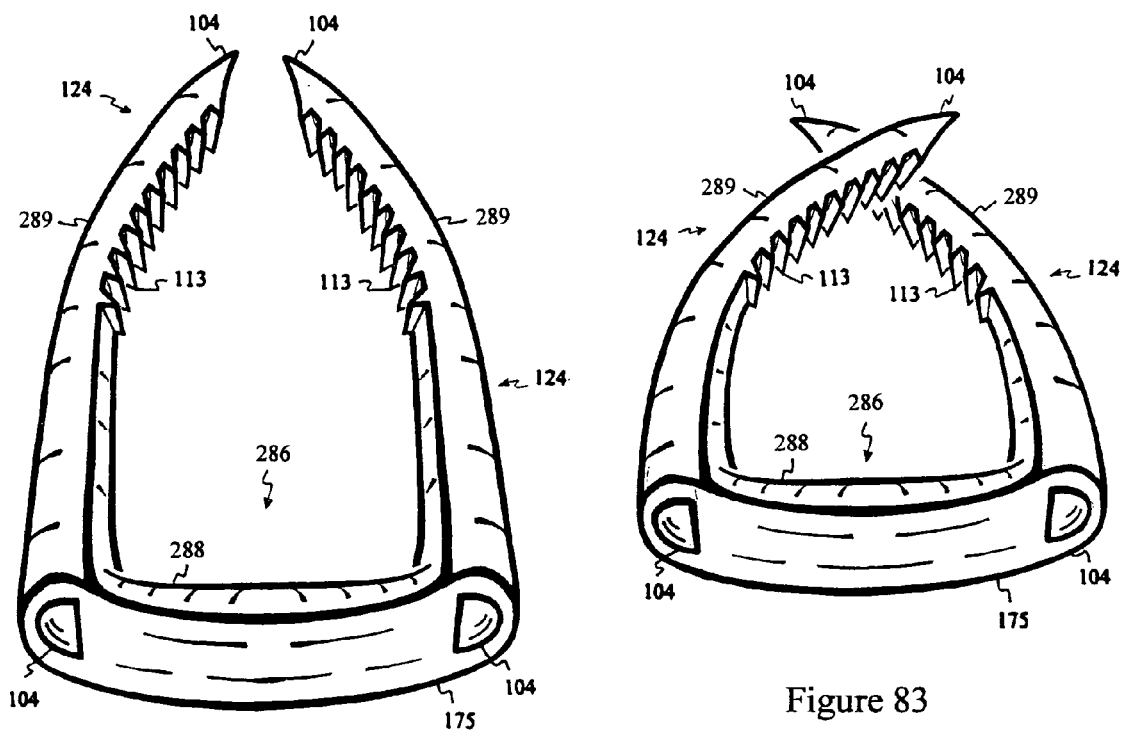
Figure 82
Figure 83
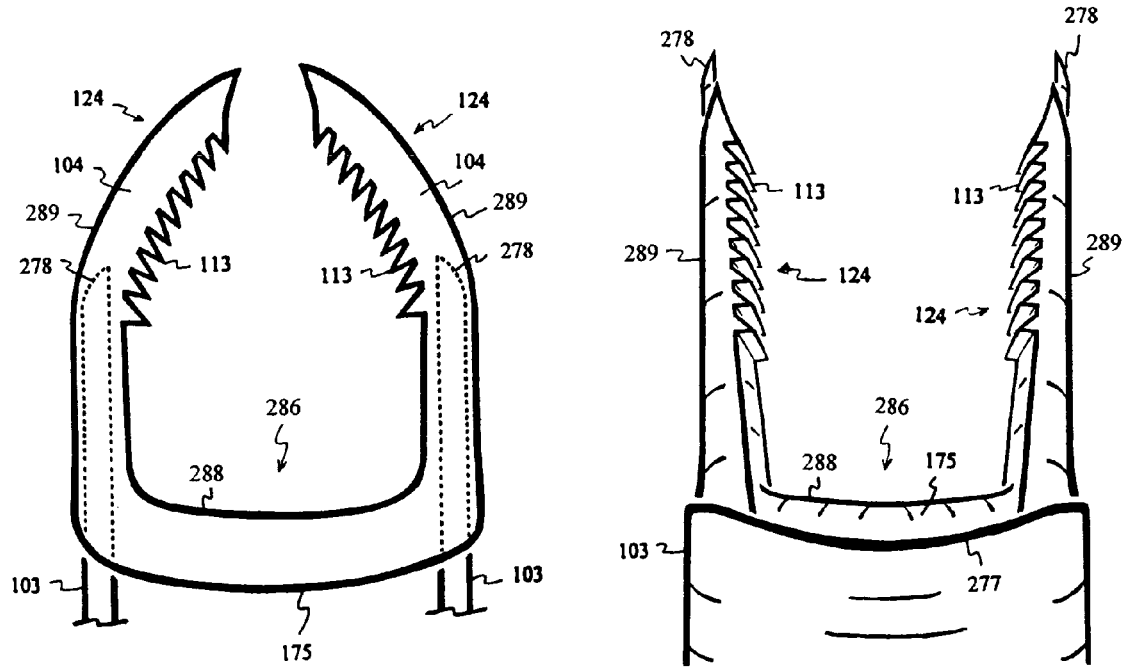
Figure 84
Figure 85

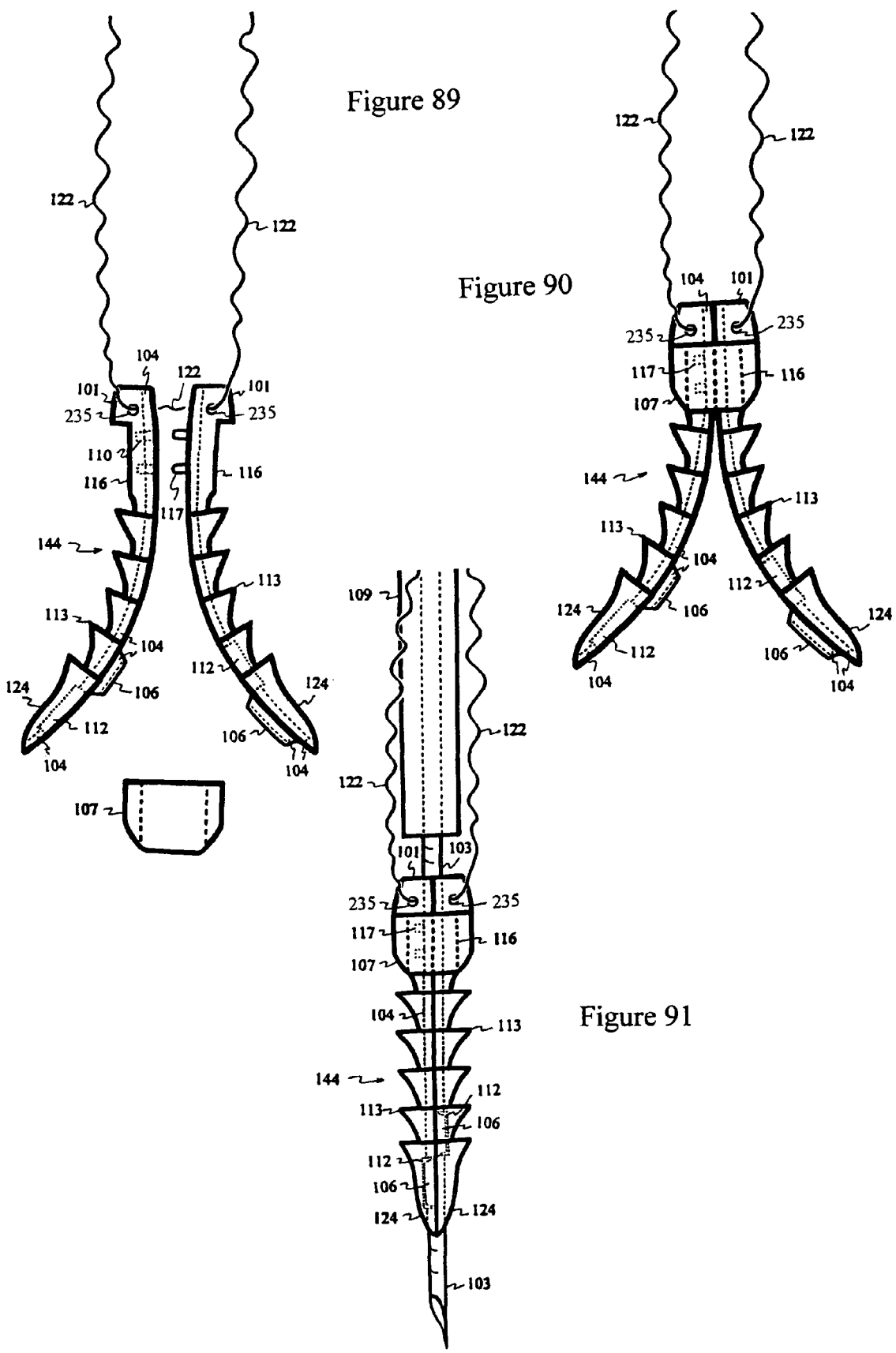

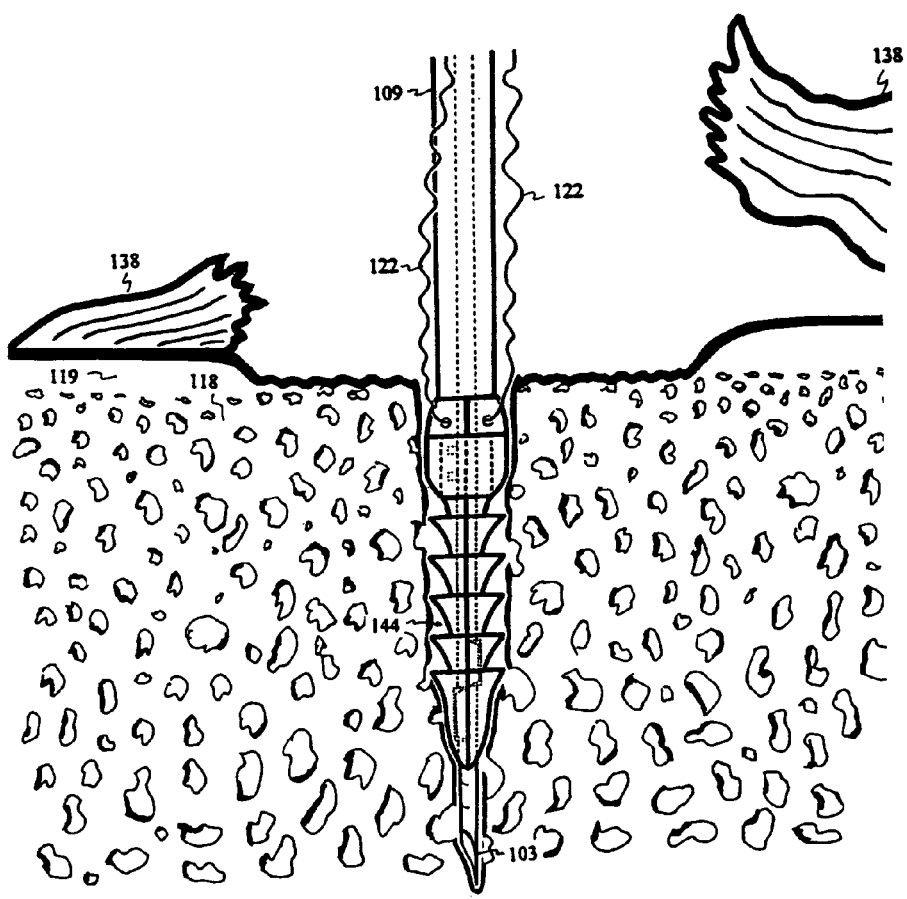
Figure 92
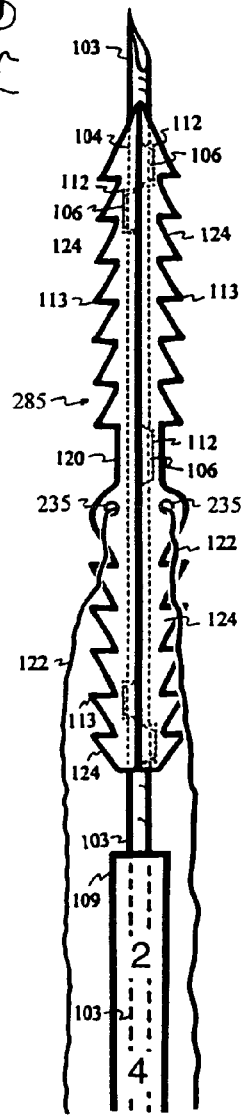
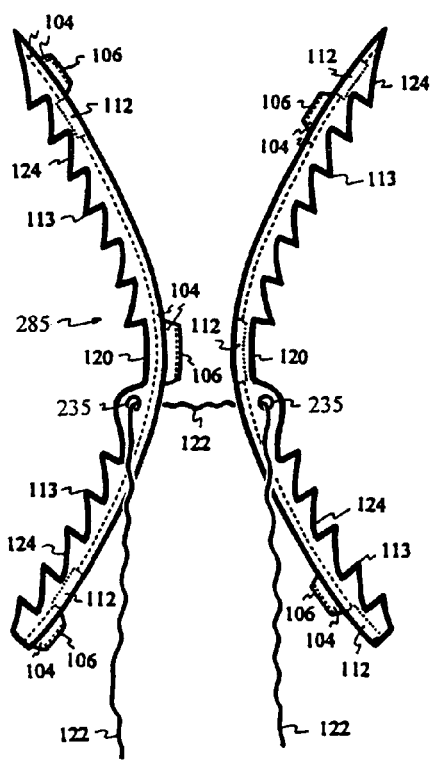
Figure 93
Figure 94

EXPANDABLE FASTENER WITH COMPRESSIVE GRIPS

CROSS-REFERENCES TO OTHER APPLICATIONS

This application is a continuation of PCT Application Ser. No. PCT/US03/02856 filed Jan. 31, 2003, which claimed priority of U.S. Provisional Application No. 60/359,394 filed on Feb. 25, 2002.

FIELD OF INVENTION

This invention is an expandable fastener delivered by a trocar or a needle into tissue. As the trocar is withdrawn, the fastener opens and anchors within tissue.

BACKGROUND

Tendon and ligament tears are common in sports injuries and trauma. Surgical repair of the tears can be invasive with many possible complications, including painful adhesions of scar tissue. Most patients are conservatively treated with immobilization. Only about 35% of orthopaedic trauma cases are treated surgically.

Many bone anchors have been studied and developed to reattach torn tissues. In general, metallic and non-degradable polymeric anchors or staples can fasten torn tissues well; but with time, the non-degradable device can migrate into undesirable places, such as joints. On the other hand, Suretac™ is degradable and easily deployed; however failure due to low pull out strength is a common concern. U.S. Pat. Nos. 4,884,572 and 4,895,148 issued on Dec. 5, 1989 and Jan. 23, 1990 respectively by F. Barry Bays are related to a tissue repairing tack similar to Suretac™ in the market. The tack contains a head, a cylindrical shaft with barbs and a lumen open from the head to the distal end of the shaft. For delivery of the tack, a needle is inserted into the lumen and protruded beyond the distal end of the shaft of the tack. The needle carrying the tack pierces through the torn tissue into bone. The barbs of the tack engage with bone tissue to hold the torn tissue in place. The needle is then withdrawn from the bone and the tack. The tissue gripping strength of the barbs or threads of the tack is very limited, especially in poor quality bone. Therefore, the pull out strength of the tack is generally low. Healing of the torn tissue requires secure contact to the cancellous bone. The low pull out strength often contributes to tack loosening, forming a gap between the bone and supposedly reattached tissue. As a result, tissue reattachment is unsuccessful; weakness and pain persist.

SUMMARY OF INVENTION

Pull out strength is one of the most important criteria in biomechanical testing to evaluate the performance of a tack, staple, anchor or fastener. A new type of expandable fastener is made with elastically curved legs containing tissue-gripping elements. The legs contain semi-cylindrical troughs and trocar engaging rings or retainers. The elastically curved legs can be resiliently straightened and closed to form a shaft for tissue penetration. In the closed position, the semi-cylindrical troughs of the elastic legs form a lumen with the retainers aligned in series. A needle or trocar is inserted into the lumen through the aligned retainers to bind or link the elastically straightened legs; then the needle protrudes beyond the distal end of the expandable fastener. The trocar serves two functions: (1) to restrict or bind the elastic legs together and prevent them from opening, and (2) to spearhead the puncturing of tissue for delivering the expandable fastener. As the trocar is withdrawn from tissue and fastener, the elastic curvatures of the legs resume, pressing and anchoring the gripping elements laterally into the tissue.

| REFERENCE NUMBERS | |
|---|---|
| 100 | Intervertebral disc |
| 101 | Head of fastener |
| 103 | Trocar, needle or K-wire |
| 104 | Trough, groove or lumen |
| 105 | End plate |
| 106 | Trocar retainer or passage |
| 107 | Assembly ring or clip |
| 108 | Tack grips |
| 109 | Compressive sleeve |
| 110 | Peg hole |
| 111 | Disc compressor |
| 112 | Indentation or recess |
| 113 | Gripping element |
| 116 | Neck of fastener |
| 117 | Peg |
| 118 | Cancellous bone |
| 119 | Cortical bone |
| 120 | Counter junction |
| 121 | Puncture hole |
| 122 | Suture |
| 123 | Spinal cord |
| 124 | Expandable leg |
| 128 | Nucleus pulposus |
| 129 | Facet joint |
| 133 | Drive |
| 144 | Tack fastener |
| 153 | Marker |
| 159 | Vertebral body |
| 160 | Tissue ingrowth opening |
| 161 | Threaded portion |
| 165 | Step of a needle or trocar |
| 168 | Tongue |
| 169 | Groove |
| 174 | Handle of driver |
| 175 | Bridge of staple |
| 189 | Socket |
| 194 | Nerve |
| 196 | Retractor |
| 235 | Suture opening |
| 228 | Phillips cross slot |
| 236 | Screw thread |
| 276 | Annular contact surface |
| 277 | Base of double trocar |
| 278 | Semiconic tip |
| 279 | Sleeve |
| 280 | Distal end of compressive sleeve |
| 281 | Recess for gripping element |
| 282 | Spine restrictive device |
| 283 | Hook & loop, or VELCRO ™ |
| 284 | Screw fastener |
| 285 | Counter-gripping fastener |
| 286 | Staple fastener |
| 287 | Enlarged distal surface of sleeve |
| 288 | Inner surface of the bridge |
| 289 | Retainer or passage of staple |

BRIEF DESCRIPTION OF DRAWINGS

FIG. 3 shows the elastically curved legs 124 resiliently straightened to fit the trocar retainers 106 into the indentations 112.

FIG. 4 indicates sliding of the ring 107 over the straightened legs 124 to restrain the neck 116 of the tack fastener 144. The joined troughs 104 form a lumen 104.

FIG. 5 shows elastic opening of the curved legs 124 with the tightly fitted ring 107 holding the assembled tack fastener 144.

FIG. 12 shows another three-piece assembled screw fastener 284 with self-tapping thread functioning as the gripping elements 113. The cross section of the head 101 is shown in FIG. 13.

FIG. 13 depicts the adjoining surfaces of the top and bottom pieces containing tongues 168 and grooves 169 with a Phillips cross-slot 228 on the screw head 101.

FIG. 14 shows the fit between the tongues 168 and grooves 169 to prevent twisting between the top and bottom pieces during tightening of the screw fastener 284. The lumen 104 is extended into the screw fastener 284 from the bottom of the Phillips slot 228.

FIG. 15 shows a trocar 103 protruding from the tip of a Phillips screwdriver 133.

FIG. 16 shows the trocar 103 inserted through the screw fastener 284, binding the trocar retainers 106 together to keep the legs 124 from resiliently opening.

FIG. 27 shows the screw fasteners 284 with threaded portion 161 being used as pedicle screws in the vertebral body 159.

FIG. 28 shows a cross section of the screw fastener 284 with matching tongues 168 and grooves 169 on the adjoining surfaces.

FIG. 29 shows engagement of the tongues 168 and grooves 169 bridging the adjoining surfaces to prevent twisting of the legs 124 during advancement into bone.

FIG. 30 shows a three piece screw fastener 284 with curved legs 124 containing tongues 168 and grooves 169.

FIG. 35 shows the elastically curved legs 124 of the counter-gripping fastener 285 with trocar retainers 106 sized and configured to fit into opposing indentations 112.

FIG. 36 indicates the assembly of the counter-gripping fastener 285. The ring 107, as shown in FIG. 33, is used to cover and latch over the counter junction 120.

FIG. 37 depicts a portion of a meniscus 135 with a tear 139.

FIG. 38 shows bridging and fastening of the meniscal tear 139 by multiple counter-gripping fasteners 285.

FIG. 82 shows a staple fastener 286 with inwardly curved legs 124.

FIG. 83 shows a staple fastener 286 with overlapping legs 124.

FIG. 84 depicts trocars 103 insertion by sliding the semiconic tips 278 against the external walls of the inwardly curved legs 124 of the staple fastener 286.

FIG. 85 shows resilient straightening of the inwardly curving legs 124 by the rigid trocars 103.

FIG. 89 shows a side view of a three-piece resilient fastener 144, similar to the one in FIG. 1, containing a suture 122 through suture openings 235.

FIG. 90 shows the assembled fastener 144 containing the suture 122.

FIG. 91 shows a trocar 103 linking both trocar retainers 106 of the left and the right pieces to resiliently straighten the legs 124 of the fastener 144.

FIG. 92 depicts the leading trocar 103 and compression of the compressive sleeve 109 delivering the suture fastener 144 into a bleeding cancellous bone 118.

FIG. 93 depicts components of a suture counter-gripping fastener 285 containing four elastically curved legs 124 similar to the components shown in FIG. 35.

FIG. 94 depicts resilient straightening of the legs 124 of the suture fastener 285 by inserting a trocar 103 through the retainers 106 in preparation for delivery.

DETAILED DESCRIPTION OF THE EMBODIMENTS

Figure 1:
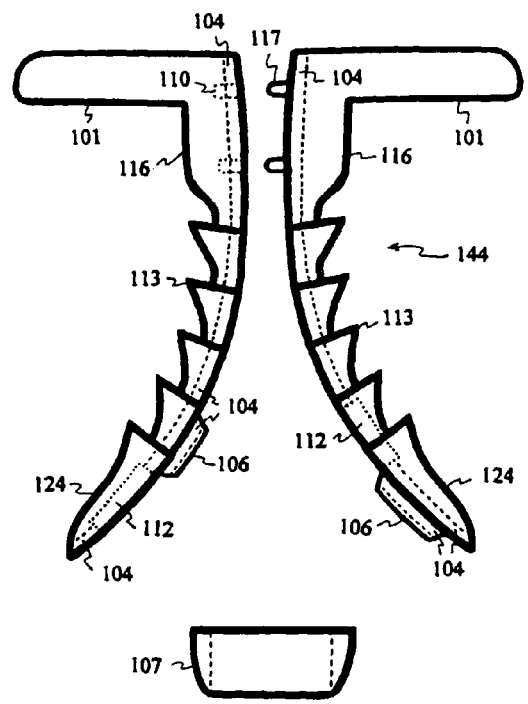
FIG. 1 depicts a side view of elastically curved pieces containing heads 101 and legs 124 above a ring 107 for composing an expandable tack fastener 144.

Although molding, casting or machining the expandable fastener as a single piece is possible, the expandable fasteners are assembled from individual parts to clarify the mechanisms and functions. In addition, the parts can be made with different materials to enhance performances of the expandable fasteners. FIG. 1 depicts a side view of the three components of the expandable tack fastener 144. Two curved pieces or sections are made with elastic material containing generally semi-circular heads 101, necks 116 and legs 124 with outward facing gripping elements 113 and longitudinal troughs 104 or grooves in the interior sides. FIG. 1 also shows pegs 117 protruding from the interior side of the right piece at the head 101 and neck 116 regions. In the interior side of the left piece, peg holes 110 are positioned, sized, and configured to fit the pegs 117. On both interior sides of the right and left legs 124, semi-cylindrical trocar retainers 106 or passages arch over the troughs 104. Adjacent to the retainers 106, indentations 112 or recesses are sunken into the trough 104. The indentation 112 on the right elastic piece is positioned, sized and configured to fit or house the retainer 106 on the left elastic piece and vice versa.

Figure 2:
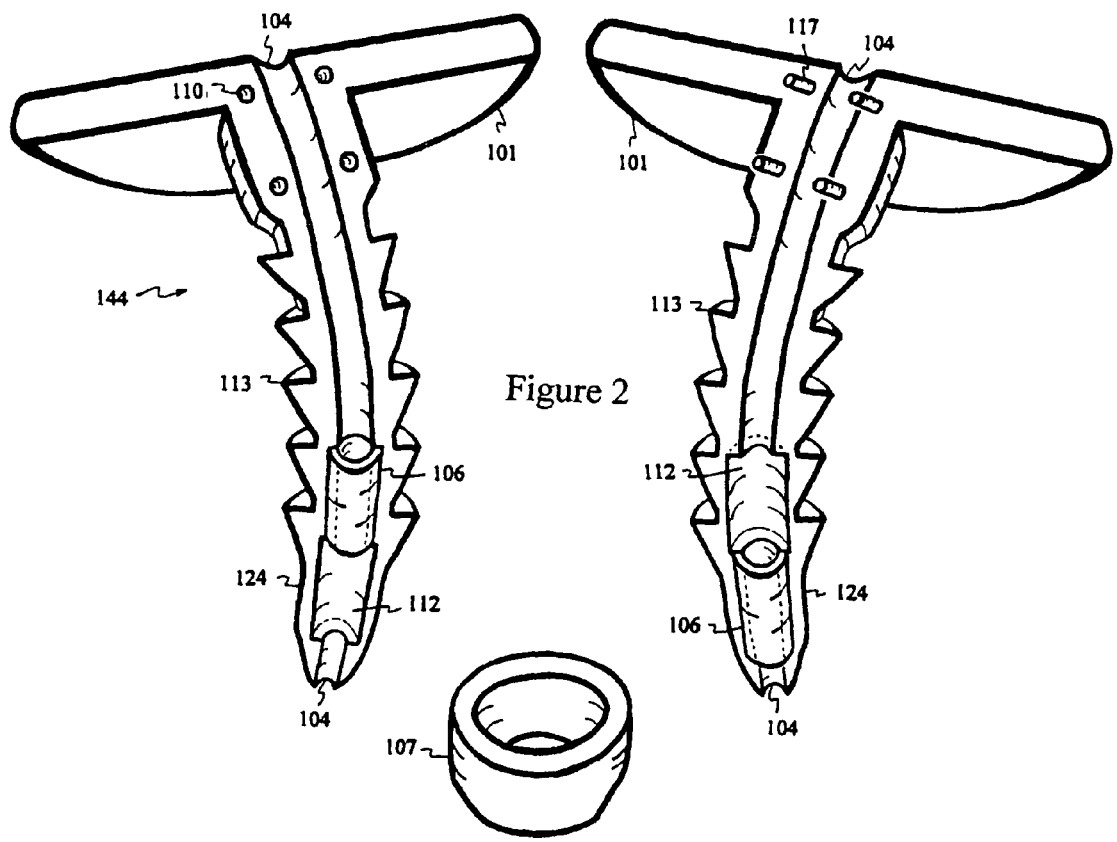
FIG. 2 depicts the interior of the curved pieces with trocar retainers 106 arching over, and indentations 112 dipping beneath the longitudinal troughs 104.

The inner dimension of a ring 107 or assembly retainer, as shown in FIG. 1, is sized and configured to fit around the neck 116 region of the elastic pieces. FIG. 2 depicts the interior sides of the components with trocar retainers 106 arching over the longitudinal troughs 104 adjacent to indentations 112 in the troughs 104. The arching retainers 106 enclose over portions of the troughs 104 to fit a trocar 103. The peg holes 110 on the left elastic piece are positioned, sized, and configured to fit or house the pegs 117 on the right elastic piece.

FIG. 3 shows assembly of the pegs 117 into the holes 110 by placing the interior sides of the left and right pieces together. Connection between the pegs 117 and holes 110 prevents slippage between the pieces and aligns the retainers 106 over the indentations 112. By compressing or closing the elastic legs 124 with an external force, the trocar retainer 106 of the right piece fits into the indentation 112 of the left piece and vice versa. In the closed position, the legs 124 are resiliently joined or straightened; the two semi-cylindrical troughs 104 are also joined together to form a cylindrical lumen 104. Furthermore in the closed position, the ring 107 can slide over the gripping elements 113 onto the neck 116, as shown in FIG. 4. Working in conjunction with the planted pegs 117, the tightly fitted ring 107 on the neck 116 prevents separation between the left and right pieces and retains the pegs 117 within the holes 110 to secure the assembled tack fastener 144. The head 101 and neck 116 regions can also be welded or glued together, without using the ring 107. If the external force were released, the elastic legs 124 would spread out, reestablishing the open, curved, deployed or predisposed position, as shown in FIG. 5.

Figure 6:
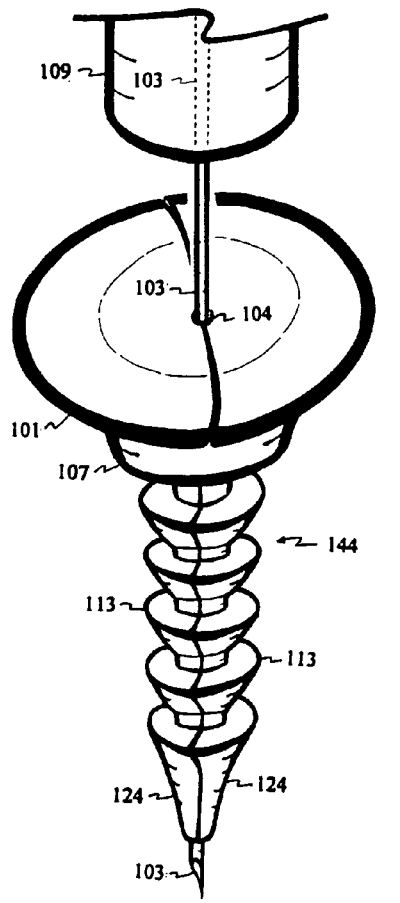
FIG. 6 depicts a trocar 103 inserted into the lumen 104 of the tack fastener 144. A compressive sleeve 109 is loosely fitted over the trocar 103, positioned to press the tack fastener 144 into tissue.
Figure 7:
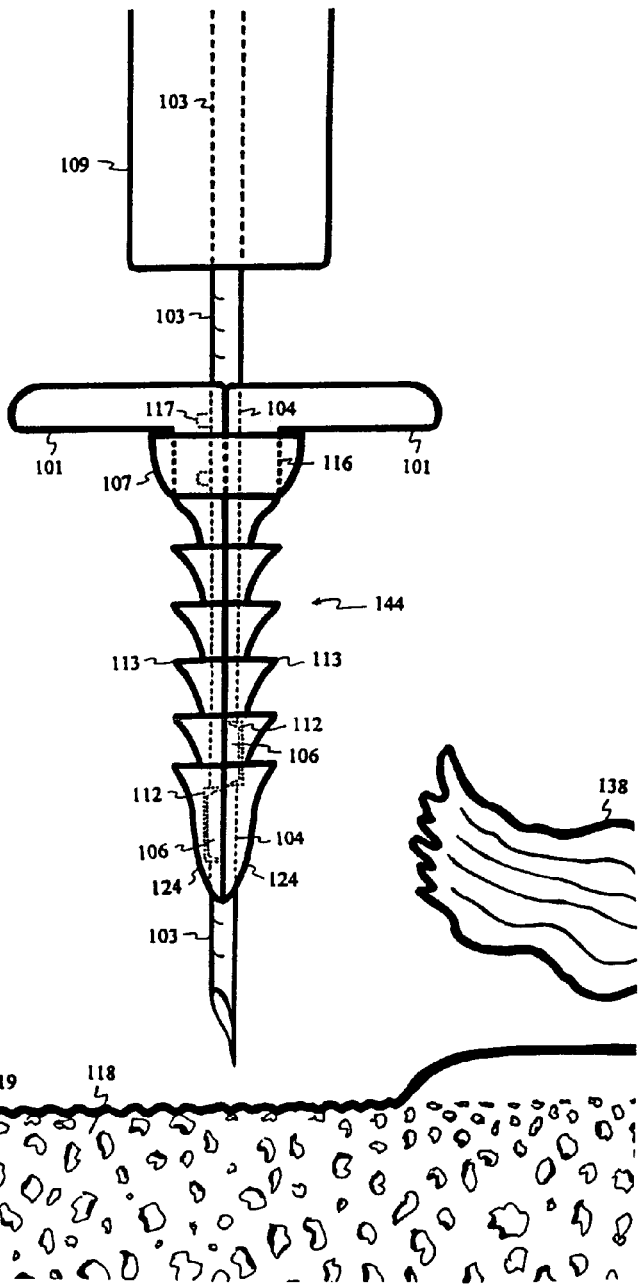
FIG. 7 shows a side view of the trocar 103 inserted into the lumen 104 through both trocar retainers 106 to keep the resilient legs 124 from spreading open.

With the external force still straightening the legs 124, a trocar or a needle 103 is inserted into the lumen 104 from the head 101 and threaded through both retainers 106 and out past the distal ends of the legs 124, as shown in FIGS. 6 and 7. FIG. 7 shows a side view of the trocar 103 inserted into the lumen 104 through both trocar retainers 106 to restrict the elastically curved legs 124 from spreading open. In essence, the trocar 103 serves as a removable linkage holding or latching the trocar retainers 106 of the expandable tack fastener 144 in a closed, delivery or straightened position. To optimize resilient closure or straightening of the legs 124, both retainers 106 are preferred to be located near the distal ends of the legs 124, as shown in FIG. 7. The retainers 106 are also preferred to be positioned adjacent to each other to minimize bending of the trocar 103 by the opening forces of the elastic legs 124. Friction between the restrained retainers 106 and trocar 103 keeps the tack fastener 144 from sliding off the trocar 103. Beyond the distal ends of the closed legs 124, the protruding sharp tip of the trocar 103 spearheads tissue puncturing. A compressive sleeve 109 is loosely fitted over the trocar 103 as part of the delivery device for pressing the expandable tack fastener 144 into tissue. For a small surgical field and uneven surgical surface, the underside of the head 101 of the expandable fastener 144 can be contoured to fit over the tissue to be fastened. To avoid rotation of the tack fastener 144 around the trocar 103 during delivery, the lumen 104 of the tack fastener 144 and cross section of the trocar 103 can also be made non-round to improve control and precision for delivery. FIG. 7 also shows a torn and detached ligament 138 over a burred or decorticated cancellous bone 118.

Figure 8:
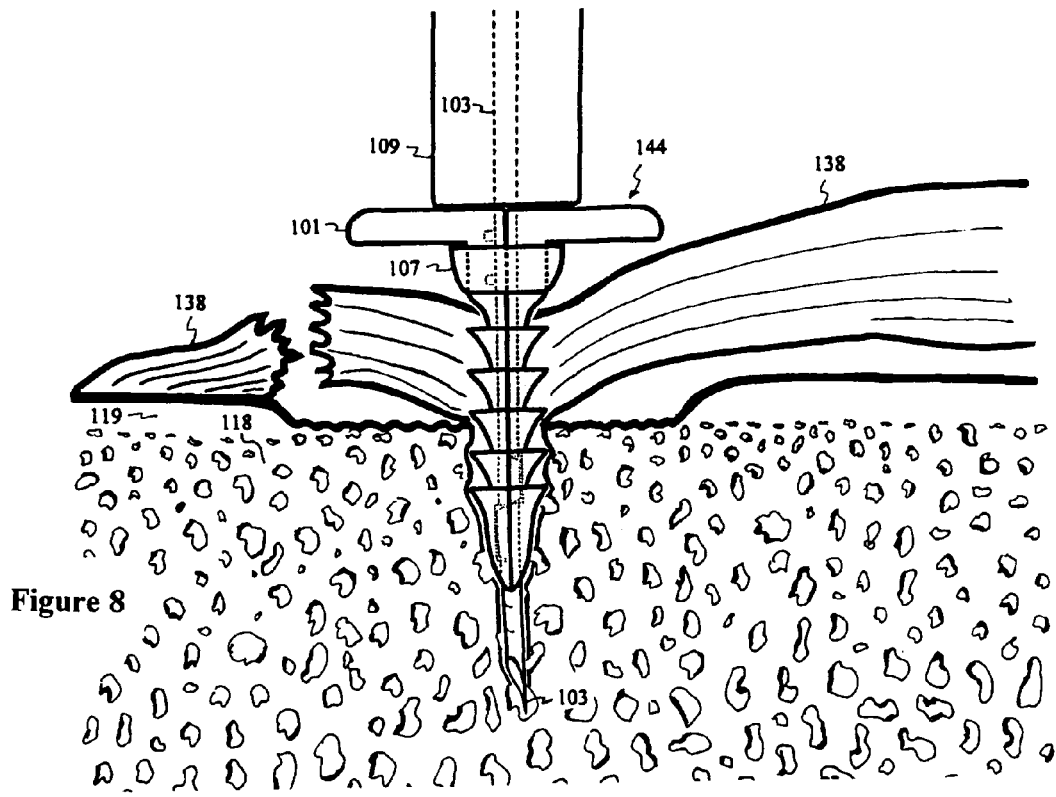
FIG. 8 depicts puncturing of the trocar 103 through a torn ligament 138 into bone 118, followed by compressive sleeve 109 pressing the tack fastener 144 into bone 188.
Figure 9:
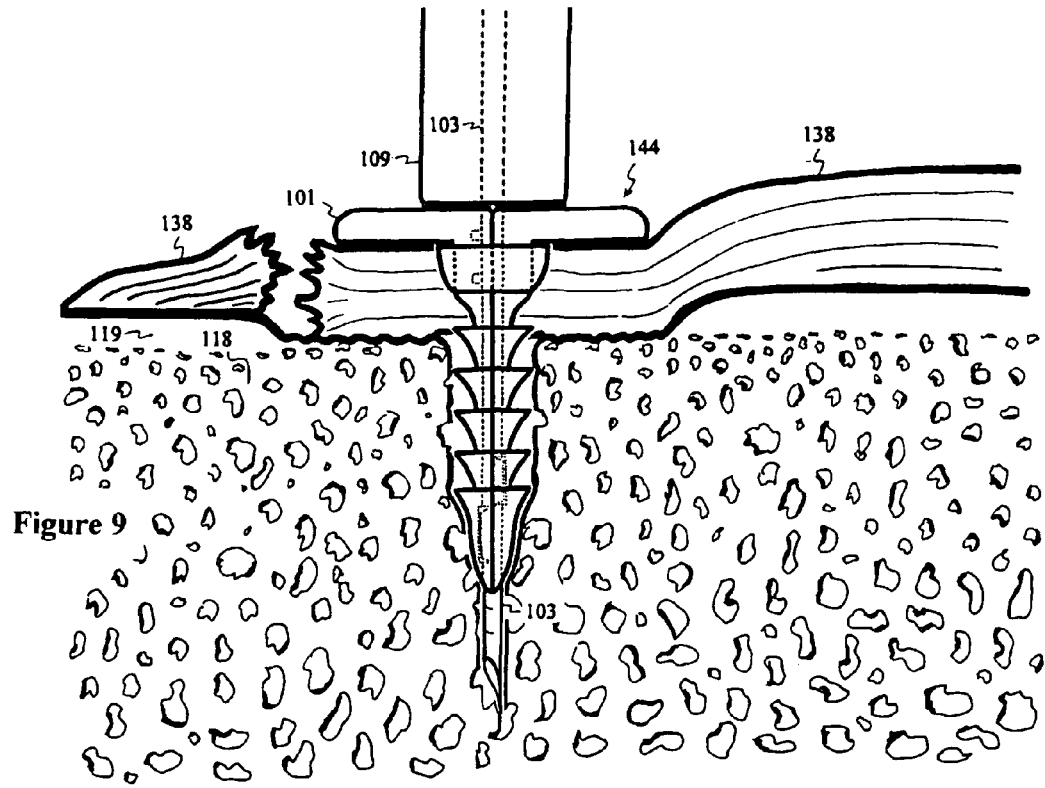
FIG. 9 shows tacking of the torn ligament 138 by pressing the tack fastener 144 into the bleeding cancellous bone 118.
Figure 10:
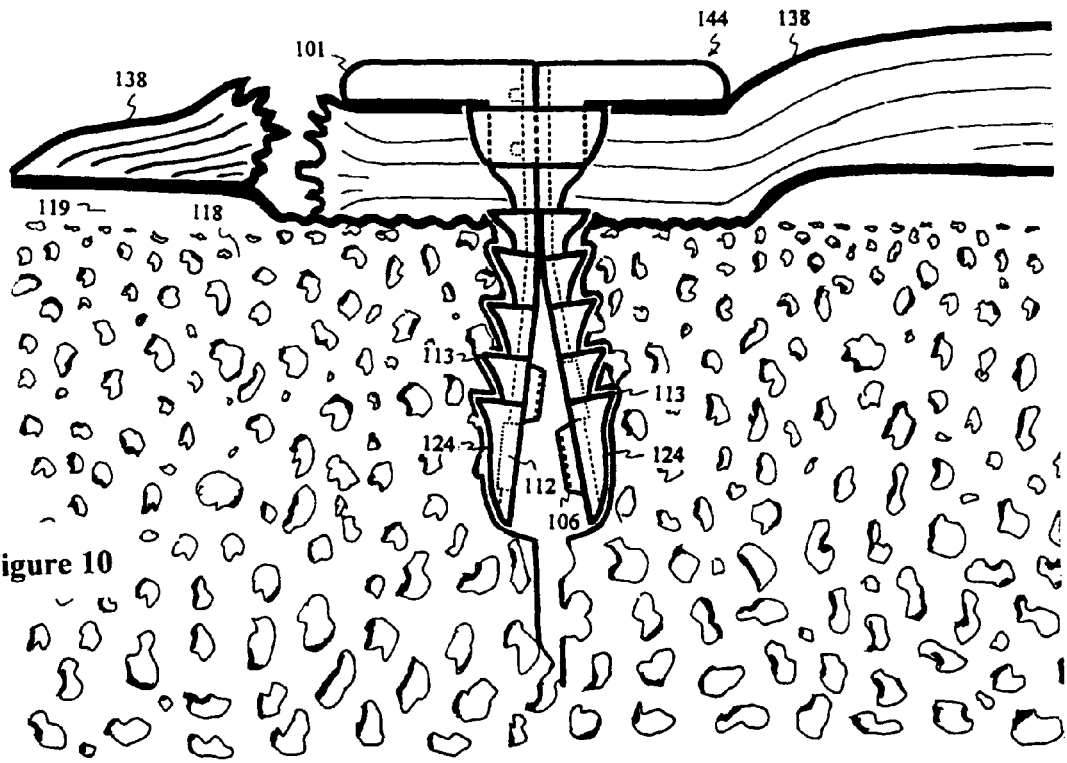
FIG. 10 depicts trocar 103 withdrawal and elastic opening of the legs 124 to laterally press and fasten the gripping elements 113 into the porous bone 118.
Figure 11:
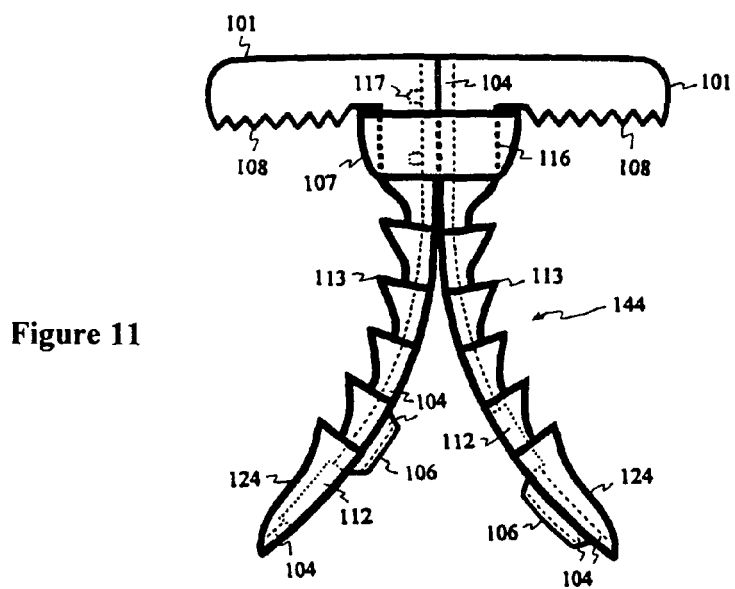
FIG. 11 shows an expandable tack fastener 144 with tack grips 108 on the underside of the head 101 to improve gripping power upon the ligament 138 or tacked tissue.

FIG. 8 shows an initial trocar 103 puncture through a torn ligament 138 into bleeding cancellous bone 118, followed by compression of the sleeve 109 to deliver the straightened legs 124 of the expandable tack fastener 144 through the ligament 138 into the cancellous bone 118. FIG. 9 shows tacking of the torn ligament 138 with the head 101 and securing of the legs 124 with gripping elements 113 into the bleeding cancellous bone 118. As the trocar 103 is withdrawn while compression of the sleeve 109 continues, the trocar restrainers 106 are no longer linked or bound together. Thus the legs 124 resiliently or elastically open, pressing the gripping elements 113 outwardly to fasten onto the porous cancellous bone 118, as shown in FIG. 10. To prevent jamming between the retainer 106 and the indentation 112 or between the retainers 106, which would hinder the legs 124 from opening after withdrawal of the trocar 103, both distal and proximal ends of the retainers 106 are tapered, as shown in FIGS. 5 and 10. The compressive sleeve 109 is then withdrawn from the expanded tack fastener 144. The outward anchoring of the gripping elements 113 is elastic and continuously embeds and fastens into the tissue. The interface between the reattached ligament 138 and the bleeding bone 118 will likely formed an adhesion, thus favoring permanent ligament reattachment to bone 118. Therefore, the expandable tack fastener 144 can be made with biodegradable material, which slowly degrades after the healing is complete. FIG. 11 shows a tack fastener 144 with tack grips 108 at the underside of the head 101 to minimize movement of the tacked tissue, perhaps improving the healing rate of the tacked ligament 138 or tissue. The shape of the head 101 can also be modified to fit over the fastened tissue.

Outward anchoring is most intense at the distal ends of the legs 124, gradually decreasing toward the proximal ends to provide anchoring strength along the entire length of the legs 124 of the expandable tack fastener 144. The anchoring or fastening space created in the tissue between the curved legs 124 of the tack fastener 144 is cone-shaped, large at the base and small toward the surface, as indicated in FIG. 10. In essence, the legs 124 of the deployed tack fastener 144 elastically flare open to establish a cone-shaped anchoring space within the tissue. The formation of the conical space alone within tissue would oppose pull out. Combined with the fastening of the outward pressing gripping elements 113 against the tissue within the conical space, the anchoring strength is expected to be exceptionally high. The outwardly opening legs 124 of the expandable tack fastener 144 may be sufficient to anchor within osteoporotic bone or mushy tissue, whereas other anchors or suture may fail.

The tack fastener 144 may able to be delivered without the sliding compressive sleeve 109. When the resiliently straightened legs 124 are inserted into the tissue, the tightness of the insertion provides some restriction upon the straightened legs 124, keeping the legs 124 together, as indicated in FIG. 9. As a result, the friction between the trocar 103 and the retainers 106 substantially decreases, while the legs 124 are bound and surrounded by tissue. Furthermore, the gripping elements 113 of the legs 124 snag onto the tissue, allowing the trocar 103 to withdraw and dislodge the tack fastener 144, possibly without holding the compressive sleeve 109 against the head 101. The trocar 103 can be modified by adding a step with a larger diameter to prevent the fastener 144 from sliding up and provide compression against the head 101 of the tack fastener 144 during delivery. The trocar 103 can also contain markers to indicate depth of insertion or penetration.

The expandable tack fastener 144 can be shaped to function as an expandable screw. FIG. 12 shows another assembled three-piece screw fastener 284 with self-tapping threading as gripping elements 113. The screw fastener 284 also contains a lumen 104, trocar retainers 106 and indentations 112 in the elastically curved legs 124. The top of the head 101 contains a Phillips cross slot 228. The interior surfaces of the separated pieces have tongues 168 and grooves 169, as shown in the top view in FIG. 13, which prevent twisting between the pieces during tightening of the screw fastener 284. Other types of slots 228 for advancing the screw fastener 284 are possible. FIG. 14 shows the fit between the tongues 168 and grooves 169 held together by the ring 107, as shown in FIG. 12. The lumen 104 extends from the bottom of the Phillips slot 228 to the distal end of the screw fastener 284. FIG. 15 shows a trocar 103 protruding from the tip of a Phillips screw driver 133. The proximal end of the Phillips screw driver 133 contains screw thread 236 for tightening into a removable handle 174. In FIG. 16, the elastically curved legs 124 of the screw fastener 284 are straightened into a closed position. The trocar 103 is inserted from the head 101 into the lumen 104, through both trocar retainers 106 to restrict the legs 124 from elastically opening, then out through the distal end of the screw fastener 284. Insertion of the trocar 103 also helps to guide and position the driver 133 into the Phillips slot 228 to advance the screw fastener 284.

Figure 17:
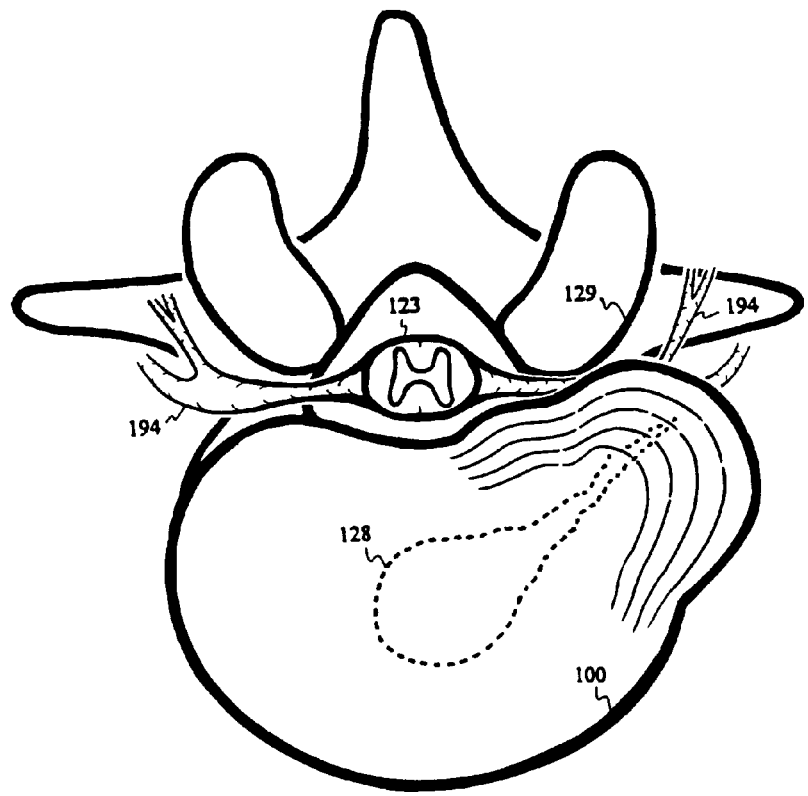
FIG. 17 depicts a bulging disc 100 impinging upon a nerve root 194.
Figure 18:
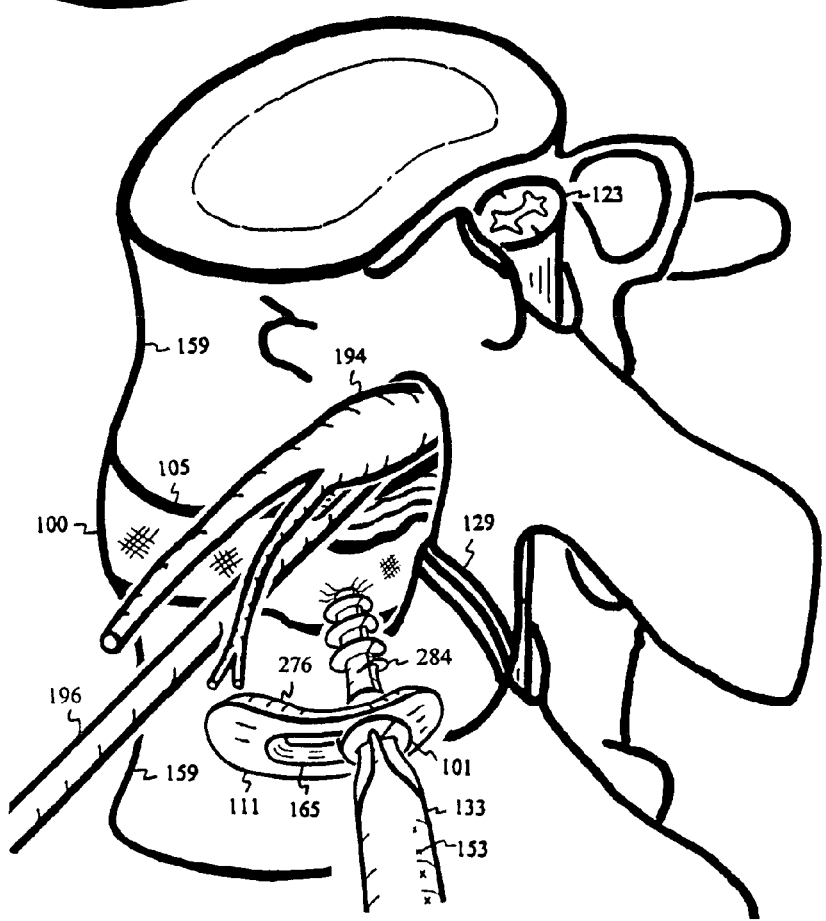
FIG. 18 shows the screw fastener 284 holding a disc compressor 111 while advancing into the bulging disc 100.
Figure 19:
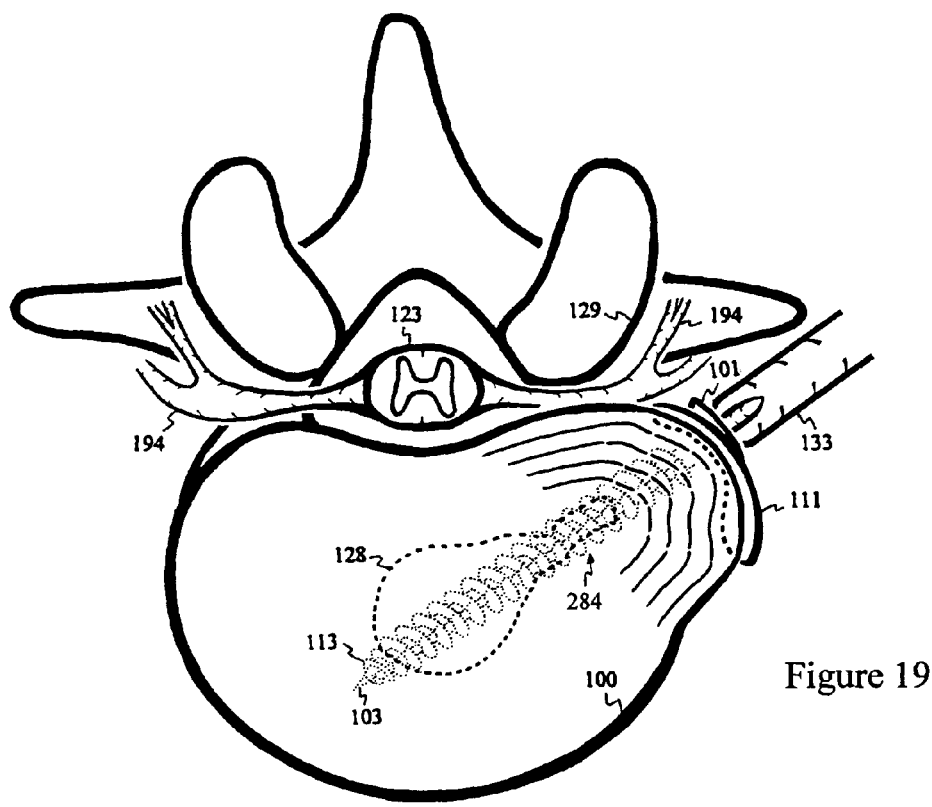
FIG. 19 shows bulge compression by the disc compressor 111 as the screw fastener 284 advances into the disc 100.
Figure 20:
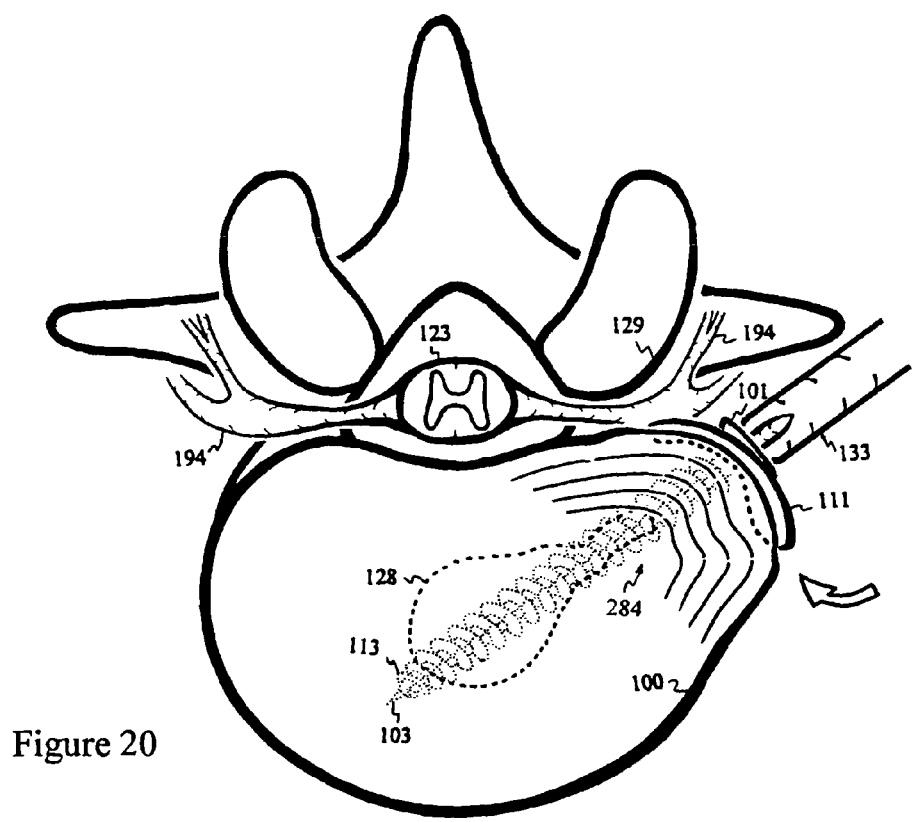
FIG. 20 depicts medial repositioning of the disc compressor 111 toward the neuroforamen after initial bulge compression.
Figure 21:
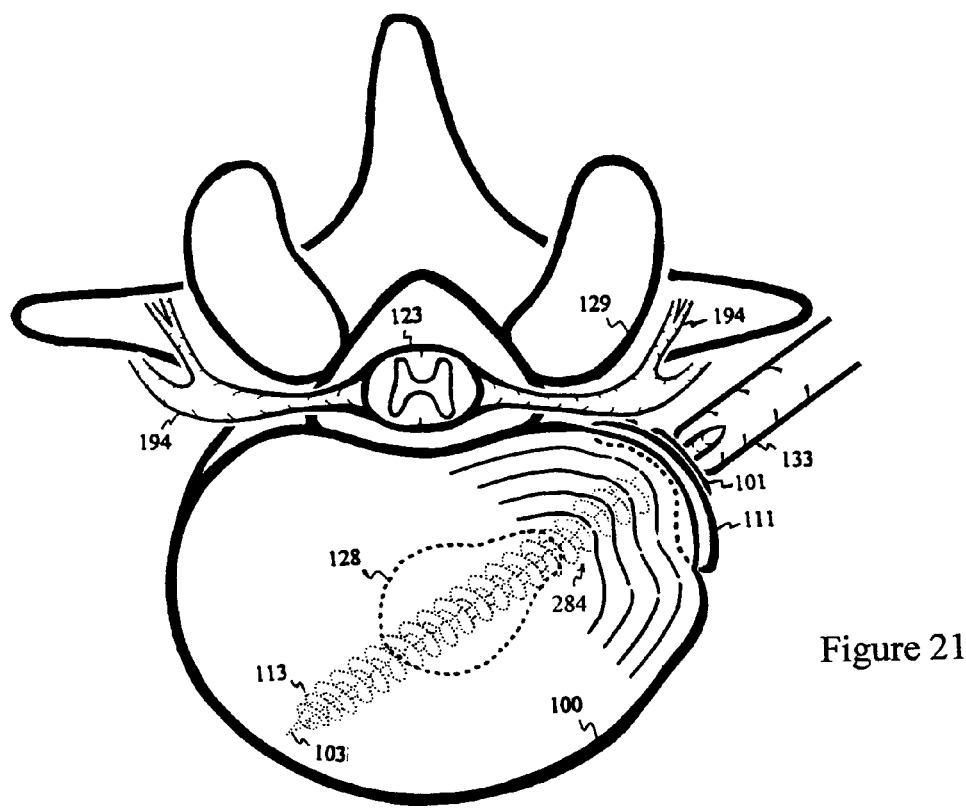
FIG. 21 shows further advancement of the screw fastener 284 into the disc 100 by pressing in a large section of bulging anulus to free the nerve 194 from impingement.
Figure 22:
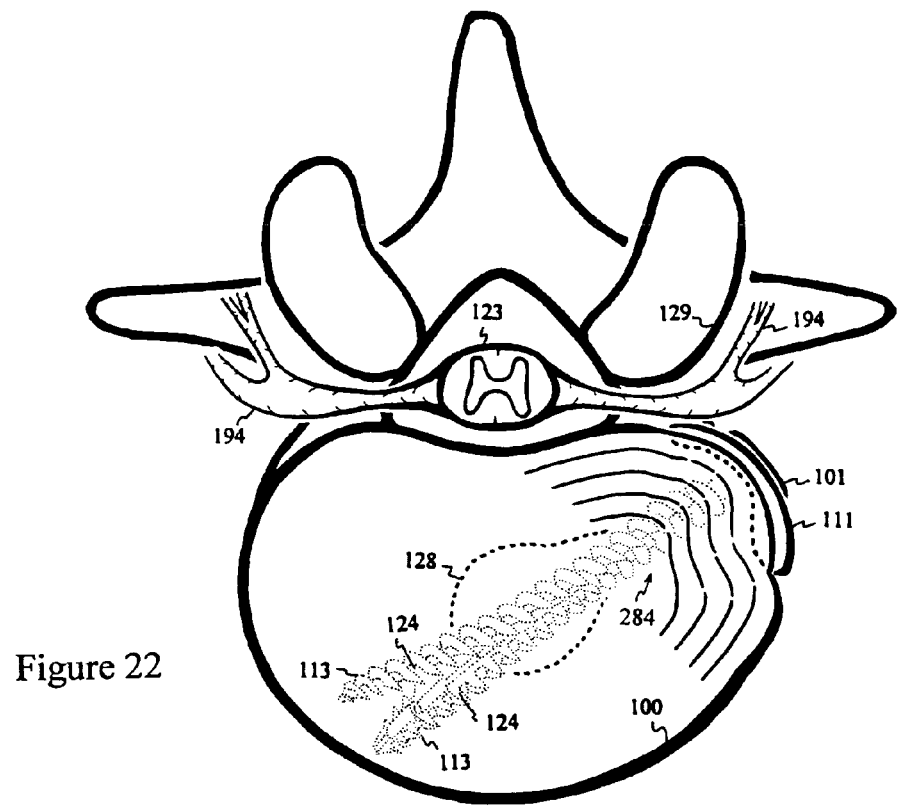
FIG. 22 depicts anchoring of the open legs 124 in the distal anulus to fasten the proximal bulge following withdrawal of the trocar 103 and driver 133.

FIG. 17 depicts a common nerve 194 impingement at the neuroforamen around the facet joint 129. FIG. 18 shows the screw fastener 284 inserted through an elongated opening 165 of a disc compressor 111 and advanced into the bulging disc 100. The disc compressor 111 is designed to allow lateral adjustment with the elongated opening 165 for the screw fastener 284. For the comfort of the patient, the opening direction of the legs 124 is preferred to be in the plane of the disc 100, rather than opening and pressing toward the end plates 105 of vertebral bodies 159. A marker 153 on the driver 133 is aligned with the opening gap of the screw fastener 284 to identify the direction of leg 124 expansion. FIG. 19 shows advancement of the screw fastener 284 through the nucleus pulposus 128 into the distal anulus of the disc 100 to compress the bulge with the compressor 111. The bulge compression opens up the neuroforamen to allow lateral to medial manipulation, positioning of the disc compressor 111 toward the neuroforamen, as shown in FIG. 20. The screw fastener 284 is further advanced into the disc 100 to free the nerve 194 impingement by pressing in a large section of the bulging anulus, as shown in FIG. 21. The trocar 103 with Phillips driver 133 is then withdrawn, allowing the unrestricted legs 124 of the screw fastener 284 to resume their curvatures, pressing and anchoring the gripping elements 113 into the relatively healthy and secured distal anulus, as shown in FIG. 22. As a result, the bulging anulus is compressed and fastened to alleviate nerve 194 impingement. The compression and fastening of the bulging anulus may also collapse and seal leaking channels of the viscous nucleus pulposus 128 that cause neural irritation. The disc compressor 111 and the screw fastener 284 can be made with biodegradable material to treat nerve 194 impingement. As the degenerated anulus is compressed and metabolized, concurrently new anulus is shaped and formed under the compressor 111. After the disc 100 is healed, both the compressor 111 and screw fastener 284 then degrade to avoid possible device migration with time.

Figure 23:
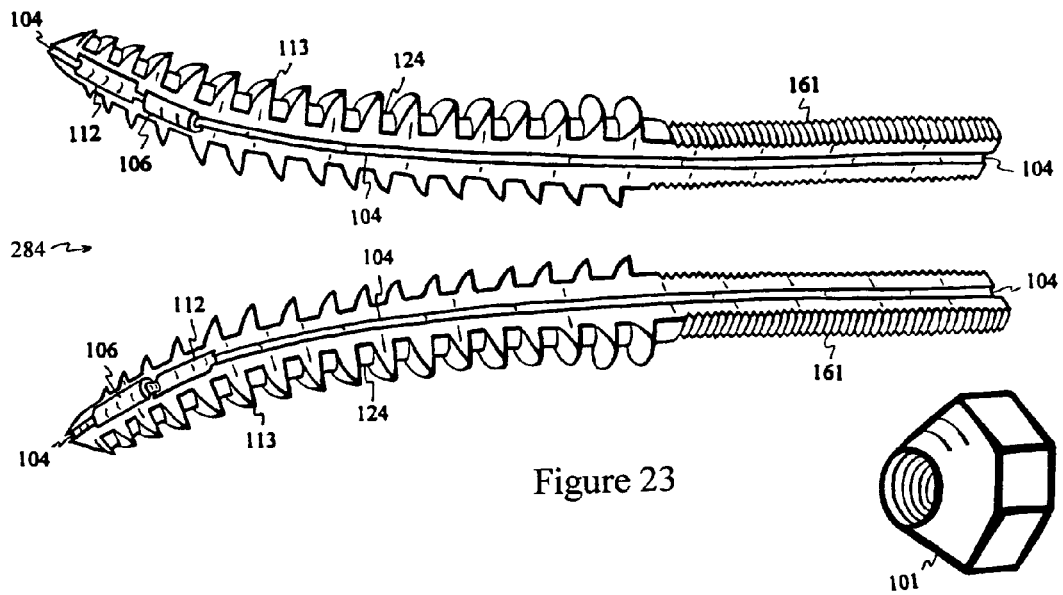
FIG. 23 shows another three-piece fastener 284 with a threaded portion 161 attachment and a nut 101.
Figure 24:
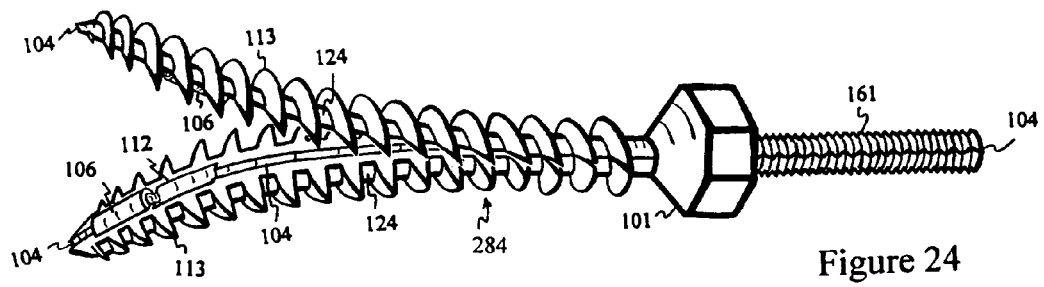
FIG. 24 shows the assembled fastener 284 tightened by the nut 101 over the threaded portion 161.
Figure 25:
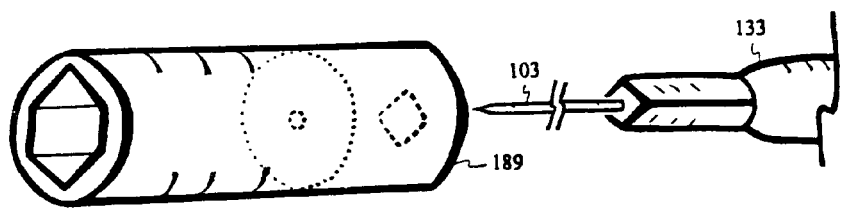
FIG. 25 depicts a socket 189 and a trocar 103 protruding from the tip of a socket driver 133.
Figure 26:
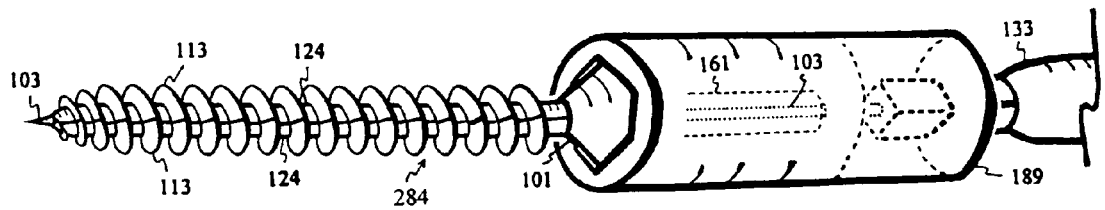
FIG. 26 shows trocar 103 inserted through the lumen 104 holding both retainers 106, shown in FIG. 24, to keep the legs 124 from resiliently spreading apart.

FIG. 23 shows another screw fastener 284 having two elastically curved pieces with lumens 104, retainers 106, indentations 112, gripping elements 113 and semicylindrical threaded proximal portions 161. As the curved pieces join together, the threaded proximal portions 161 form a cylindrical threaded portion 161. A nut with internal thread, sized to engage the cylindrical threaded portion 161, is used as head 101 of the screw fastener 284. FIG. 24 shows the assembled screw fastener 284 tightened by the nut-like head 101 over the cylindrical threaded portion 161. FIG. 25 shows a socket 189 and a trocar 103 protruding from the tip of a socket driver 133. The elastically curved legs 124 are resiliently straightened, prepared for trocar 103 insertion. Sequentially, the trocar 103 enters through the socket 189, into the lumen 104 of the straightened fastener 284 and through the retainers 106 to bind the legs 124 in a straightened or closed position, and then protrudes out the distal end of the assembled fastener 284. The trocar 103 insertion also guides the driver 133 to the socket 189 and the socket 189 over the nut-like head 101, as shown in FIG. 26.

The screw fastener 284 with the threaded proximal portion 161 attachment and round contour of the nut-like head 101 is designed to be used as a pedicle screw. In a closed position, the expandable screw fastener 284 is advanced into the vertebral body 159 with the socket 189 and driver 133. The trocar 103, socket 189 and driver 133 are then withdrawn to allow the legs 124 to resume the open position, pressing and fastening the gripping elements 113 into the vertebral body 159, as shown in FIG. 27. Additional instrumentation for spinal fusion will be attached to the threaded proximal portion 161, then fastened with another nut, which will further-secure the assembly of the screw fastener 284 within the vertebral body 159. Expandable fastening can be particularly useful in poor quality bone.

To prevent lateral slippage between the legs 124 of the screw fasteners 284, as shown in FIGS. 12 and 24, during rotational tightening of the fastener 284 in the tissue, tongues 168 and grooves 169 can be incorporated longitudinally along both legs 124. The longitudinally oriented tongues 168 and grooves 169 along the adjoining surfaces of the legs 124 are shown in cross-sectional view in FIG. 28. In the closed position, the tongues 168 are entrenched in the grooves 169, as shown in a cross-sectional view in FIG. 29.

Figure 31:
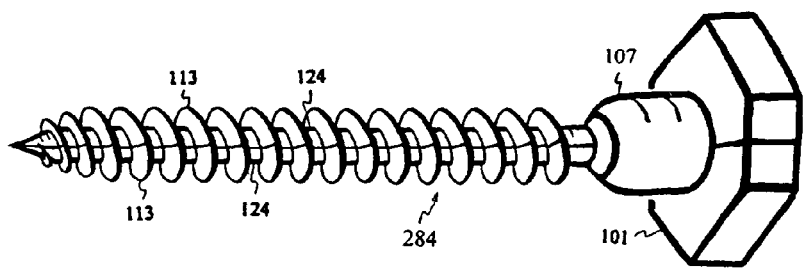
FIG. 31 shows the legs 124 of the screw fastener 284, shown in FIG. 30, glued and bound by a water degradable adhesive.
Figure 32:
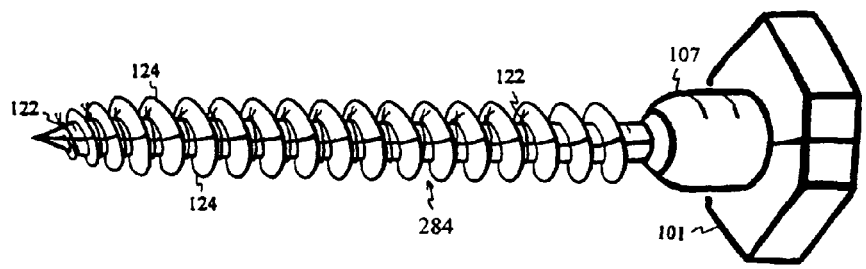
FIG. 32 shows that the legs 124 of the screw fastener 284, shown in FIG. 30, are externally tied or bound with degradable sutures 122 or band.

Expansion of the screw fastener 284 or spreading of the legs 124 can be controlled without the trocar 103, lumen 103, retainers 106 and indentations 112. The interior sides or adjoining surfaces of the elastically curved legs 124, as well as the heads 101 and necks 116, contain matching tongues 168 and grooves 169, as shown in FIG. 30. The adjoining surfaces of the curved pieces are glued and bound with a water degradable or soluble adhesive, while the ring 107 retains the tongue 168 in the groove 169 at the head 101 and neck 116 regions to hold the screw fastener 284 together, as shown in FIG. 31. Welding or gluing with a water insensitive adhesive can also join the heads 101 and necks 116 of the elastic pieces without using the ring 107. After the screw fastener 284 is installed in tissue, the adhesive slowly degrades by blood serum, allowing the legs 124 of the fastener 284 to spread open and further fasten into tissue. The curved legs 124 can also be tied or bound together with degradable sutures 122, as shown in FIG. 32, or with other degradable material.

Figure 33:
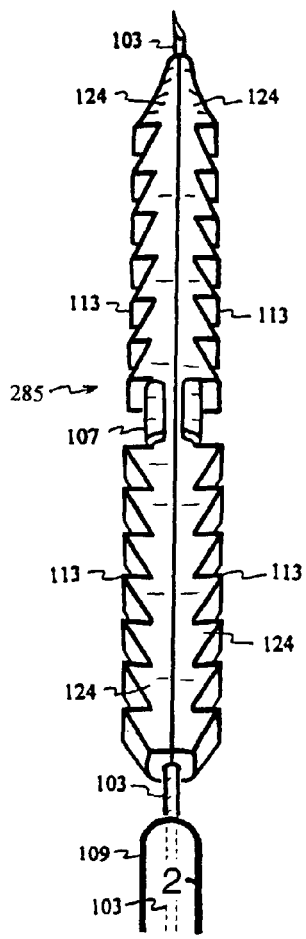
FIG. 33 depicts a counter-gripping fastener 285 with four elastic legs 124 resiliently straightened by a trocar 103.
Figure 34:
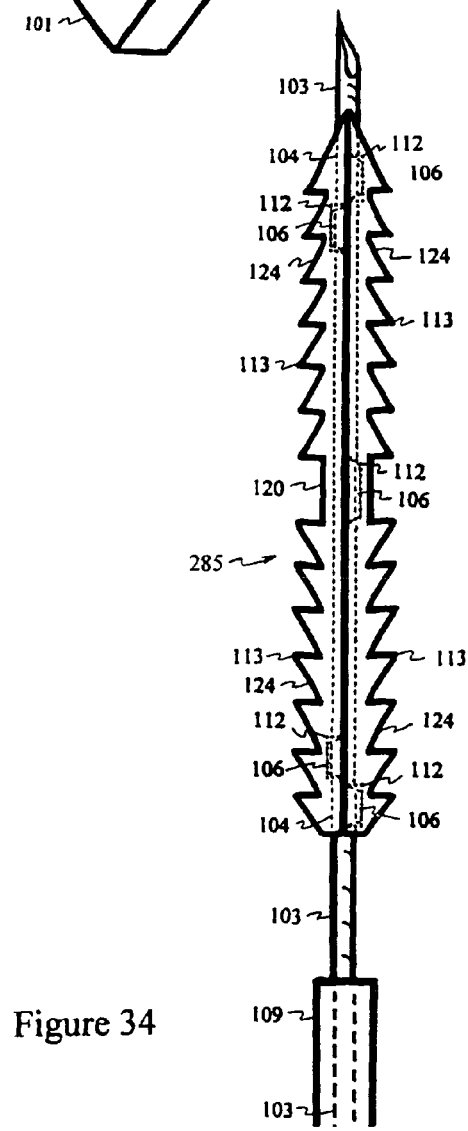
FIG. 34 depicts a mid-longitudinal view of the fastener 285, as shown in FIG. 33, with the trocar 103 linking the retainers 106 to keep the elastic legs 124 from opening.

Expandable fastener can also approximate and repair torn tissue by counter fastening. FIG. 33 depicts an elastic counter fastener 285 with four legs 124 resiliently straightened by a trocar 103 with a compressive sleeve 109. Similar to the expandable tack fasteners 144 mentioned, each leg 124 contains an indentation 112 adjacent to a retainer 106 for linking onto the trocar 103, as shown in a mid-longitudinal view in FIG. 34. FIG. 35 shows two major pieces forming four elastically curved legs 124 with the trocar retainers 106 positioned, sized and configured to fit and match the indentations 112 on the adjoining piece. Both the indentation 112 and retainer 106 are preferred to be near the tip of each leg 124 to ensure adequate closure of the legs 124. The direction of the gripping elements 113 at the distal halves oppose the direction of the elements 113 at the proximal halves of the counter-gripping fastener 285. The gripping elements 113 at the distal halves of the fastener 285 oppose pulling, while the gripping elements 113 at the proximal halves oppose pushing. The distal and proximal groups of gripping elements 113 are separated by a counter junction 120. Within the counter junction 120, a retainer 106 is embedded in an indentation 112 like tongue and groove, as shown in FIGS. 34 to 36. The two-piece elastic fastener 285 is then tied and fastened by a ring 107 or a restricting member over the counter junction 120, as shown in FIG. 33, to keep the retainer 106 in the indentation 112 and hold the mid-section of the counter-gripping fastener 285.

The needle 103 and compressive sleeve 109 are used in conjunction to deliver and deploy the counter-gripping fastener 285. The needle 103 carrying the fastener 285, as shown in FIG. 33, punctures into a torn tissue to deliver the distal half of the fastener 285 through the tear 139, and places the counter junction 120 at the tear 139. In essence, the counter-gripping fastener 285 is bridging the torn tissue, over the tear 139. To deploy the counter-gripping fastener 285, the compressive sleeve 109 proximal to the fastener 285 is held stationary while the needle 103 is withdrawn. This allows the legs 124 to curve outwardly, as shown in FIG. 36, pressing the gripping elements 113 into tissue at both distal and proximal sides of the tear 139. FIG. 37 depicts a portion of a meniscus 135 with a tear 139. The fasteners 285 are delivered with counter junctions 120 positioned at or near the tear 139 of the meniscus 135. The needle 103 is then withdrawn from the puncture site 121 to allow both the distal and proximal legs 124 to counter-fasten the torn tissue, as shown in FIG. 38. The counter-gripping fastener 285 is totally hidden within the repaired meniscus 135 with no protrusion to scrape, scratch or damage the delicate articular surface of the joint. Counter-fastening of the expandable fastener 285 is made possible by the opposing directions of the gripping elements 113 at the distal and proximal portions of the fastener 285 to rejoin or approximate the torn tissue for healing.

The counter fastener 285 may able to be delivered without the sliding compressive sleeve 109. As the resiliently straightened legs 124 are inserted into tissue, tightness of the insertion provides restriction upon the straightened legs 124, keeping the legs 124 together. While the legs 124 are bound and surrounded by tissue, friction between the needle 103 and the retainers 106 substantially decreases. Furthermore, the gripping elements 113 of the legs 124 snag onto tissue, allowing the needle 103 to withdraw and dislodge the fastener 285 perhaps without holding the compressive sleeve 109 over the proximal end of the fastener 285 during needle 103 withdrawal. The needle 103 can be modified with a step, formed by an enlarged diameter, to provide compression onto the fastener 285 during delivery without the compressive sleeve 109. The needle 103 can also contain markers to indicate depth of penetration.

Figure 39:
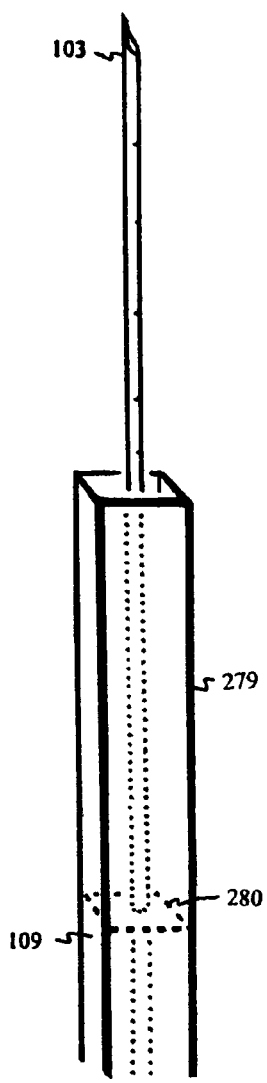
FIG. 39 depicts a sleeve 279 extending from the distal end 280 of a compressive sleeve 109.
Figure 40:
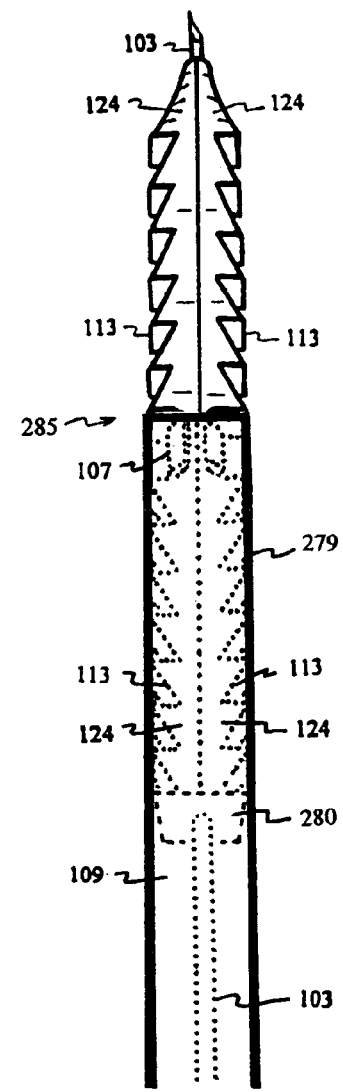
FIG. 40 shows the proximal legs 124 of the counter-gripping fastener 285 housed within the sleeve 279 to ease tissue insertion.

During tissue puncturing, the proximal gripping elements 113 of the counter-gripping fastener 285 may snag onto the tissue. Therefore, a sleeve 279 can be used to cover the proximal legs 124, shielding the gripping elements 113 from tissue snagging during insertion. The sleeve 279 can be an extension from the distal end 280 of the compressive sleeve 109, as shown in FIG. 39. To ease tissue insertion, the proximal legs 124 of the counter-gripping fastener 285 are housed within the sleeve 279 above the distal end 280 of the compressive sleeve 109, as shown in FIG. 40.

Figure 41:
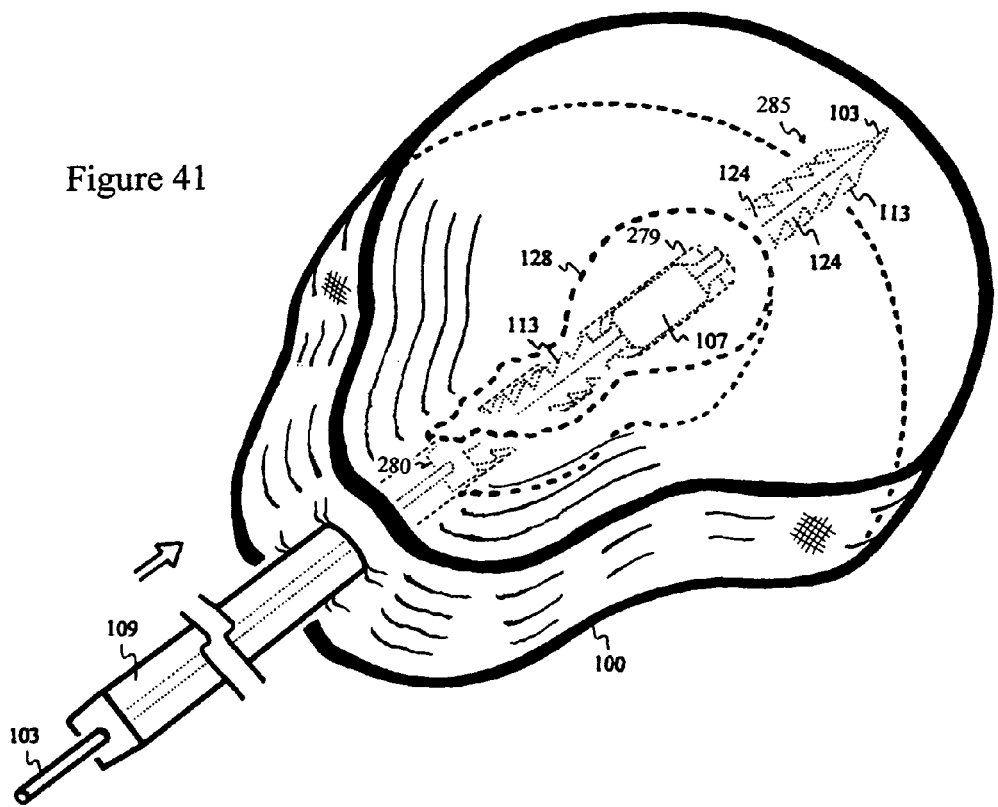
FIG. 41 depicts puncturing of the sleeve 279 covered counter-gripping fastener 285 into a bulging disc 100, spearheaded by the trocar 103.
Figure 42:
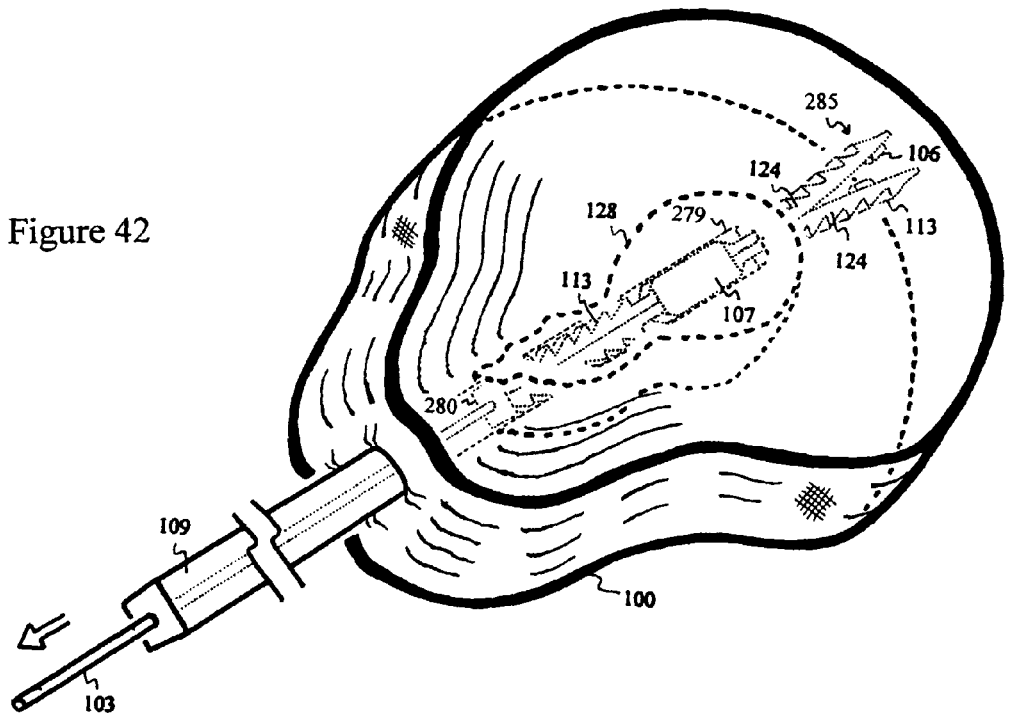
FIG. 42 shows partial withdrawal of the needle 103 to open and fasten the distal legs 124 within the distal portion of the disc 100.
Figure 43:
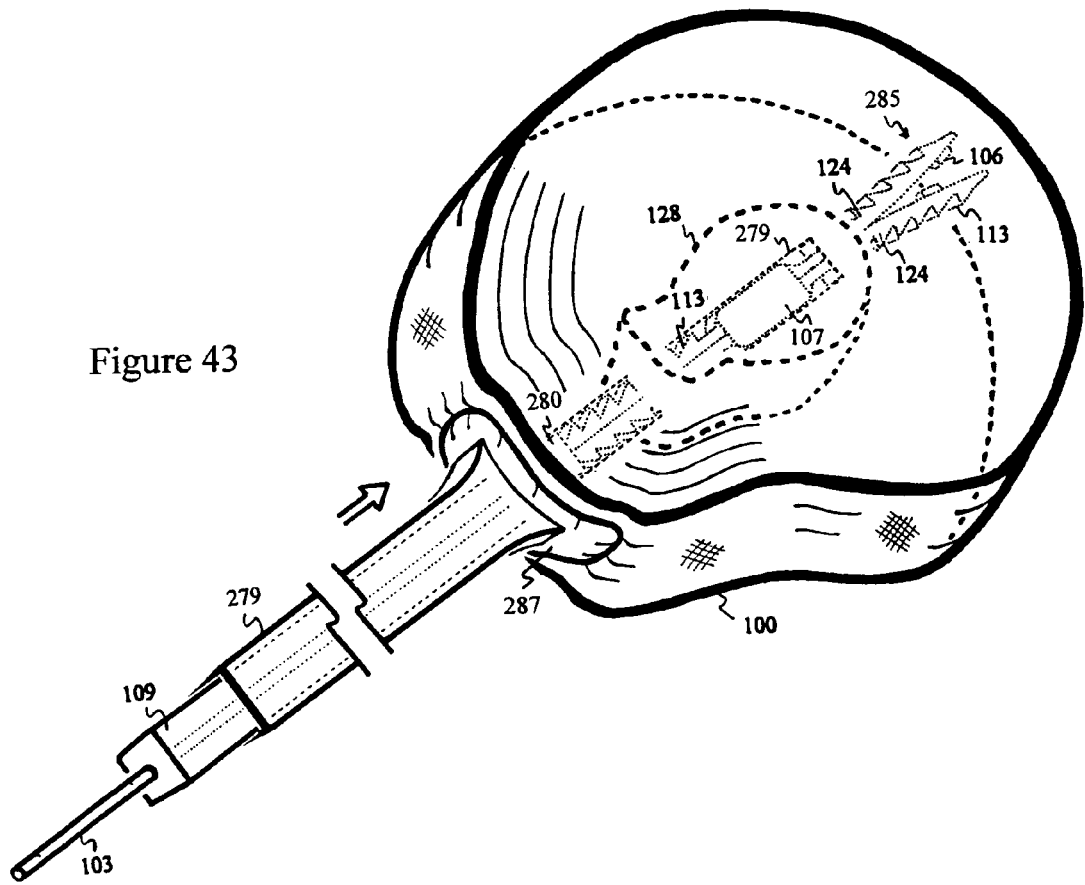
FIG. 43 depicts pushing of the bulging anulus using an outer sleeve 279 having an enlarged distal end 287.
Figure 44:
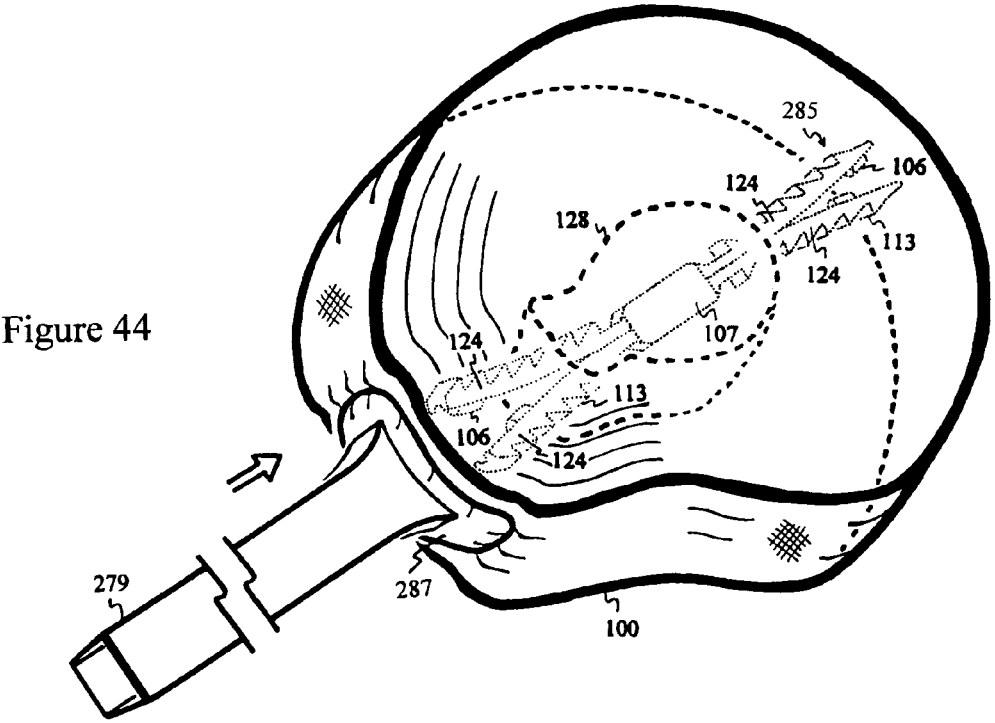
FIG. 44 shows withdrawal of both needle 103 and compressive sleeve 109, while compression of the distal end 287 continues, to open and fasten the proximal legs 124 within the compressed anulus.
Figure 45:
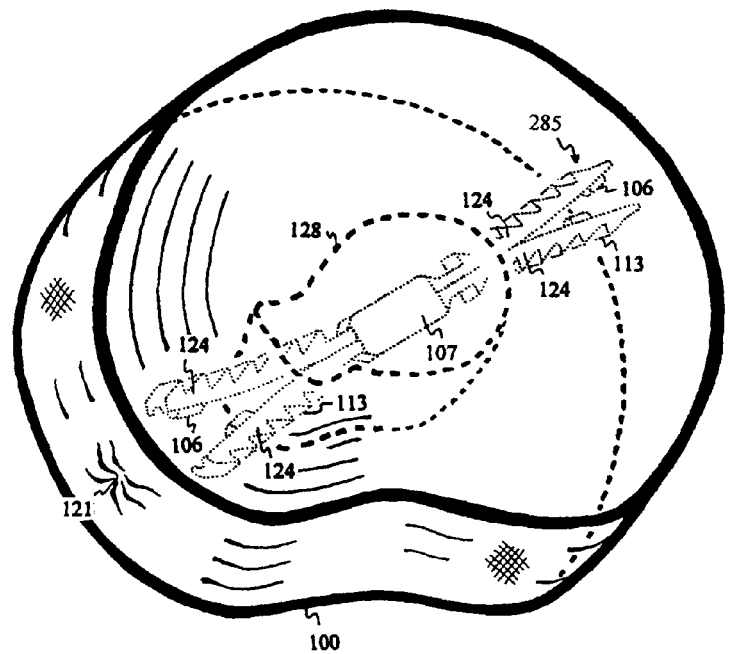
FIG. 45 depicts bulge fastening by the counter-gripping fastener 285 within the disc 100, after retrieval of the outer sleeve 279.

The counter-gripping fastener 285 can be used to repair a bulging disc 100. The sleeve 279 covered fastener 285, as shown in FIG. 40, is spearheaded by the trocar 103 as it punctures into the bulging anulus of the disc 100, as indicated in FIG. 41. The trocar 103 is partially withdrawn, allowing the distal legs 124 of the fastener 285 to open and anchor into the distal portion of the disc 100, as shown in FIG. 42. The bulging anulus is pressed inward by an outer sleeve 279 with an enlarged distal surface 287, as shown in FIG. 43, or with another instrument. While the outer sleeve 279 continues to press against the bulge, the compressive sleeve 109 then trocar 103 are withdrawn, allowing the proximal legs 124 to open, pressing the gripping elements 113 into layers of the compressed anulus, as indicated in FIG. 44. The compressed anulus is fastened or anchored by a series of gripping elements 113, holding the anulus in a non-impinging position even after compression of the outer sleeve 279 is withdrawn, as shown in FIG. 45. The counter-gripping fastener 285 is totally hidden within the repaired disc 100 with no protrusion to impinge the nerve 194. Migration of the fastener 285 is expected to be greatly minimized by the counter-gripping mechanism of the elements 113 and opening of both distal and proximal legs 124. Furthermore, the counter-gripping elements can be made with degradable material, which lasts long enough to repair the disc 100, then degrades.

Figure 46:
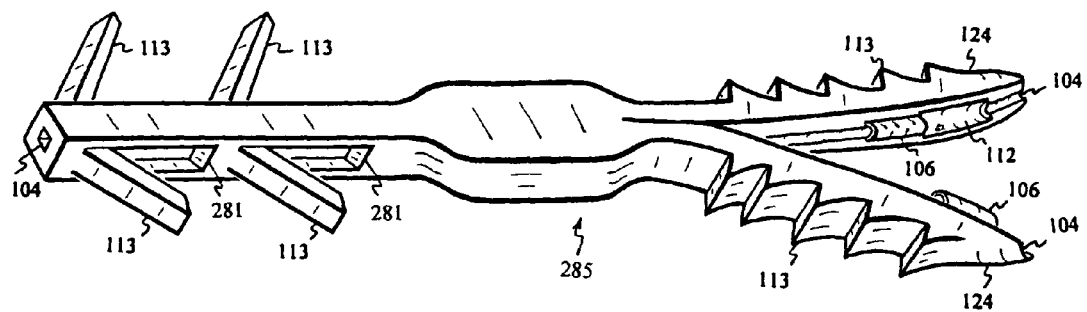
FIG. 46 shows a counter-gripping fastener 285 with distal and proximal gripping elements 113 independently operated.
Figure 47:
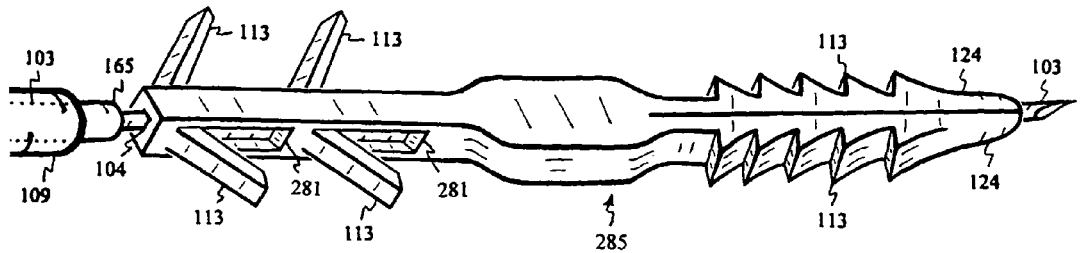
FIG. 47 depicts binding of the distal legs 124 in a closed position by a trocar 103 having a step 165 covered by a compressive sleeve 109.
Figure 48:
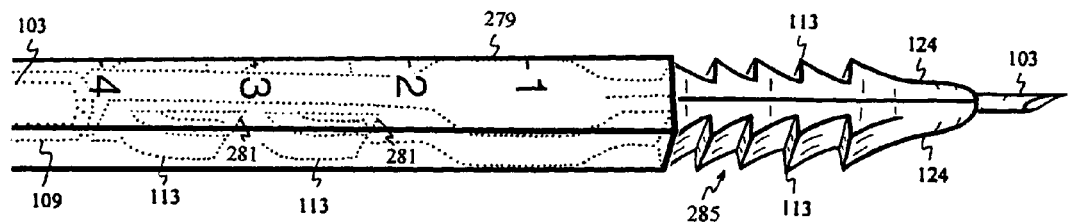
FIG. 48 depicts a sleeve 279 shielding and elastically compressing the proximal gripping elements 113 in a closed position.
Figure 49:
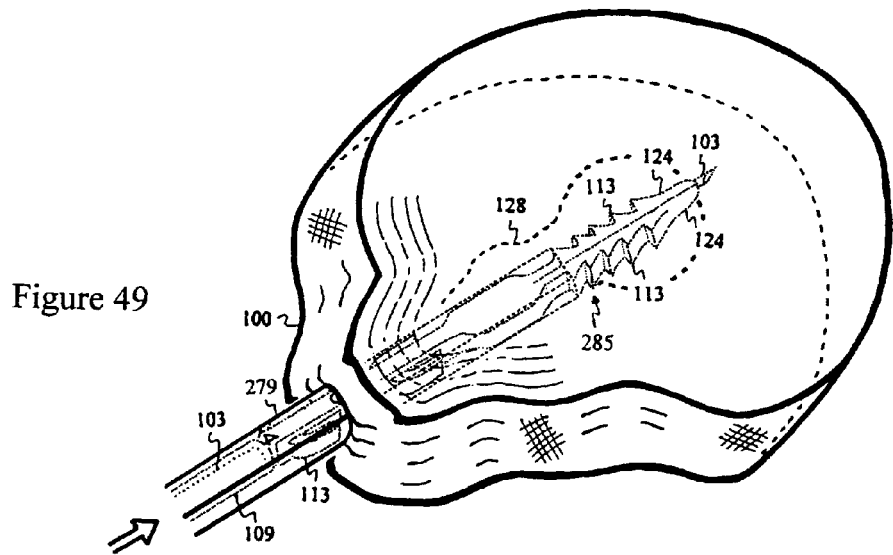
FIG. 49 shows penetration of the sleeve-covered-counter-gripping fastener 285 into a bulging disc 100.
Figure 50:
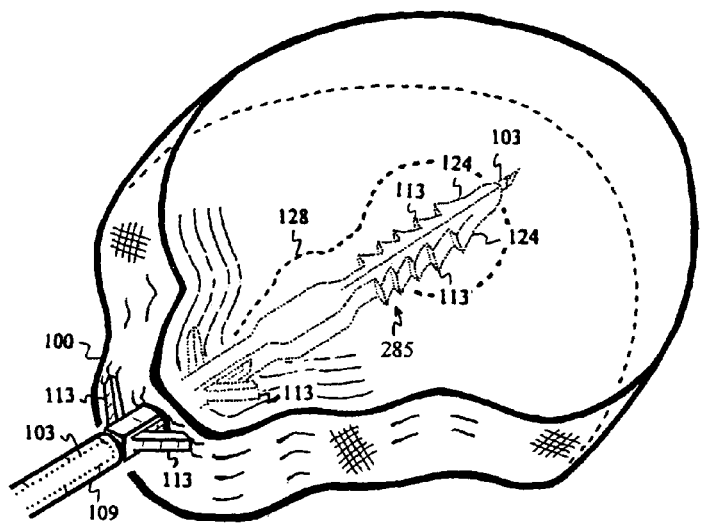
FIG. 50 depicts withdrawal of the sleeve 279, allowing the proximal gripping elements 113 to elastically open within and outside the anulus.
Figure 51:
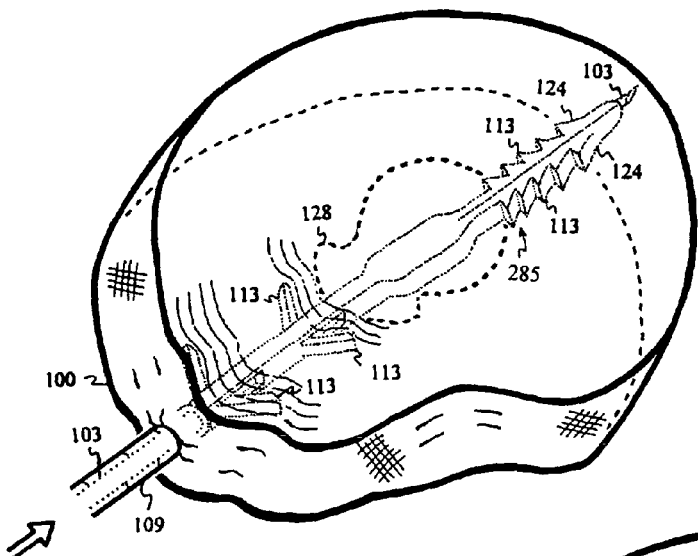
FIG. 51 shows the stepped trocar 103 advancing the fastener 285 into the disc 100 and pushing the bulging layers of anulus inward by the proximal gripping elements 113.
Figure 52:
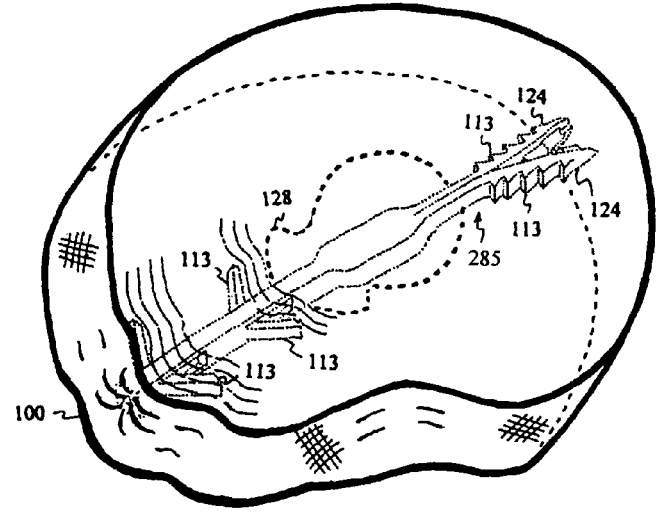
FIG. 52 depicts bulge fastening with the counter-gripping fastener 285 by withdrawing the stepped trocar 103 while holding the compressive sleeve 109 stationary. Then, the compressive sleeve 109 is also withdrawn.

The distal and proximal gripping elements 113 of a counter-gripping fastener 285 can be operated independently. The counter-gripping fastener 285 is also made with elastic material. The distal legs 124 of the fastener 285 are operated by a trocar 103 similar to that of the counter-gripping fastener 285 mentioned in FIG. 34. The proximal gripping elements 113 are elastically flared outward at an angle less than ninety degrees to trap, snag, hook, snatch or grab the surrounding tissue, as shown in FIG. 46. The proximal gripping elements 133 are also designed to be resiliently pressed inwardly into adjacent recesses 281. A stepped trocar 103 is inserted through a lumen 104 to restrict or bind the elastic distal legs 124 from opening, as shown in FIG. 47. The step 165 of the trocar 103 is for pushing and advancing the counter-gripping fastener 285. A compressive sleeve 109 is positioned to slide over the stepped trocar 103. A sleeve 279 with penetration markers is used to restrict or maintain the proximal-gripping elements 113 in closed positions, as shown in FIG. 48. Spearheaded by the stepped trocar 103, the counter-gripping fastener 285 is punctured into a bulging disc 100 with the sleeve 279 restricting and covering the proximal-gripping elements 113, as shown in FIG. 49. When a proper depth into the disc 100 has been reached, the sleeve 279 is withdrawn while the stepped trocar 103 is held stationary to open the proximal-gripping elements 113. The first set of the elements 113 open between layers of the bulging anulus; and the second set of the gripping elements 113 open external to the bulging disc 100, as shown in FIG. 50. The counter-gripping fastener 285 is further advanced into the disc 100 by pushing the stepped trocar 103. The first set of the opened elements 113 push against the inner layers of the bulging anulus toward the nucleus pulposus 128, as shown in FIG. 51. The second set of the gripping elements 113 push the outer layers of the bulging anulus inward, as the distal legs 124 advance toward the distal edge of the disc 100. The stepped trocar 103 is withdrawn while holding the proximal end of the counter-gripping fastener 285 stationary with the compressive sleeve 109. The distal legs 124 elastically open, pressing the gripping elements 113 into the distal anulus of the disc 100 to counter fasten the inwardly compressed anulus with the proximal-gripping elements 113, as shown in FIG. 52. Then, the compressive sleeve 109 is withdrawn from holding the proximal end of the fastener 285. As a result, nerve impingement is alleviated. The counter-gripping fastener 285, delivery device and method can be used endoscopically for a minimally invasive repair.

It may be possible to withdraw the stepped trocar 103 without using the compressive sleeve 109. When the resiliently straightened legs 124 of the counter-gripping fastener 285 are inserted into tissue, tightness of the insertion provides some restriction upon the straightened legs 124, keeping the legs 124 together, as indicated in FIG. 51. As a result, the friction between the trocar 103 and the retainers 106 is substantially decreased, while the legs 124 are bound and surrounded by the anulus. Furthermore, the gripping elements 113 of the legs 124 snag onto the tissue, which may allow the trocar 103 to withdraw and dislodge the fastener 285.

Figure 53:
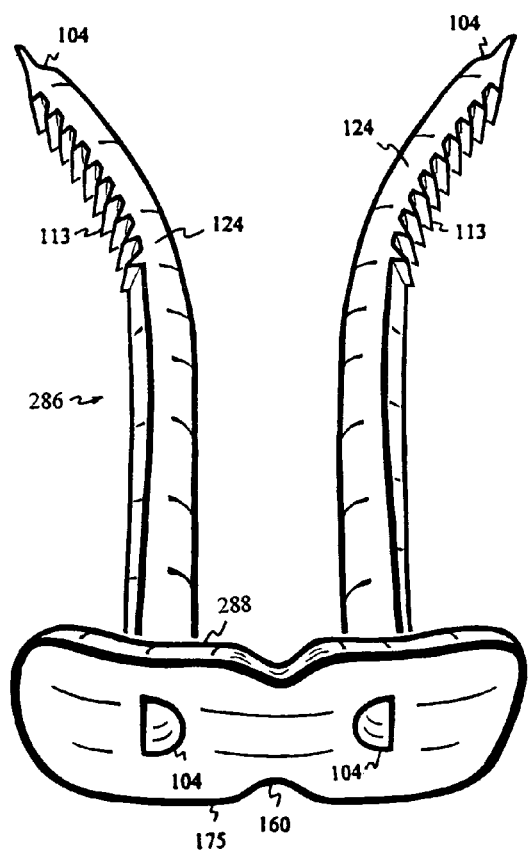
FIG. 53 shows a staple fastener 286 with two lumens 104 open from a bridge 175 through elastically curved legs 124 containing gripping elements 113.
Figure 54:
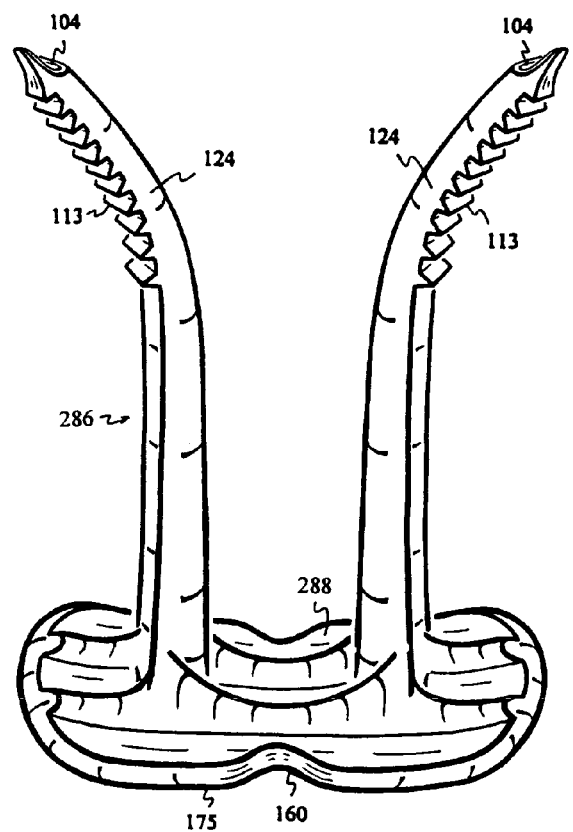
FIG. 54 shows the ridges and supports at the underside 288 of the bridge 175 and the lumens 104 extending to the distal ends of the legs 124.
Figure 55:
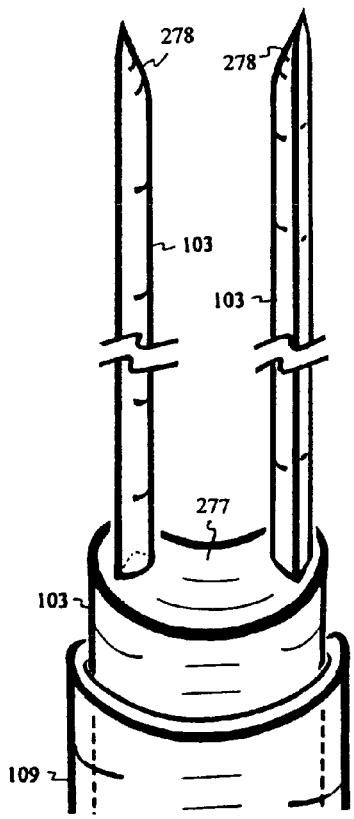
FIG. 55 depicts a double trocar 103 with semiconic tips 278 for inserting into the lumens 104 of the staple fastener 286, as shown in FIG. 53.
Figure 56:
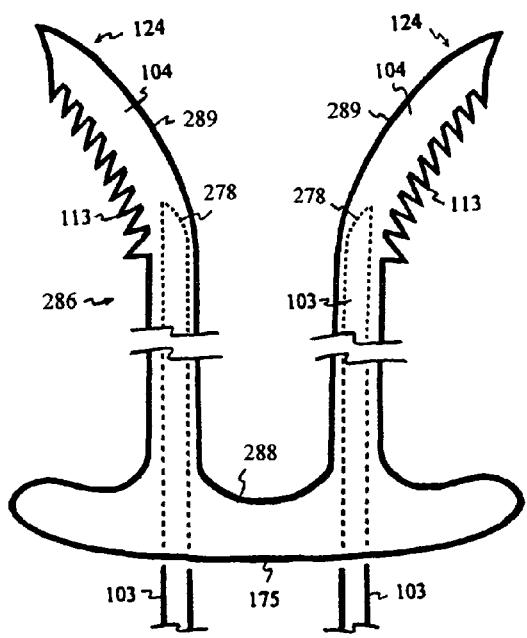
FIG. 56 shows trocar 103 insertion by sliding the semiconic tips 278 against the inner wall of the legs 124 of the staple fastener 286.
Figure 57:
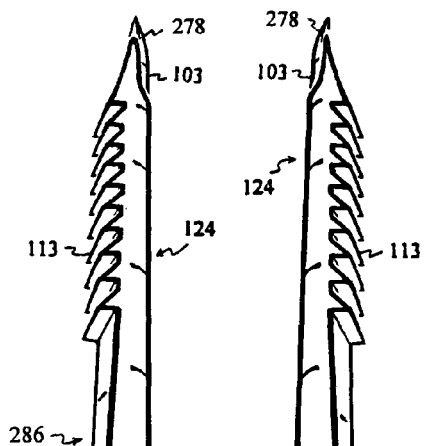
FIG. 57 shows resilient straightening of the elastic legs 124 by the rigid trocars 103.
Figure 58:
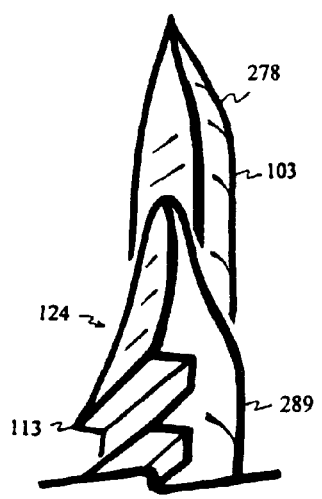
FIG. 58 shows the distal tip of a leg 124 and a protruding trocar 103.
Figure 59:
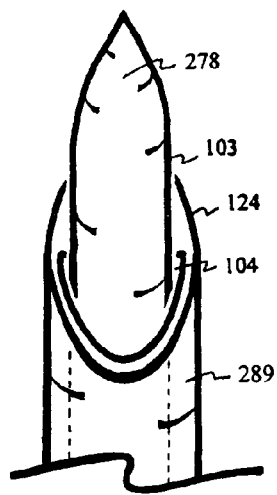
FIG. 59 shows the interior side of the leg 124 with trocar 103 protruding beyond the tapered distal tip of the leg 124 of the staple fastener 286.
Figure 60:
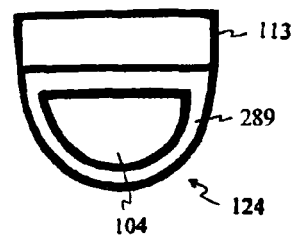
FIG. 60 shows a cross section of the leg 124 with a generally semi-circular lumen 104 and the outwardly facing rectangular gripping element 113.

The expandable fastener 286 can also be made like a staple with elastically curved legs 124 containing lumens 104 inside and gripping elements 113 outside, as shown in FIG. 53. The rectangular gripping elements 113 are designed to embed and fasten into tissue by elastic compression of the legs 124 to maximize the anchoring strength. The legs 124 are joined proximally by a bridge 175 with lumens 104 open from the bridge 175 leading to the distal ends of the legs 124. The bridge 175 contains tissue ingrowth openings 160 for securing or incorporating the staple fastener 286 into the fastened tissue. The inner surface 288 of the bridge 175 can be made smooth with a round contour to compress or with spikes to anchor the fastened tissue. The inner surface 288 can also contain ridges to fortify the bridge 175 and legs 124 of the staple fastener 286, as shown in FIG. 54. FIG. 55 depicts a double trocar 103, sized and configured for insertion into the lumens 104 of the staple fastener 286, as shown in FIG. 53. To facilitate insertion and straightening of the elastically curved legs 124, the double trocar 103 is generally semicylindrical, tapered to semiconical 278 distal tips. During double trocar 103 insertion, the semicones 278 slide and glide along the inner walls of the legs 124 to avoid puncturing and snagging within the elastically curved legs 124 of the staple fastener 286, as shown in FIG. 56. The inner walls of the curved legs 124 serve as trocar retainers 289 to restrain the elastic legs 124 from bending outwardly. In essence, the rounded sides of the distal ends of the trocars 103 facilitate insertion into the lumens 104 and straightening of the elastically curved legs 124. FIG. 57 shows lumen 104 insertion of the rigid double trocar 103 to straighten the elastic legs 124 from a curved to a generally parallel or straightened position. A compressive sleeve 109 is designed to fit and slide over the shaft of the double trocar 103, also shown in FIGS. 55 and 57. The trocars 103 protrude beyond the distal tips of the legs 124 with the flat portion of the semicylindrical trocars 103 supporting the gripping elements 113 from beneath, as shown in FIG. 58. The legs 124 of the staple fastener 286 are fortified by the double trocar 103 from within to prevent buckling or breakage during tissue insertion. The base 277 of the double trocar 103 and the distal end of the compressive sleeve 109 are sized and configured to fit and press against the bridge 175 of the staple fastener 286. FIGS. 58 and 59 show the tapered distal end and retainer 289 of the leg 124 with the protruding semiconical 278 tip of the trocar 103 to facilitate or spearhead tissue insertion. The tapered ends and semi-circular cross section of the legs 124 and trocars 103 are designed to ease tissue puncture and reduce tissue trauma during delivery of the staple fastener 286. FIG. 60 shows a cross-sectional view of the leg 124 with a generally semi-circular lumen 104 forming a half-ring like trocar retainer 289 and a flat support for the rectangular gripping elements 113 at the outer surface.

The double trocar 103 and the staple fastener 286 fit like a hand in a glove to straighten, protect, puncture and deliver the staple fastener 286. In summary, the double trocar 103 and the staple fastener 286 function as follows: (1) The semiconical 278 tips slide through the curved lumens 104. (2) The rigid trocars 103 straighten the elastically curved legs 124. (3) The trocars 103 fortify the legs 124 to prevent buckling or breakage during tissue insertion. (4) The exposed tips of the trocars 103 spearhead tissue insertion. (5) The base 277 of the double trocar 103 is positioned to press against the bridge 175 during tissue insertion.

Figure 61:
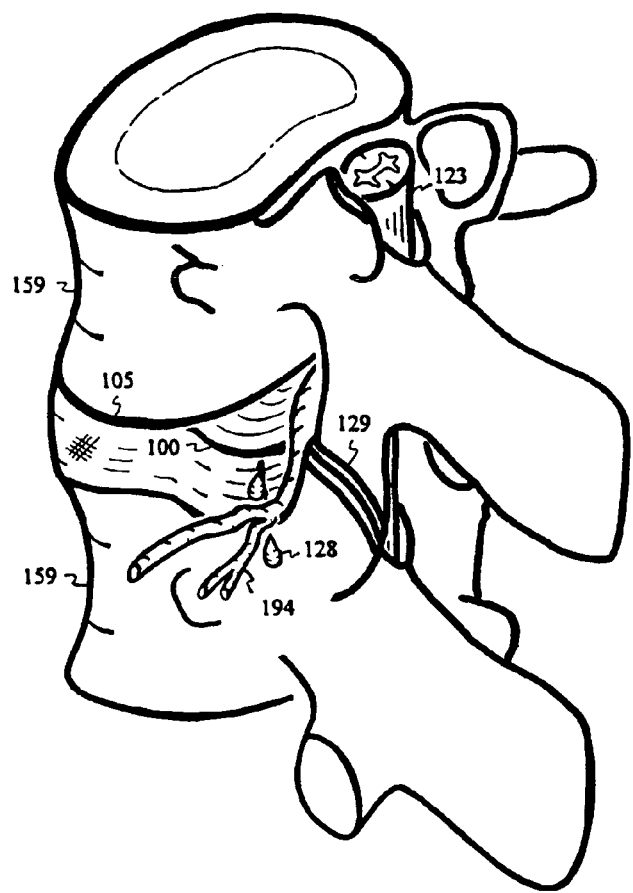
FIG. 61 depicts a bulging and herniated disc 100 impinging upon a nerve 194.
Figure 62:
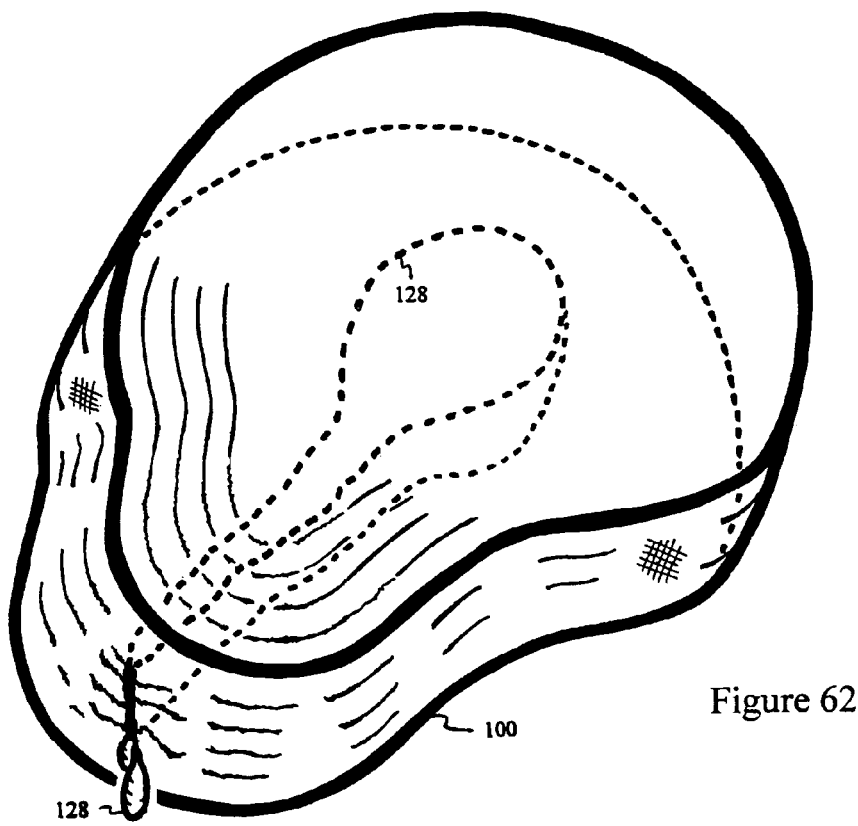
FIG. 62 depicts the bulging layers of anulus and a channel of leaking nucleus pulposus 128.
Figure 63:
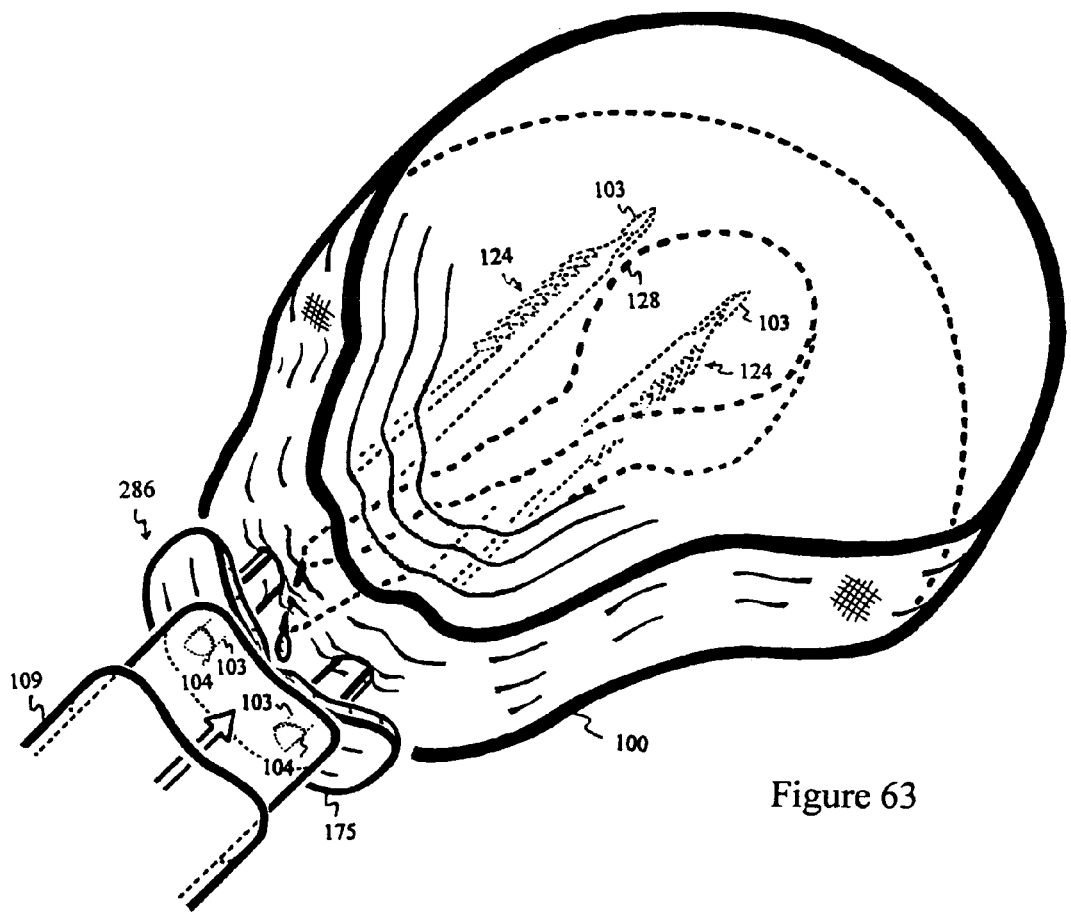
FIG. 63 shows insertion of the double trocar 103 and delivery of the staple fastener 286 into the bulging and herniated intervertebral disc 100.
Figure 64:
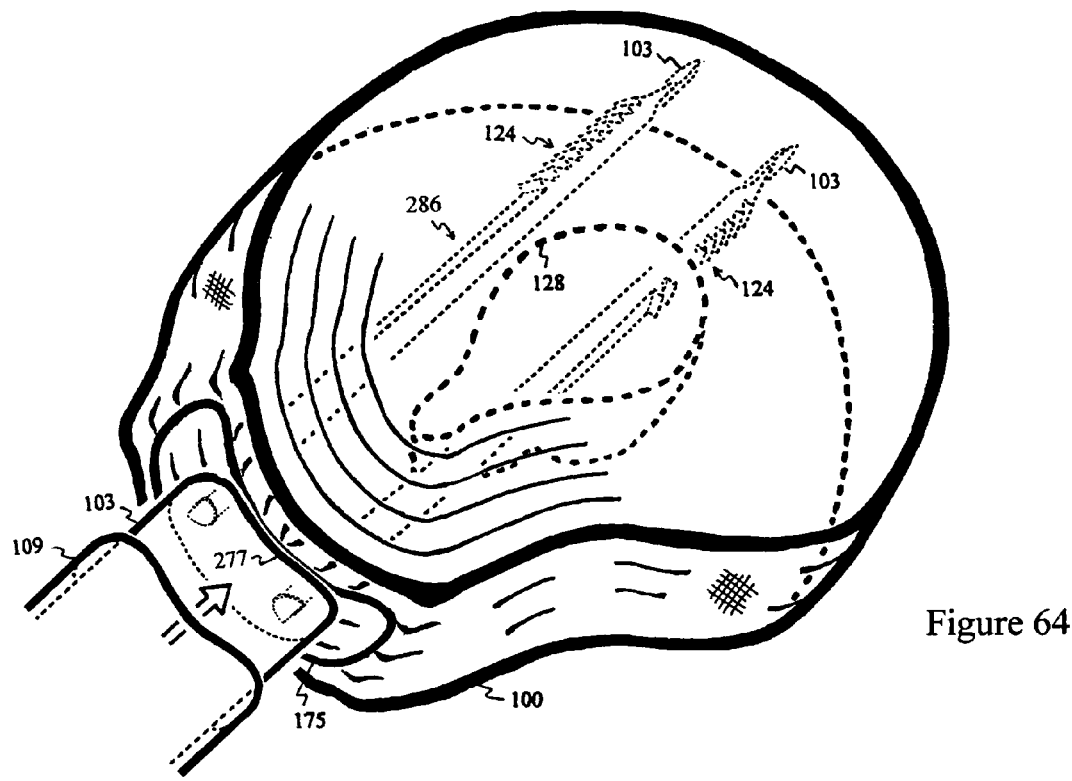
FIG. 64 depicts further insertion of the trocars 103 without exiting the disc 100.
Figure 65:
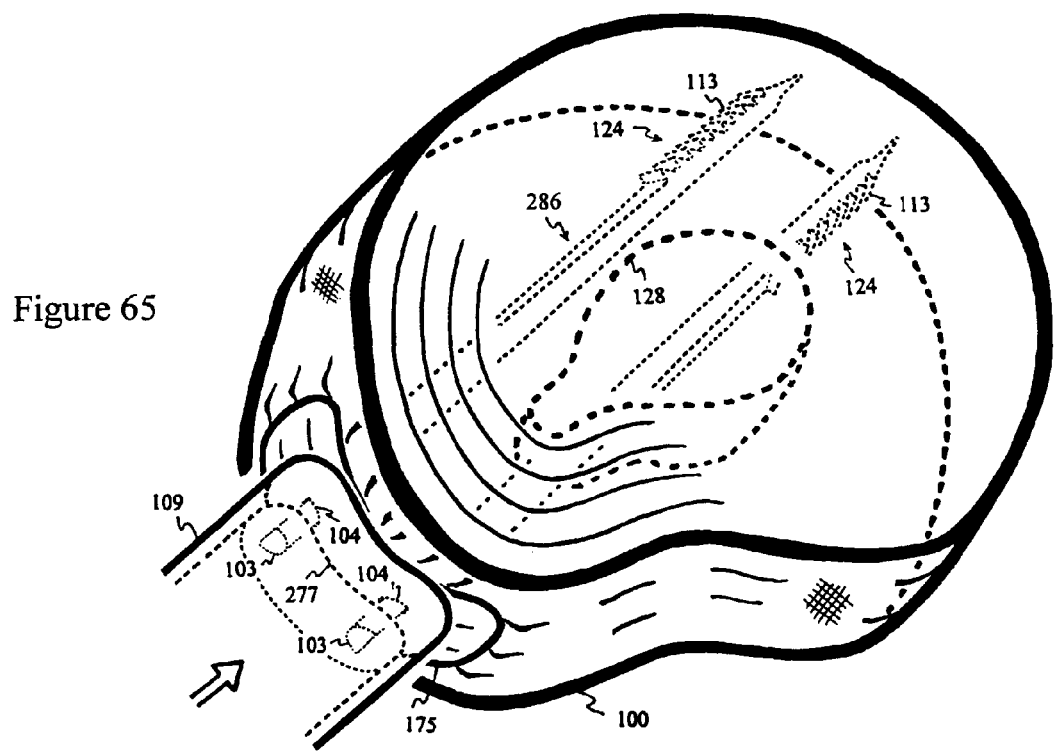
FIG. 65 shows the compressive sleeve 109 pressing the bridge 175 and the bulge to advance the legs 124 of the staple fastener 286 by sliding over the trocars 103.
Figure 66:
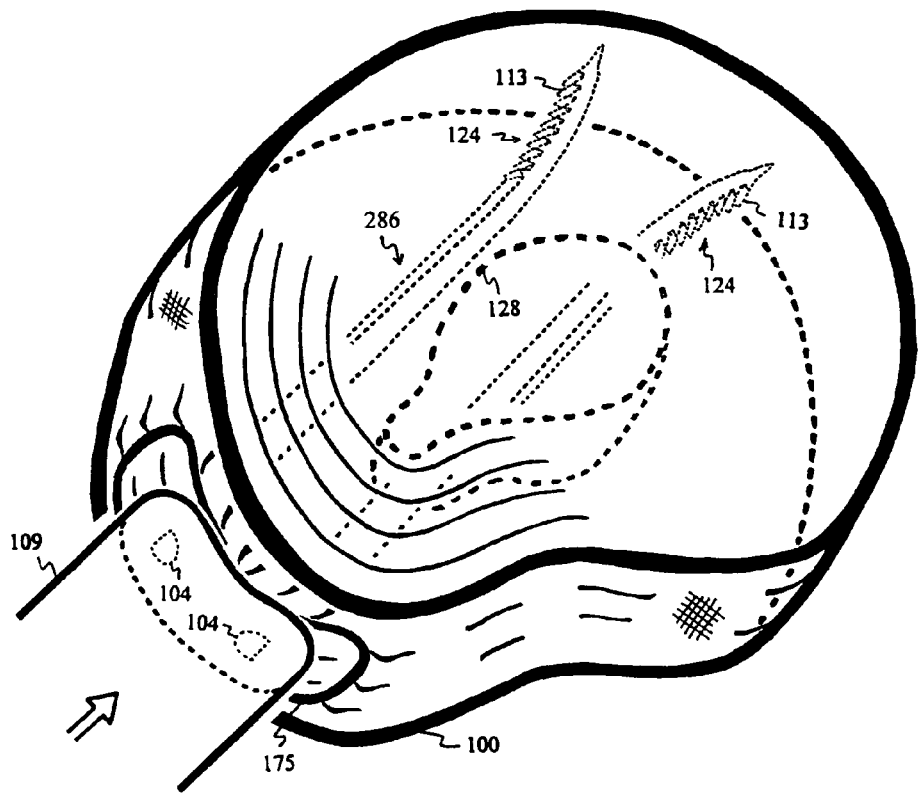
FIG. 66 depicts bulge fastening by withdrawing the trocars 104 to open and fasten the elastic legs 124 within the distal portion of the disc 100 while the compressive sleeve 109 continues to press against the bridge 175 and the disc 100.
Figure 67:
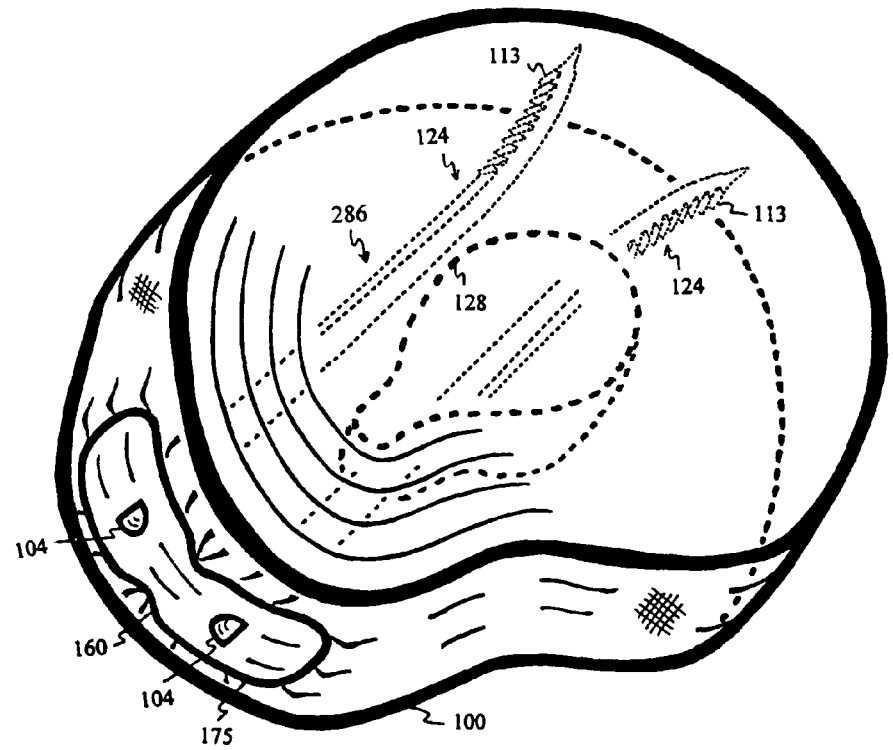
FIG. 67 shows the bulge compressed and fastened by the staple fastener 286.
Figure 68:
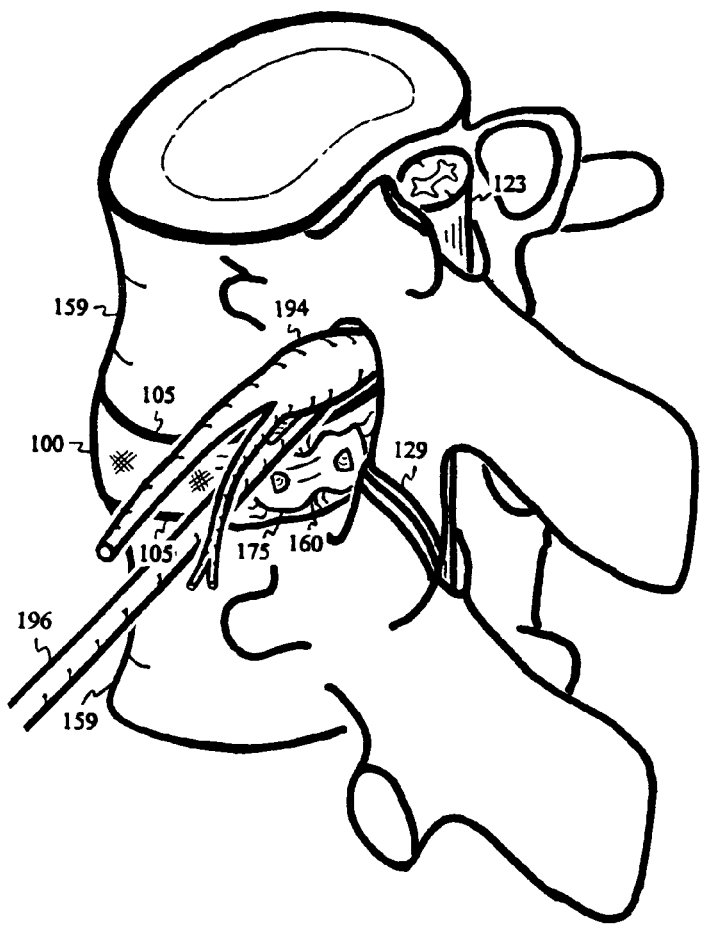
FIG. 68 depicts the result of the fastened disc 100: the bulging anulus is pressed in by the bridge 175 to alleviate nerve 194 impingement.

The staple fastener 286 can be used to repair a bulging intervertebral disc 100. FIG. 61 shows a herniated disc 100 impinging upon a nerve 194. FIG. 62 shows a leaking channel of nucleus pulposus 128 within the bulging disc 100. FIG. 63 shows the double trocar 103 spearheading penetration with the resiliently straightened legs 124 of the staple fastener 286 into the bulging disc 100. The curved base 277 of the double trocar 103, as shown in FIGS. 55 and 57, are sized and configured to fit and press the bridge 175 against the bulging anulus, as shown in FIG. 63. Due to major blood vessels located antero-lateral to the spine, the trocar 103 protrusion through the disc 100 can potentially rupture the blood vessels. Therefore, under fluoroscopic view or other imaging, advancement of the trocars 103 stops prior to exiting the disc 100, as shown in FIG. 64. The annular tissue distal to the distal ends of the legs 124 has already been punctured or carved open by the protruding tips of the sharp trocars 103 to allow further penetration by the tapered legs 124 of the staple fastener 286. Similar to the base 277 of the double trocar 103, the distal end of the compressive sleeve 109 is also sized and configured to conform to the shape of the bridge 175 for pressing against the staple fastener 286. As the bridge 175 is pushed by the compressive sleeve 109, the remaining bulging anulus is pressed into the disc 100; and the legs 124 of the staple fastener 286 slide further along the double trocar 103 into the disc 100, as shown in FIG. 65. Since the distal ends of the legs 124 are relatively blunt, the risk of blood vessel puncturing beyond the disc 100 is avoided. While the compressive sleeve 109 continues to press against the bridge 175 and the bulge, the double trocar 103 is withdrawn to allow the legs 124 to resume the elastic curvatures, as shown in FIG. 66. The degenerated anulus of the disc 100 is compressed and compacted. As a result, the leaking channel of the viscous nucleus pulposus 128 may also being compressed, narrowed or even sealed by the disc 100 fastening, as indicated in FIG. 66. The curvatures are greatest at the distal halves of the legs 124, pressing the gripping elements 113 into the relatively healthy and solid distal annular tissue to anchor and fasten the bulge, as shown in FIG. 66. Due to the central location of the gel-like nucleus pulposus 128, the legs 124 of the staple fastener 286 might be able to straddle the nucleus pulposus 128 to grip the sturdy annular tissue. Regardless, the outward curvatures of the legs 124 will press and anchor onto anulus surrounding the nucleus pulposus 128, as shown in FIG. 66. The length, size and/or curvature of the legs 124 can be varied with complementing trocars 103 to fit the anchoring sites and maximize the fastening strength of the staple fastener 286. FIG. 67 depicts the result of the fastened disc 100 after withdrawal of the compressive sleeve 109. In FIG. 68, the nerve 194 is lifted with a retractor 196 to show bulge compression by the bridge 175 of the staple fastener 286, which alleviates neural impingement and/or seals herniation.

Figure 69:
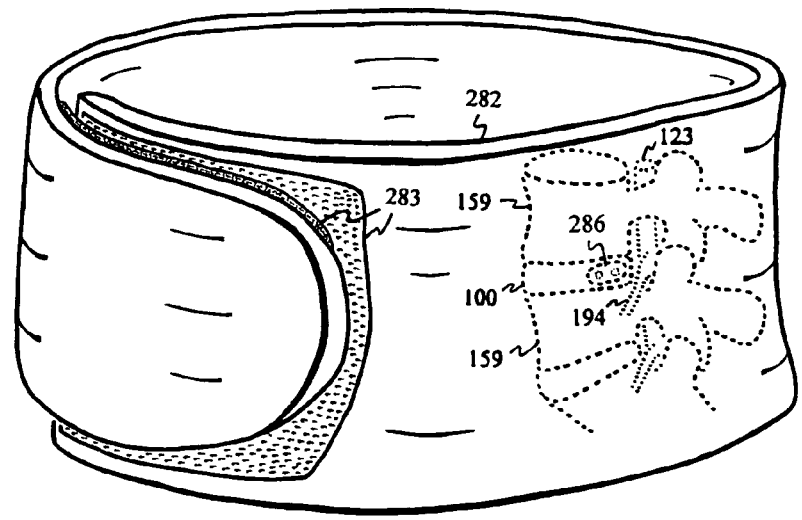
FIG. 69 indicates a wide belt as a spine restricting device 282 to limit the mobility of the repaired vertebral 159 segment and protect the staple fastener 286.

Intervertebral disc 100 fastening with the staple fastener 286 may interfere with lateral bending, extension and/or flexion movements of the vertebral segment. During the initial two to six months after disc 100 fastening with the staple fastener 286, the patients can be fitted with a wide belt 282 fastened by VELCRO™ 283 or a buckle to limit vertebral motion, as shown in FIG. 69. Limiting vertebral motion can prevent possible damage to the anulus or the staple fastener 286. After healing of the disc 100 and degradation of the staple fastener 286, normal range of motion and activity can then be resumed. The wide belt 282 can also be used by patients with other disc 100 fastening devices, such as the screw fastener 284 shown in FIG. 22 or counter-gripping fasteners 285 shown in FIGS. 44 and 52.

Figure 70:
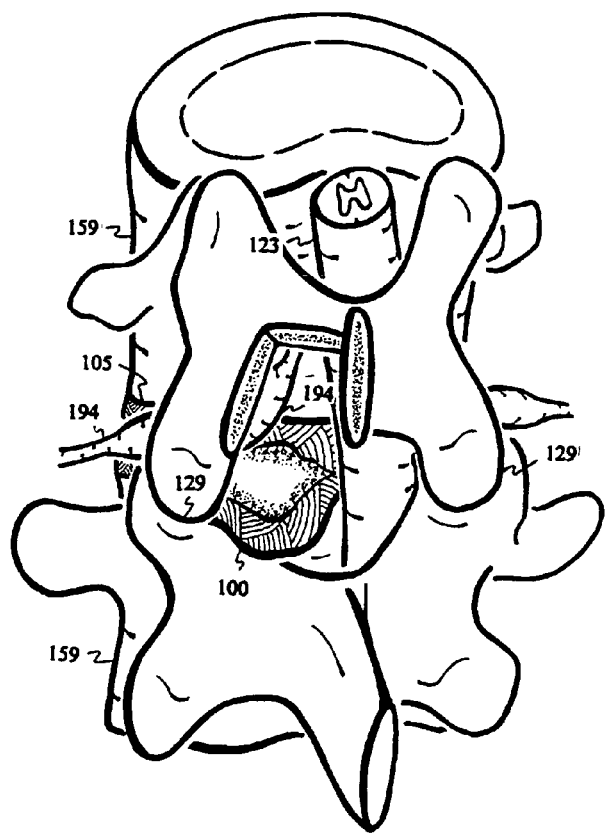
FIG. 70 shows posteriorly bulging disc 100 exposed after a laminotomy.
Figure 71:
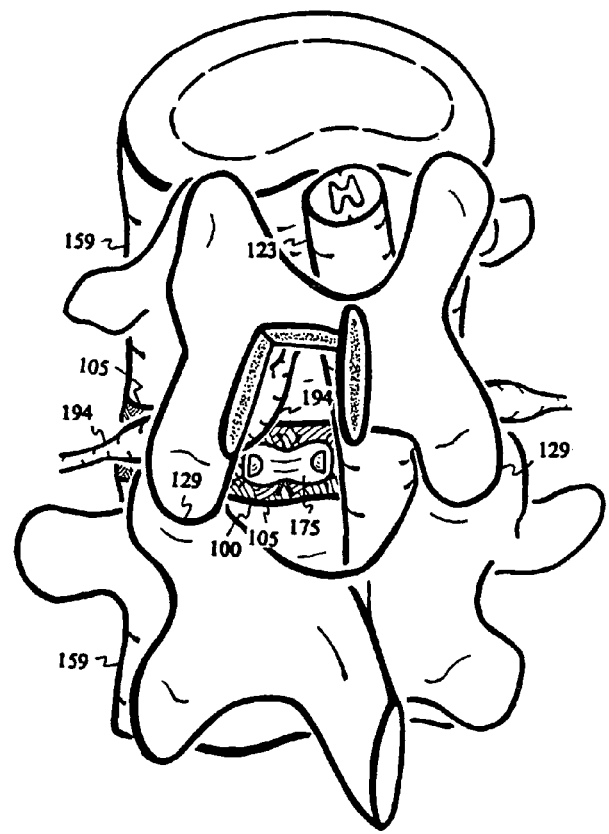
FIG. 71 shows bulge compression and fastening by the bridge 175 of the staple fastener 286 to alleviate nerve 194 impingement.

For disc 100 bulging within the central zone behind the lamina of the vertebral body 159, laminotomy is commonly performed to access the bulge, as shown in FIG. 70. Instead of performing a discectomy following the laminotomy, the bulging anulus is compressed and fastened by the bridge 175 of the staple fastener 286 to alleviate nerve 194 impingement, as shown in FIG. 71.

Concurrent with metabolism of the degenerated anulus, healthy and non-bulging anulus is shaped and formed under the bridge 175 of the staple fastener 286. The purpose of the staple fastener 286 is to (1) fasten the bulge to alleviate nerve 194 impingement, (2) seal the leakage of nucleus pulposus 128, (3) shape the newly forming anulus, and/or (4) degrade after healing of the disc 100.

The rate of degradation of various parts of the staple fastener 286 may be quite different and significant in terms of safety and efficacy of the staple fastener 286. Within the generally avascular disc 100, fluid exchange between the nucleus pulposus 128 and the end plates 105 of the sandwiching vertebral bodies 159, as shown in FIGS. 68 and 71, is quite limited. Therefore, the rate of hydrolysis/degradation of the legs 124 within the disc 100 is expected to be slower, perhaps much slower, than the rate of degradation of the bridge 175 located at the periphery of the disc 100. In essence, bulge anchoring with the compressive gripping elements 113 on the legs 124 is expected to outlast the compression of the bridge 175 of the staple fastener 286. It is unlikely to have erosion/degradation on both anchoring legs 124 causing the bridge 175 to break off and migrate into a nerve 194. Even if both anchoring legs 124 degrade before the bridge 175, the tissue ingrowth openings 160 on the bridge 175 are designed to trap or bind anular tissue, preventing detachment of the bridge 175 from the disc 100. The legs 124 of the biodegradable fastener 144, 284 or 286 can be coated with a water-repellent compound to reduce the rate of hydrolysis/degradation, thereby providing a durable anchoring support to the bridge 175 or head 101 of the fastener 144, 284 or 286.

Figure 72:
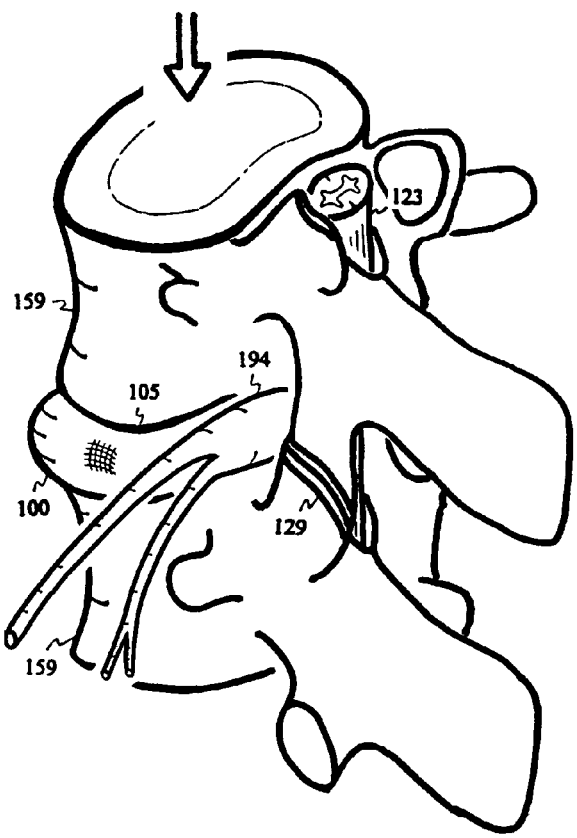
FIG. 72 shows normal bulging of a disc 100 responding to weight loading.
Figure 73:
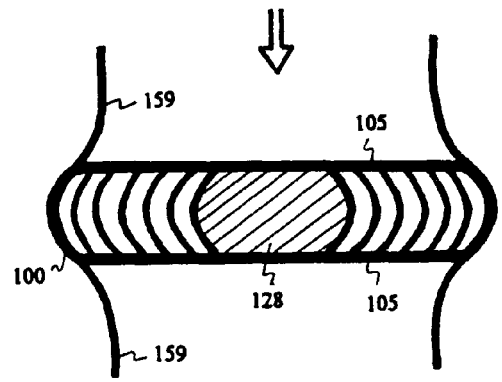
FIG. 73 indicates a longitudinal cross-section of a normal vertebral segment responding to weight loading by bulging of the anular layers outward.
Figure 74:
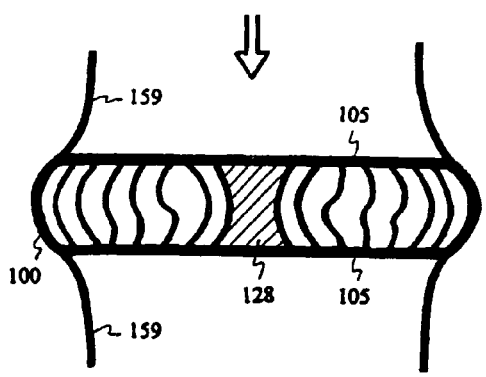
FIG. 74 indicates diminishing nucleus pulposus 128 resulting in delamination of anulus within the degenerated disc 100.

The normal intervertebral disc 100 is designed to bulge slightly and resiliently to absorb the load upon the spine, as shown in FIG. 72. FIG. 73 indicates a mid-longitudinal view of the normal vertebral segment, responding to the weight from above by flexing the layers of anulus outward, resulting in normal bulging of the disc 100. However, as the disc 100 degenerates, the internal support of the anular layers decreases, possibly corresponding to the diminishing water content of the nucleus pulposus 128. Recent research confirms the possibility of anular defects due to dehydration of nucleus pulposus 128. Studies show that anular unity is lost within cadaveric discs 100 with depleting nucleus pulposus 128. In fact, the anular layers of degenerated discs 100 delaminate or separate from each other, as shown in FIG. 74.

Figure 75:
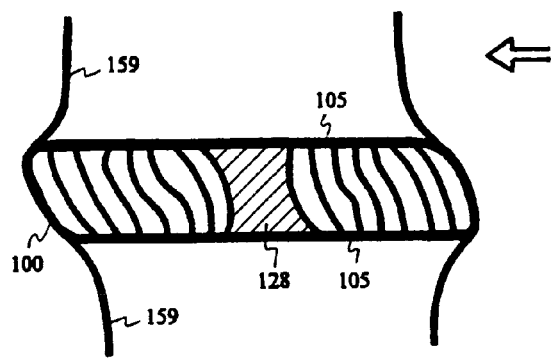
FIG. 75 shows swaying of the vertebral 159 segment caused by the degenerated disc 100.
Figure 76:
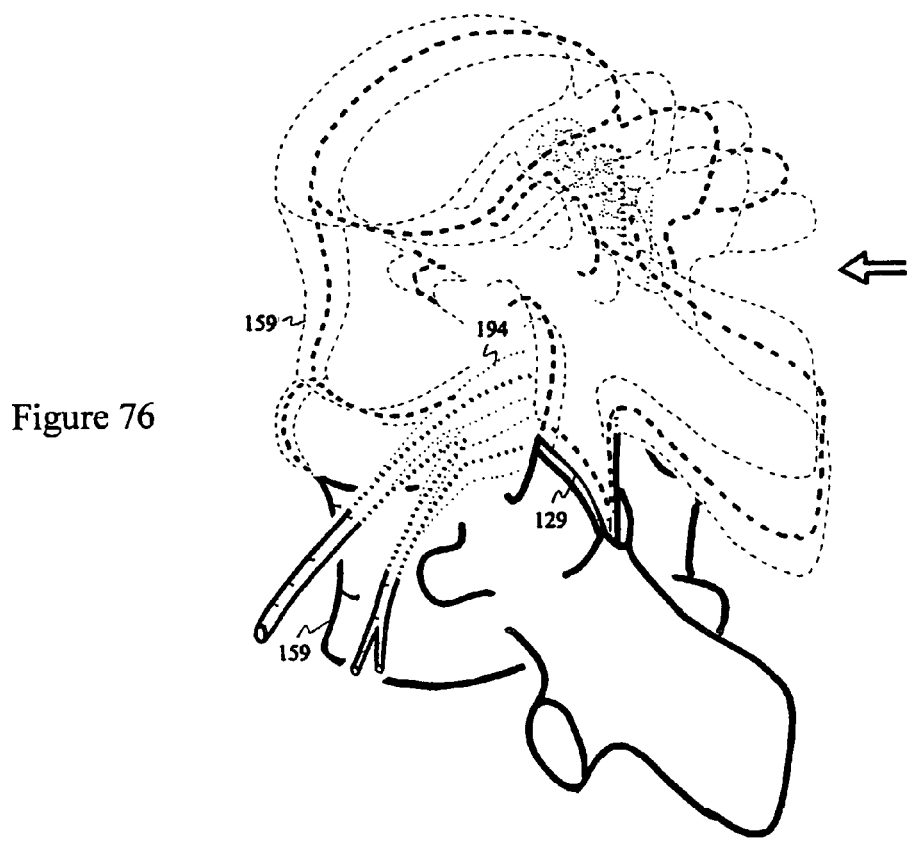
FIG. 76 indicates intervertebral instability above the facet joint 129.

Unlike patients with identifiable nerve 194 impingement, most low back pain patients show no radiographic evidence of disc 100 bulging or bone impairment, but continuously have unidentifiable and nonspecific pain. Experts believe that some of these patients may suffer from unstable motion segments (vertebral body-disc-vertebral body) caused by degenerated discs 100. The unstable movement is called segmental instability. Segmental instability resembles an out-of-control car riding on a flat or partially deflated tire with unsupported sidewalls. The disc 100 with partially dried nucleus pulposus 128 is similar to the partially deflated tire. A routine vertebral motion could start swaying of the degenerative segment, as shown in FIG. 75. The excessive movement from swaying of the motion segment causes irritation, inflammation, strain and pain in surrounding ligaments and facet joints 129, as indicated in FIG. 76. Treatment recommended for segmental instability is mostly rest and drug therapy, including analgesics, anti-inflammatory agents, oral steroids, muscle relaxants and/or antidepressants.

Figure 77:
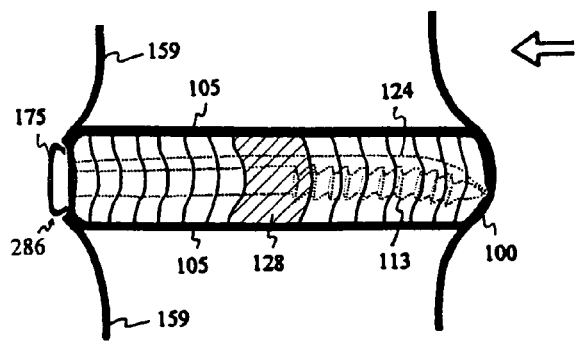
FIG. 77 indicates binding of the anular layers by the staple fastener 286 and restoring intervertebral stability to the repaired disc 100.

Expandable fasteners 284, 285 and/or 286 and methods used to fasten bulges, as shown in FIGS. 22, 45, 52, 67 and/or 71 can also be used to minimize segmental instability of the degenerated disc 100. Bulge fastening using the expandable fasteners 284, 285 and/or 286 is accomplished by compressing or restricting the anular layers of the degenerated disc 100. Compression of the bridge 175 provides side support to the disc 100, as shown in FIGS. 67 and 77. Similarly, the disc compressor 111 also provides side support to the disc 100, as shown in FIG. 22. Layers of anulus are linked, fastened, tied and/or unified by the anchoring legs 124 of the expandable fasteners 284, 285 and/or 286 to promote rigidity and stability within the degenerated disc 100, as shown in FIGS. 22, 45, 52, 67, 71, 77 and/or 78. Furthermore, insertion of the legs 124 of the expandable fasteners 284, 285 and/or 286 also provides bulk and cushion within the disc 100 to reduce compressibility and instability of the degenerated disc 100.

By adding bulk within the discs 100 and consolidating the bulging anulus, the expandable fasteners 284, 285 and/or 286 in FIGS. 22, 45, 52, 67 and/or 71 may also thicken the degenerated discs 100 to alleviate nerve 194 impingement from spinal stenosis.

Figure 78:
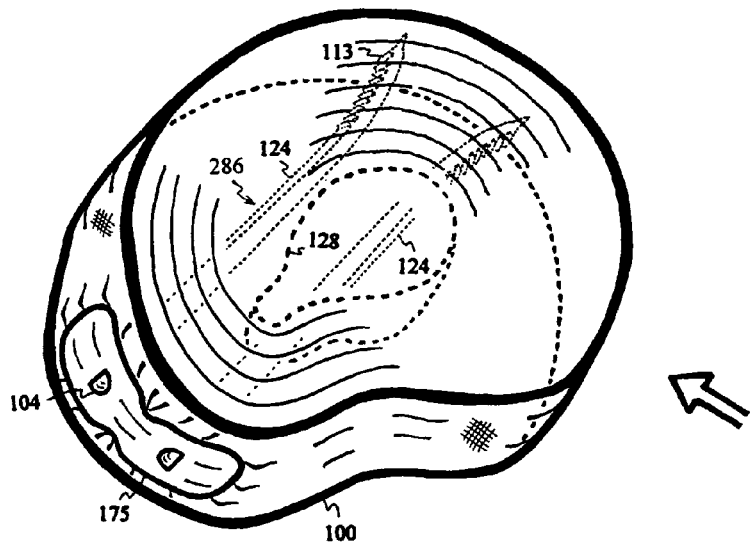
FIG. 78 shows binding or linking the anulus of the repaired disc 100 by the staple fastener 286 to restore intervertebral stability.
Figure 79:
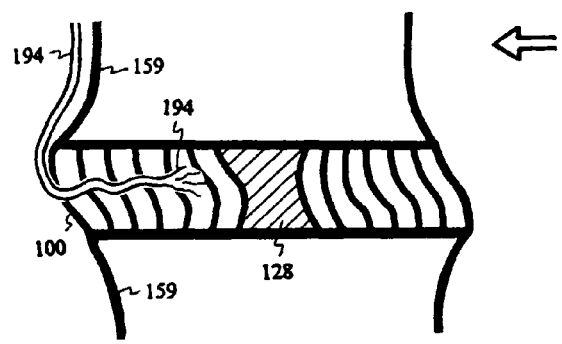
FIG. 79 indicates nerve 194 ingrowth into a degenerated disc 100, transmitting painful sensation during intervertebral instability.
Figure 80:
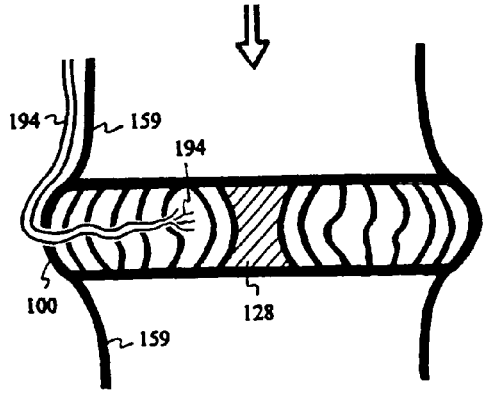
FIG. 80 shows nerve 194 ingrowth into a degenerated disc 100, transmitting painful sensations during bulging or bending of the anulus.
Figure 81:
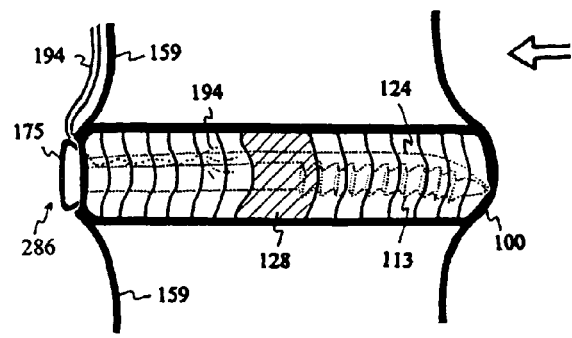
FIG. 81 indicates atrophy of the ingrown nerve 194 due to prolonged compression of the staple fastener 286.

Chronically degenerated discs 100 can induce ingrowth of sinuvertebral nerves 194 into the anulus, emitting pain signals within the disc 100 during swaying, as shown in FIG. 79, and bulging, as shown in FIG. 80. Sinuvertebral nerves, which normally grow only on the surface, extend well into the disc 100 when it is degenerating. The staple fastener 286 in FIG. 78, or the compressor 111 in FIG. 22 can compress the sinuvertebral nerves 194 at the surface of the disc 100 causing the nerve 194 to atrophy, thus ceasing or interrupting the signals of pain transmitted within the degenerated disc 100.

Figure 86:
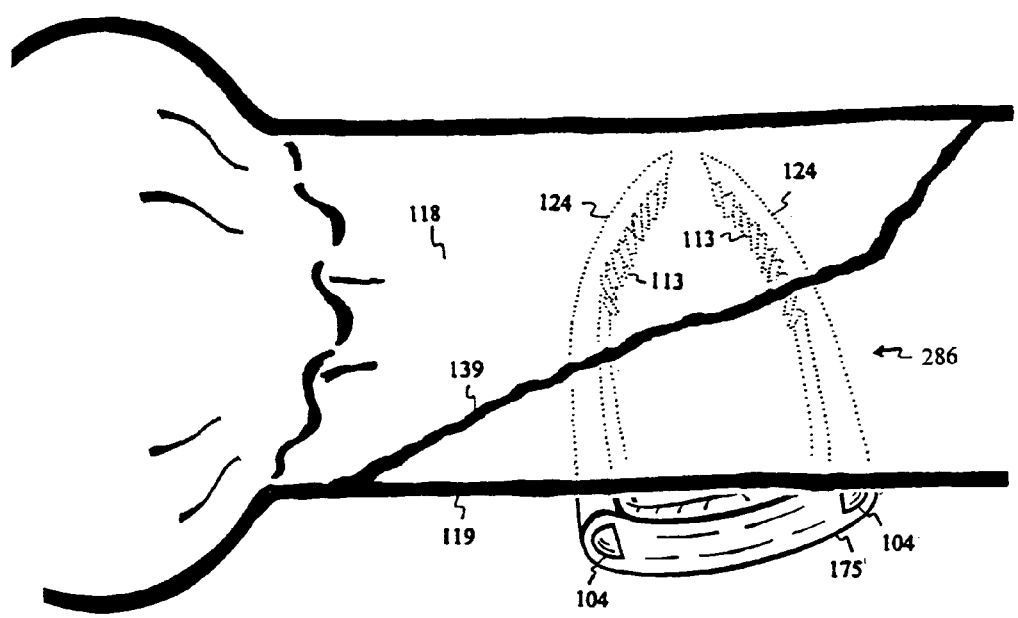
FIG. 86 depicts repair of a broken bone 118 with the inwardly curved legs 124 of the staple fastener 286.

The legs 124 of the staple fastener 286 can also be elastically and inwardly curved with lumens 104 opened into and through the curved legs 124, as shown in FIG. 82. The inward curvature can be further intensified by overlapping the legs 124 and placing the legs 124 in different planes, as shown in FIG. 83. The outwardly facing semicones 278 of the double trocar 103 straighten the inwardly curved legs 124, as shown in FIG. 84. During insertion of the trocars 103, the semicones 278 slide and glide along the outer wall of the legs 124 to avoid puncturing and snagging within the elastically curved legs 124 of the staple fastener 286, as shown in FIG. 84. The outer walls of the curved legs 124 serve as trocar retainers 289, to restrain the elastic legs 124 from bending inwardly. FIG. 85 shows straightening of the elastic legs 124 by the rigid trocars 103, from a curved to a generally parallel position for delivery. In essence, the round or blunt sides of the tips of the double trocar 103 facilitate insertion into the lumens 104 and straightening of the elastically curved legs 124. The base 277 of the double trocar 103 is sized, shaped and configured to fit and compress the bridge 175 of the staple fastener 286. Similar to the outwardly opening staple fastener 286, the double trocar 103 protects, strengthens and delivers the inwardly opening staple fastener 286. The sharp distal tips spearhead tissue puncturing, and the base 277 presses against the bridge 175 to drive the legs 124 of the staple fastener 286 into tissue, such as broken bone 119. As the resiliently straightened legs 124 insert into tissue, tightness of the insertion provides restriction upon the straightened legs 124, keeping the legs 124 in a parallel position. As a result, the friction between the double trocar 103 and the retainers 289 substantially decreases, while the legs 124 are bound and surrounded by the tissue. Furthermore, the gripping elements 113 of the legs 124 snag onto the tissue, allowing the double trocar 103 to withdraw and dislodge the staple fastener 286. Therefore, the staple fastener 286 may able to be delivered with or possibly without the compressive sleeve 109. FIG. 86 shows fastening of the broken bone 119 with the bridge 175 anchored externally and the gripping elements 113 internally onto cancellous bone 118 to hold the broken 139 junction closed.

Elastic fastening provides superior anchoring strength to approximate torn 139 tissue. The legs 124 of the staple fastener 286 are delivered straight into the tissue with the bridge 175 pressing against the surface. As the double trocar 103 is withdrawn from the staple fastener 286, the legs 124 resume the predisposed elastic curvatures to (1) press the gripping elements 113 into tissue, and (2) approximate the torn tissue 139 through elastic closure. As a result, the elastically fastened tissue is likely to provide no gap at the torn junction for proper and quick healing.

Multiple staple fasteners 286 can be made connected to each other, separated by perforations. The connected staple fasteners 286 form a strip, as the staples for papers, loading into a stapler equipped with double trocar. The strip of staple fasteners 286 is compressed by a spring in the stapler, positioning one staple fastener 286 at a time under the double trocar for delivery. In one downward stroke, the double trocar inserts into the lumens 104, straightens the elastically curved legs 124, breaks off the positioned staple fastener 286 from the strip, punctures into tissue and compresses the bridge 175 with the base to deliver the staple fastener 286. As the resiliently straightened legs 124 insert into tissue, tightness of the insertion provides restriction upon the straightened legs 124, keeping the legs 124 in a parallel position. While the parallel legs 124 are bound and surrounded by the tissue, the friction between the double trocar and the retainers 289 substantially decreases. Furthermore, the gripping elements 113 of the legs 124 snag onto tissue, allowing the double trocar to withdraw and dislodge the staple fastener 286. The returned double trocar is ready to deliver another staple fastener 286 advanced by the spring in the stapler. To ensure proper dislodging of the fastener 286, a compressive sleeve can also be used to hold the bridge 175 of the staple fastener 286 while the double trocar withdraws. The compressive sleeve can slide over the base of the double trocar. It is also possible to compress the staple fastener 286 with a plunger extending from the base of the double trocar. Operation of the double trocar, compressive sleeve or the plunger can be motorized, air-driven or manual.

The staple fasteners 286 can also be used to repair soft tissue. The degradable staple fastener 286, as shown in FIGS. 83, 82 and/or 53, may be effective in treating pneumothorax of the punctured lung by sealing air leak into the pleural space.

Figure 87:
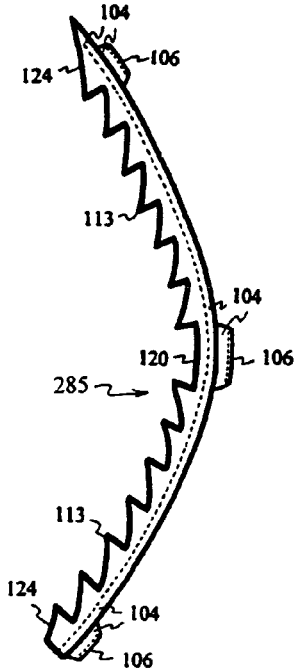
FIG. 87 shows a one-piece elastically curved counter-gripping fastener 285 with a trough 104, trocar retainers 106 and gripping elements 113.
Figure 88:
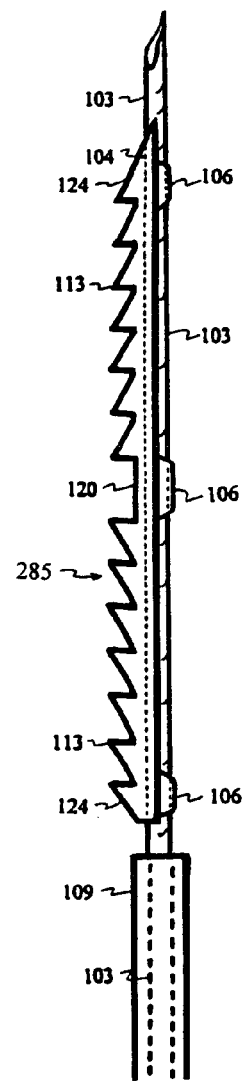
FIG. 88 depicts the one-piece elastic fastener 285 being resiliently straightened by a trocar 103, deliverable by a compressive sleeve 109.

Counter tissue fastening can also be accomplished with a one-piece elastically curved fastener 285 with a trough 104, trocar retainers 106 and gripping elements 113, as shown in FIG. 87. In FIG. 88, the one-piece elastic fastener 285 is resiliently straightened by a trocar 103 and ready to be delivered by a compressive sleeve 109. The delivery of the one-piece fastener 285 is similar to the procedure used for the counter fastener 285 depicted in FIG. 33.

The expandable tack fastener 144 can also be used as a suture fastener 144. Components of a suture fastener 144 depicted in FIG. 89 are slightly modified from the components of the tack fastener 144 mentioned in FIG. 1. The modified tack fastener 144 contains openings 235 for passing a suture 122 and a small head 101. The assembled suture fastener 144, as shown in FIG. 90, is in an open position with the elastic legs 124 spread apart. To deliver the suture fastener 144, the elastically curved legs 124 are resiliently straightened with the retainers 106 positioned within the indentations 112. The legs 124 are then held in the closed position by linking the retainers 106 with the trocar 103, as shown in FIG. 91. The suture fastener 144 is delivered into cancellous bone 118 by the trocar 103 and compressive sleeve 109, as shown in FIG. 92, to reattach a torn ligament 138. The trocar 103 and compressive sleeve 109 are then withdrawn, allowing the elastic legs 124 to open and fasten within the bone 118. The suture 122 is used to fasten and reattach the ligament on the cancellous bone 118. The suture fastener 144 can also anchor in soft tissue, especially for minimally invasive or endoscopic surgery.

The counter fastener 285, as shown in FIG. 33, can also become a suture fastener 285 by attaching a suture 122. FIG. 93 depicts the components of a suture fastener 285, similar to the one shown in FIG. 35. A suture 122 is threaded through suture openings 235 of the counter fastener 285. Joining of retainer 106 to indentation 112 serves as tongue and groove at the midsection of the suture counter fastener 285. In the open position, the distal legs 124 compress and anchor the gripping elements 113 into tissue to resist pull out. The proximal legs 124 wedge open, trapping and anchoring tissue between the interior sides of the proximal legs 124. Unlike tissue counter fastening, the gripping elements 113 on the proximal legs 124 are not crucial for suture 122 fastening. The anchoring strength of the suture 122 is from the gripping elements 113 on the distal legs 124 and tissue wedged between the proximal legs 124. A ring 107 or other restrictive means can be used to fasten the midsection of the elastic components. The tension of the suture 122 also holds the elastic pieces of the fastener 285 together. FIG. 94 depicts resilient straightening of the elastic legs 124 of the suture fastener 285 by inserting a trocar 103 through the retainers 106 in preparation for delivery. Delivery of the suture fastener 285 is similar to that of the counter fastener 285. Spearheaded by the trocar 103, the suture fastener 285 punctures and enters into the tissue. Markers on the compressive sleeve 109, as shown in FIG. 94, indicate depth of tissue penetration. When the proper depth is reached, the trocar 103 is withdrawn while the compressive sleeve 109 is held stationary to deploy the suture fastener 285 into tissue. The elastic and unrestricted legs 124 open and fasten within tissue, anchoring the suture 122 for various repairs.

Closure and healing of meniscal tears 139 are challenged by the pressure between bones and lack of blood supply within most of the meniscus 135. The meniscus 135 is the cartilaginous cushion between constantly rubbing condyles of the femur and tibia. Only the outer quarter to one-third of the meniscus 135 is vascularized with significant possibility of healing. After surgical repair, if a gap is created at the supposed closure by rubbing and/or pressure between the condyles, healing is unlikely and pain persists. Due to the elastic curvatures of the counter-fastening legs 124, the gripping elements 113 are pressed into the meniscal tissue 135 to provide superior fastening strength to secure and maintain the closure of the tear 139. Unlike repair with suture or prior art devices, the counter-gripping fasteners 285 are totally concealed within the meniscus 135 to prevent scraping or scratching of the delicate articular cartilage of the condyles, which can lead to irreversible damage to the joint. The counter-gripping fasteners 285 can be made with degradable material to approximate and heal the tear 139, then degrade to avoid migration or potential exposure at the joint.

Figure 95:
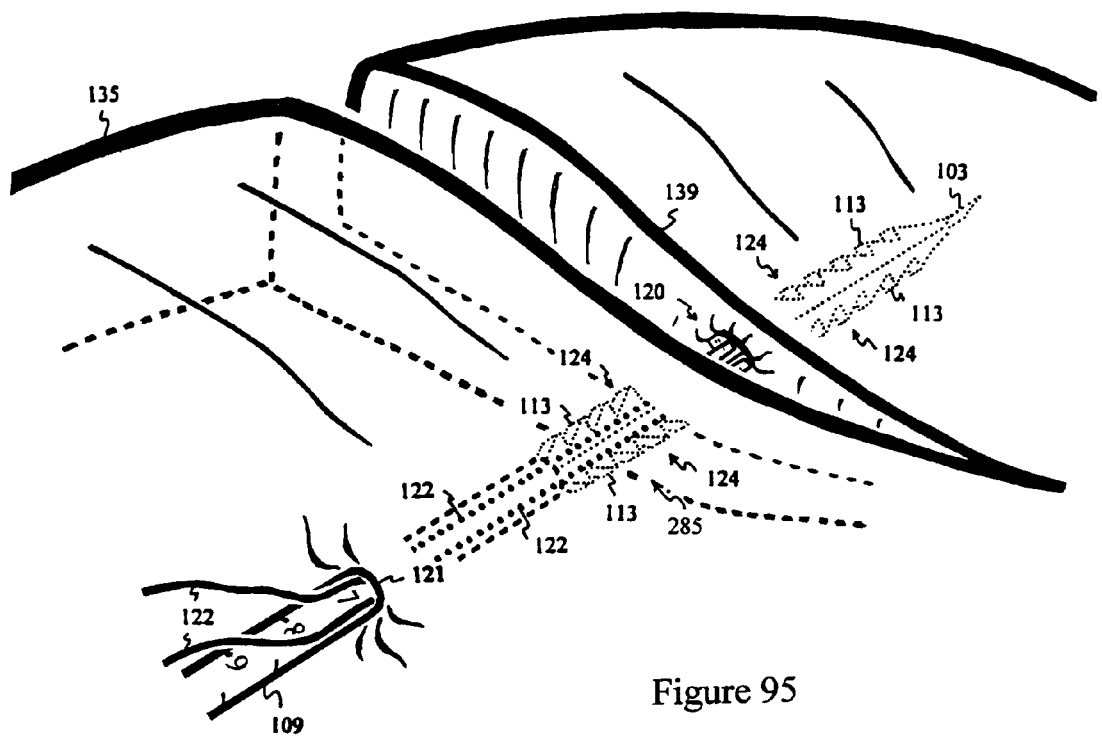
FIG. 95 depicts a needle 103 leading the suture counter-gripping fastener 285 puncturing and bridging a meniscal tear 139.
Figure 96:
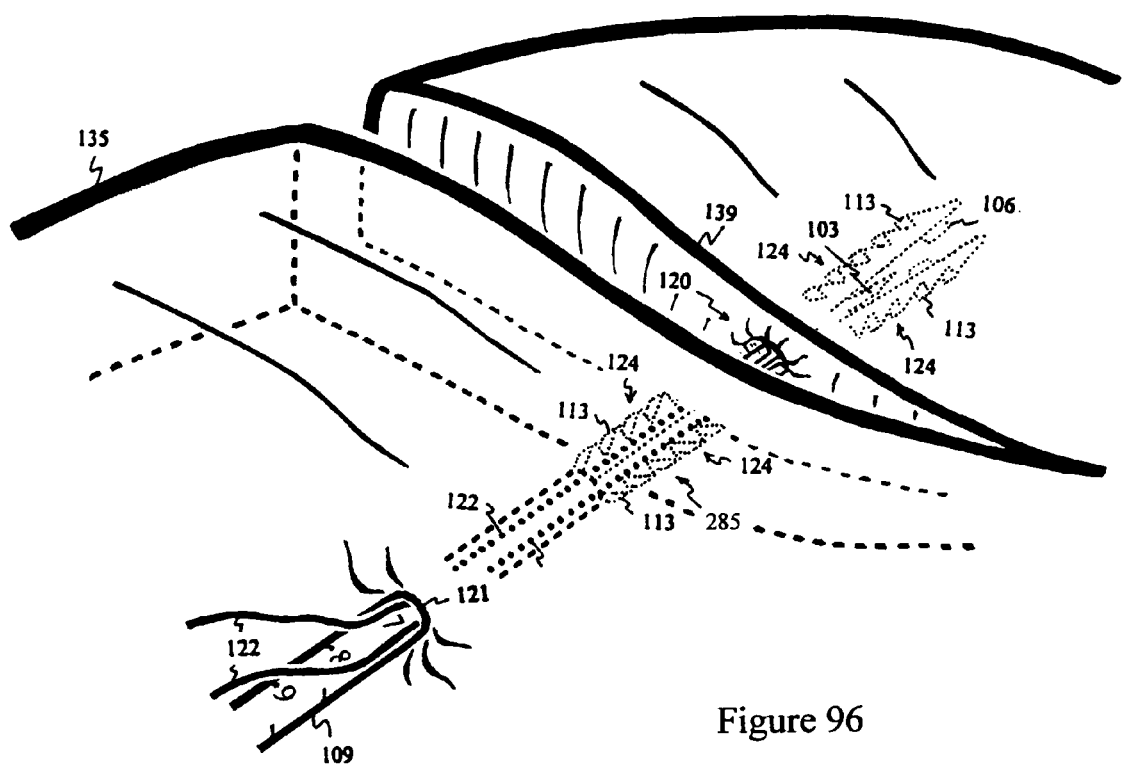
FIG. 96 shows distal anchoring of the suture fastener 285 within the torn tissue by partial withdrawal of the needle 103 while the compressive sleeve 109 is held stationary behind the suture fastener 285.
Figure 97:
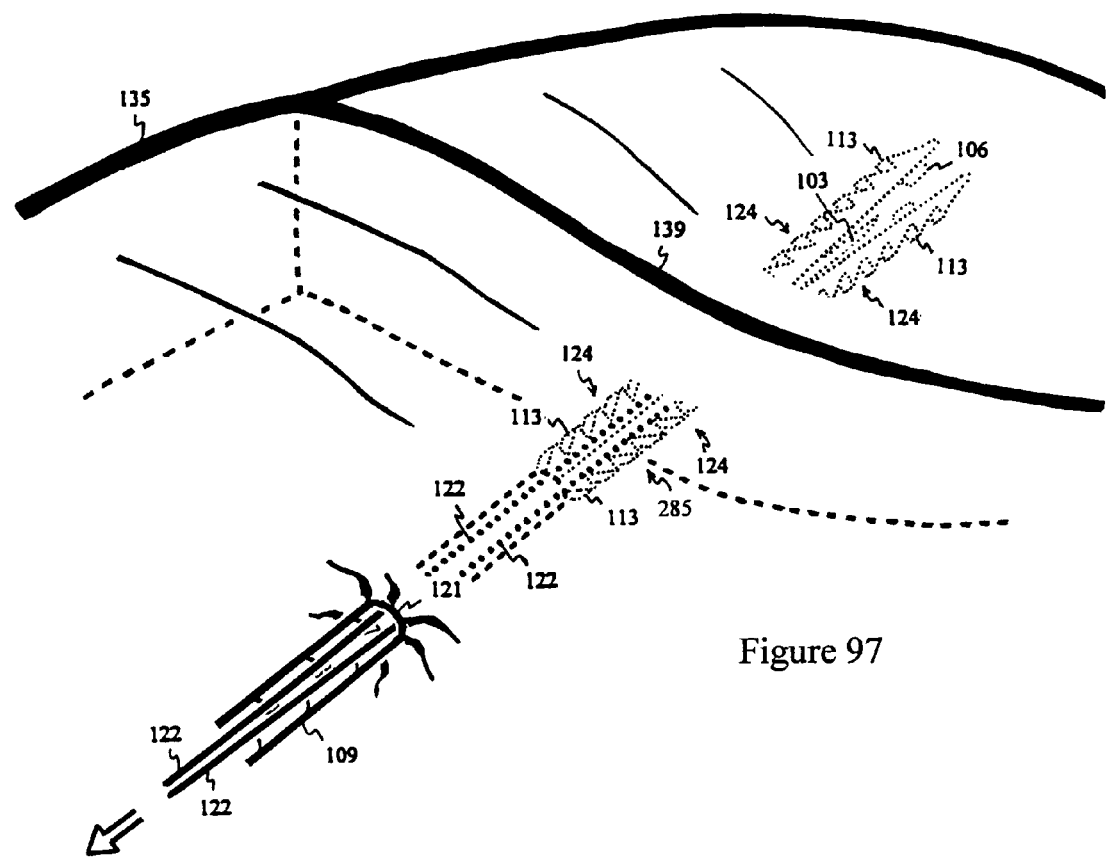
FIG. 97 depicts rejoining or approximating the torn portion with the main body of the meniscus 135 by pulling the suture 122.
Figure 98:
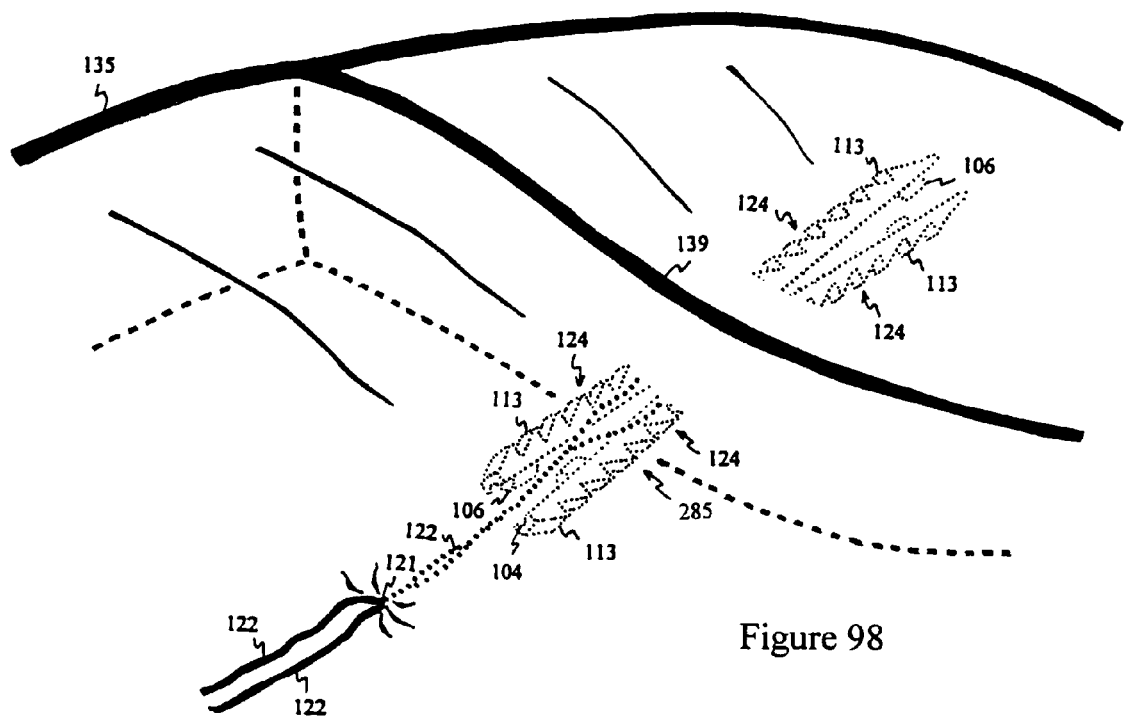
FIG. 98 shows complete withdrawal of the needle 103 to open and fasten the proximal legs 124. The compressive sleeve 109 is then also withdrawn to tightly fasten the tear 139. Excess suture 122 is then cut.

The attached suture 122 on the counter-gripping fastener 285 can also manipulate, reposition or tighten a repair. A counter-gripping fastener 285 with an attached suture 122, similar to the one in FIG. 94, is used to puncture and bridge a meniscal tear 139. The counter junction 120 is positioned at the tear 139, as shown in FIG. 95. To anchor the distal legs 124 of the counter-gripping fastener 285, the needle/trocar 103 is partially withdrawn while the compressive sleeve 109 is held stationary, as shown in FIG. 96. The distal legs 124 and the gripping elements 113 act as hooks anchoring into the torn portion of the meniscus 135. By pulling the suture 122, the torn portion anchored by the distal legs 124 of the fastener 285 rejoins the main body of the meniscus 135, as shown in FIG. 97. With constant tension on the suture 122, the needle 103 then compressive sleeve 109 are withdrawn to anchor the proximal legs 124 within the main body of the meniscus 135 for a tight meniscal 135 repair, as shown in FIG. 98. The suture 122 is preferred to be biodegradable and excess suture 122 is cut off.

In summary, the elastic legs 124 of the expandable fastener 144, 284, 285 or 286 are resiliently straightened by the trocars 103 during tissue insertion. The legs 124 are then allowed to curve after the withdrawal of the trocar 103, pressing the gripping elements 113 laterally into the tissue for fastening. In the curved position, the elastic leg 124 can have more than one curvature. Location and degree of the curvature of the legs 124 of the fastener 144, 284, 285 or 286 can vary. Curvatures of the legs 124 can also be asymmetrical or not in mirror image to each other.

The curved position can also be called the predisposed, deployed or relaxed position of the fastener 144, 284, 285 or 286. The straightened position can also be called the generally parallel, inserting, delivery, or installing position of the fastener 144, 284, 285 or 286.

A wide range of materials can be used to fabricate the expandable fastener 144, 284, 285 or 286. Biocompatible polymers, such as polypropylene, polyethylene, poly-etherether-ketone, acetal resin, polysulfone or polycarbonate are possible candidates. For biodegradable capability, the expandable fastener 144, 284, 285 or 286 can be made with polylactate, polyglycolic, poly(lactide-co-glycolide), polycaprolactone, trimethylene carbonate or combinations of these materials. Many of these degradable polymers are US FDA approved products. Other degradable polymers, such as polydioxanone, polyanhydride, trimethylene carbonate, poly-beta-hydroxybutyrate, polyhydroxyvalerate, polygama-ethyl-glutamate, poly(DTH iminocarbonate), poly (bisphenol A iminocarbonate), poly-ortho-ester, polycyanoacrylate or polyphosphazene can also be used. For strength, durability and elasticity, nickel-titanium alloy or spring-tempered stainless steel can be used.

The expandable fastener 144, 284, 285 or 286 can also be coated with biocompatible polymers, such as polyurethane, polytetrafluoroethylene, silicon, polyethylene or other material. For additional biological and surgical benefits, the expandable fastener 144, 284, 285 or 286 can also be coated with lubricant, growth factor, nutrient, buffering agent, collagen, hydroxyapatite, analgesic, sealant, blood clotting, antibiotic, water repellent, radiopaque or echogenic agents. All materials should be able to withstand sterilization by gamma, electron beam, autoclave, ETO, plasma or UV light to prevent infection.

The trocar/needle 103 and compressive sleeve 109 can be made with stainless steel, titanium, nickel titanium other metal or alloy. The trocar/needle 103 and compressive sleeve 109 can be coated with lubricant, antibiotic, blood clotting, radiopaque or echogenic agents. For hard-to-reach surgical sites, the trocar/needle 103 can be made curved to gain accessibility for the surgeon. To accommodate the curvature of the trocar/needle 103, the compressive sleeve 109 can also be made with elastic material, such as nickel titanium, polypropylene, polyethylene or other flexible material.

The suture 122 can be permanent or biodegradable, braided or monofilament. The suture 122 can also be metallic for strength and durability.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

It should be clear to one skilled in the art that the current embodiments, materials, constructions, methods, tissues or incision sites are not the only uses for which the invention may be used. It has been foreseen that the expandable fastener 144, 284, 285 or 286 and the trocar/needle 103 can be applied in other surgical and non-surgical purposes. In fact, the expandable fastener 144, 284, 285 or 286 can be used to fasten pictures on walls or machine parts prone to loosening. Different materials, constructions, methods or designs for the expandable fastener 144, 284, 285 or 286, trocar/needle 103 or the compressive sleeve 109 can be substituted and used. Nothing in the preceding description should be taken to limit the scope of the present invention. The full scope of the invention is to be determined by the appended claims.

What is claimed is:

1. An expandable fastener deployable with a needle, comprising:
  a first leg formed of an elastic material and having a curved position and a resiliently straightened position, when said first leg is in said curved position, said first leg having a convex side and a concave side,
  and wherein said first leg comprising a first semi-cylinder adhered and extending from a distal portion of said convex side of said first leg, and a first plurality of tissue gripping elements located on said concave side of said first leg,
  a second leg formed of an elastic material and having a curved position and a resiliently straightened position, when said second leg is in said curved position, said second leg having a convex side and a concave side,
  and wherein said second leg comprising a second semi-cylinder adhered and extending from a distal portion of said convex side of said second leg, and a second plurality of tissue gripping elements located on said concave side of said second leg,
wherein said first and second semi-cylinders are sized and configured to retain said needle,
when said first and second legs are in said curved positions, said first and second semi-cylinders are separate; and when said first and second legs are in said resiliently straightened positions, the first semi-cylinder is connected to the second leg and said second semi-cylinder is connected to said first leg.

2. The expandable fastener of claim 1, further comprising a first head portion attached to a proximal end of said first leg and a second head portion attached to a proximal end of said second leg.

3. The expandable fastener of claim 2, wherein said first head portion has at least one alignment opening, and said second head portion has at least one alignment peg that extends into said at least one alignment opening.

4. An expandable fastener, comprising:
a first elastically curved section having a resiliently straighten position and a curved position, said first elastically curved section comprising a first head portion, a first leg portion extending from said first head portion, a first groove indenting along a length of said first head portion and said first leg portion, and a first semi-cylinder adhered and covering a distal portion of said first groove,
a second elastically curved section having a resiliently straighten position and a curved position, said second elastically curved section comprising a second head portion, a second leg portion extending from said second head portion, a second groove indenting along a length of said second head portion and said second leg portion, and a second semi-cylinder adhered and covering a distal portion of said second groove, wherein said second semi-cylinder is separate from said first semi-cylinder in said curved position, and wherein said first groove connects to said second semi-cylinder and said second groove connects to said first semi-cylinder in said resiliently straighten positions.

5. The expandable fastener of claim 2 or 4, wherein said first and second head portions have tissue gripping elements extending therefrom.

6. The expandable fastener of claim 2 or 4, wherein said first and second head portions further comprise at least one tissue ingrowth opening.

7. The expandable fastener of claim 1, further comprising a first groove in said first leg and a second groove in said second leg, said first semi-cylinder enclosing a portion of said first groove and said second semi-cylinder enclosing a portion of said second groove.

8. The expandable fastener of claim 7 or 4, wherein said first and second grooves are non semi-cylindrical.

9. The expandable fastener of claim 4, further comprising a needle, said needle sized and configured to fit into said first and second grooves and said first and second semi-cylinders.

10. The expandable fastener of claim 4, wherein said first groove aligns with said second groove when said first and second elastically curved sections are in said resiliently straightened positions and a needle may be located through said first and second grooves and said first and second semi-cylinders, thereby holding said first and second elastically curved sections in said resiliently straightened positions.

11. The expandable fastener of claim 4, wherein said first and second grooves extend to an opening in a tip of said first and second elastically curved sections such that a needle may extend out from said tip.

12. An expandable fastener for deployment with a needle, said expandable fastener comprising: a first leg having tissue gripping elements located on a concave surface thereof, said first leg having a curved position and a resiliently straightened position, a second leg having tissue gripping elements located on a concave surface thereof, said second leg having a curved position and a resiliently straightened position, a head portion located at proximal ends of said first and second legs, a first semi-cylinder adhered and covering a distal portion of a first groove extending the length of said first leg, said first semi-cylinder sized and configured to allow the needle to be located therein; a second semi-cylinder adhered and covering a distal portion of a second groove extending the length of said second leg, and wherein, when the needle is located within said first and second semi-cylinders, said first and second legs are held together in said resiliently straightened positions; when said first and second legs are held in said second resiliently straightened positions, said at least one semi-cylinder is distal to said second semi-cylinder; and when said first and second legs are in said curved positions, said first and second semi-cylinders are separate.

13. The expandable fastener of claim 12, wherein said first groove has a first recess sized and configured to receive said second semi-cylinder and wherein said second groove has a second recess sized and configured to receive said first semi-cylinder forming said resiliently straightened positions.

14. The expandable fastener of claim 7, 9, 10, 11, or 12, wherein said needle is partially located within a sleeve, and wherein said sleeve is larger than said first and second grooves.

15. The expandable fastener of claim 1, wherein said needle is located in said first and second semi-cylinders, thereby holding said first and second legs in said resiliently straightened positions.

16. The expandable fastener of claim 1, further comprising a retainer sized and configured to fit around both of said first and second legs.

17. The expandable fastener of claim 4, further comprising a retainer sized and configured to fit around said first and second elastically curved sections.

18. The expandable fastener of claim 4, further comprising a retainer sized and configured to fit around said first and second head portions.

19. The expandable fastener of claim 16, 17 or 18, wherein said retainer is tapered.

20. The expandable fastener of claim 1 or 4, further comprising a suture attached to said expandable fastener.

21. The expandable fastener of claim 1 or 4, wherein said first and second semi-cylinders are tunnel-like potrusions.

22. The expandable fastener of claim 1 or 4, wherein said first and second legs are tapered.

23. The expandable fastener of claim 1 or 4, wherein said expandable fastener is formed of modular components.

24. The expandable fastener of claim 1 or 4, wherein said expandable fastener is formed of one or more materials chosen from the group of materials consisting of biocompatible polymers, polypropylene, polyethylene, poly-ether-ether-ketone, acetal resin, polysulfone, polycarbonate, biodegradable materials, polylactate, polyglycolic, poly-lactide-co-glycolide, polycaprolactone, trimethylene carbonate, polydioxanone, polyanhydride, trimethylene carbonate, poly-beta-hydroxybutyrate, polyhydroxyvalerate, poly-gama-ethyl-glutamate, poly-DTH iminocarbonate, poly-bisphenol A iminocarbonate, poly-ortho-ester, polycyanoacrylate and polyphosphazene.

25. The expandable fastener of claim 1 or 4, wherein said expandable fastener is formed of a material chosen from the group of materials consisting of nickel-titanium alloy and spring-tempered stainless steel.

26. The expandable fastener of claim 1 or 4, further comprising a coating on an exterior surface of said expandable fastener.

27. The expandable fastener of claim 26, wherein said coating is chosen from the group of coatings consisting of biocompatible polymers, polyurethane, polytetrafluoroethylene, silicon, polyethylene, lubricant, growth factor, nutrient, buffering agent, collagen, hydroxyapatite, analgesic agent, sealant, blood clotting agent, antibiotic agent, water repellent agent, radiopaque agent and echogenic agent.

28. The expandable fastener of claim 1 or 4, wherein a tissue-contacting surface located proximate said first and second legs is smooth.

29. The expandable fastener of claim 4, further comprising a plurality of tissue gripping elements extending from outside surfaces of said first and second elastically curved sections.

30. The expandable fastener of claim 29, wherein said plurality of tissue gripping elements form a stacking of cones around said expandable fastener along said outside surfaces.

31. The expandable fastener of claim 29, wherein said plurality of tissue gripping elements are angled.

32. The expandable fastener of claim 29, wherein said plurality of tissue gripping elements are barbs.

33. The expandable fastener of claim 32, wherein said tissue gripping elements are pointed in more than one direction.

34. The expandable fastener of claim 29, wherein said plurality of tissue gripping elements are semi-circular ridges that extend from said outside surfaces of said first and second elastically curved sections.

35. The expandable fastener of claim 4, wherein:
a first distance is between a proximal end of said first elastically curved section and a proximal end of said second elastically curved section,
a second distance is between a distal end of said first elastically curved section and a distal end of said second elastically curved section,
and wherein a first curvature of said first elastically curved section is configured such that said second distance is larger than said first distance.

36. The expandable fastener of claim 35, wherein a second curvature of said second curved section is configured such that said second distance is larger than said first distance.

37. The expandable fastener of claim 4, wherein said first and second grooves extend through said first and second head portions.

38. The expandable fastener of claim 4, further comprising at least one alignment opening located in said first elastically curved section, and at least one alignment peg extending from said second elastically curved section, said at least one alignment peg sized and configured to fit within said at least one alignment opening.

39. The expandable fastener of claim 38, wherein said at least one alignment opening is located in said first head portion and said at least one alignment peg extends from said second head portion.

40. The expandable fastener of claim 12, further comprising a retainer located around said first and second legs proximate said head portion.

41. The expandable fastener of claim 40, wherein said retainer is tapered.

42. The expandable fastener of claim 12, wherein, when said first and second legs are in said resiliently straightened positions, said tissue gripping elements form a stacking of cones around said first and second legs.

43. The expandable fastener of claim 12, further comprising a suture attached to said expandable fastener.

44. The expandable fastener of claim 12, further comprising at least one alignment opening indenting into said first leg and at least one alignment peg extending from said second leg.

45. The expandable fastener of claim 12, wherein said tissue gripping elements are non-cylindrical shape.

46. The expandable fastener of claim 12, wherein said first semi-cylinder extends to an opening in a tip of said first leg such that the needle may extend out from said tip.

47. The expandable fastener of claim 12, wherein said first and second legs are tapered.

48. The expandable fastener of claim 12, wherein said tissue gripping elements are barbs.

49. The expandable fastener of claim 48, wherein said tissue gripping elements are pointed in more than one direction.

50. The expandable fastener of claim 12, wherein said expandable fastener is formed of modular components.

51. The expandable fastener of claim 12, wherein said fastener is formed of one or more materials chosen from the group of materials consisting of biocompatible polymers, polypropylene, polyethylene, poly-ether-ether-ketone, acetal resin, polysulfone, polycarbonate, biodegradable materials, polylactate, polyglycolic, poly-lactide-co-glycolide, polycaprolactone, trimethylene carbonate, polydioxanone, polyanhydride, trimethylene carbonate, poly-beta-hydroxybutyrate, polyhydroxyvalerate, poly-gama-ethyl-glutamate, poly-DTH iminocarbonate, poly-bisphenol A iminocarbonate, poly-ortho-ester, polycyanoacrylate and polyphosphazene.

52. The expandable fastener of claim 12, wherein said fastener is formed of a material chosen from the group of materials consisting of nickel-titanium alloy and spring-tempered stainless steel.

53. The expandable fastener of claim 12, further comprising a coating on an exterior surface of said expandable fastener.

54. The expandable fastener of claim 53, wherein said coating is chosen from the group of coatings consisting of biocompatible polymers, polyurethane, polytetrafluoroethylene, silicon, polyethylene, lubricant, growth factor, nutrient, buffering agent, collagen, hydroxyapatite, analgesic agent, sealant, blood clotting agent, antibiotic agent, water repellent agent, radiopaque agent and echogenic agent.

55. The expandable fastener of claim 12, wherein said head portion has tissue gripping elements extending therefrom.

56. The expandable fastener of claim 12, wherein a tissue-contacting surface located proximate said first and second legs is smooth.

57. The expandable fastener of claim 12, wherein said first semi-cylinder opens through said head portion.

\* \* \* \* \*